United States Patent
DeVries Gelder et al.

(10) Patent No.: US 11,661,608 B2
(45) Date of Patent: *May 30, 2023

(54) HAPLOTYPES ASSOCIATED WITH IMPROVED DICAMBA TOLERANCE AND GLYPHOSATE TOLERANCE IN TRANSGENIC SOYBEAN PLANTS

(71) Applicant: Monsanto Technology LLC, St. Louis, MO (US)

(72) Inventors: Mindy L. DeVries Gelder, St. Louis, MO (US); Paul Feng, St. Louis, MO (US); Jesse J. Gilsinger, St. Louis, MO (US); Floyd G. Hancock, St. Louis, MO (US); Ivan Husic, St. Louis, MO (US); James Narvel, St. Louis, MO (US); Curtis W. Scherder, St. Louis, MO (US); Dean A. Ulbrich, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 134 days.

This patent is subject to a terminal disclaimer.

(21) Appl. No.: 16/832,679

(22) Filed: Mar. 27, 2020

(65) Prior Publication Data
US 2020/0263192 A1    Aug. 20, 2020

Related U.S. Application Data

(62) Division of application No. 14/402,700, filed as application No. PCT/US2013/042349 on May 23, 2013, now Pat. No. 10,604,767.

(60) Provisional application No. 61/650,869, filed on May 23, 2012, provisional application No. 61/650,852, filed on May 23, 2012, provisional application No. 61/753,725, filed on Jan. 17, 2013, provisional application No. 61/753,693, filed on Jan. 17, 2013, provisional application No. 61/779,739, filed on Mar. 13, 2013.

(51) Int. Cl.
C12N 15/82    (2006.01)
C12Q 1/6895   (2018.01)
A01H 1/04     (2006.01)

(52) U.S. Cl.
CPC ......... *C12N 15/8274* (2013.01); *A01H 1/045* (2021.01); *C12N 15/8209* (2013.01); *C12N 15/8275* (2013.01); *C12Q 1/6895* (2013.01); *C12Q 2600/13* (2013.01); *C12Q 2600/156* (2013.01); *C12Q 2600/172* (2013.01)

(58) Field of Classification Search
CPC .................................................. A01H 1/045
See application file for complete search history.

(56) References Cited

U.S. PATENT DOCUMENTS

| | | |
|---|---|---|
| 5,659,116 A | 8/1997 | Rhodes |
| 5,750,857 A | 5/1998 | Rhodes |
| 5,973,235 A | 10/1999 | Holmes |
| 6,005,170 A | 12/1999 | Lussenden |
| 6,080,917 A | 6/2000 | Lussenden |
| 6,143,953 A | 11/2000 | Buettner |
| 6,184,442 B1 | 2/2001 | Nickell |
| 6,346,658 B1 | 2/2002 | Moots |
| 6,348,644 B1 | 2/2002 | Rhodes |
| 6,632,982 B1 | 10/2003 | Floyd |
| 6,660,912 B1 | 12/2003 | Owen |
| 6,683,233 B1 | 1/2004 | Owen |
| 6,858,783 B2 | 2/2005 | Eby et al. |
| 6,881,879 B2 | 4/2005 | Floyd |
| 6,884,927 B1 | 4/2005 | Eby |
| 6,900,372 B2 | 5/2005 | Hicks |
| 6,933,423 B2 | 8/2005 | Narvel |
| 7,022,896 B1 | 4/2006 | Weeks et al. |
| 7,067,723 B2 | 6/2006 | Narvel |
| 7,071,388 B2 | 7/2006 | Narvel |
| 7,105,724 B2 | 9/2006 | Weeks et al. |
| 7,135,626 B2 | 11/2006 | Davis |
| 7,294,764 B2 | 11/2007 | Leitz |
| 7,378,578 B2 | 5/2008 | Narvel |
| 7,388,131 B1 | 6/2008 | Hicks |
| 7,479,582 B2 | 1/2009 | Moots et al. |
| 7,482,516 B2 | 1/2009 | Hicks |
| 7,498,489 B2 | 3/2009 | Jenkinson et al. |
| 7,502,113 B2 | 3/2009 | Deppermann et al. |
| 7,504,565 B2 | 3/2009 | Jenkinson et al. |
| 7,554,014 B2 | 6/2009 | Moots et al. |
| 7,569,750 B2 | 8/2009 | Behm |
| 7,592,516 B2 | 9/2009 | Floyd et al. |
| 7,728,197 B1 | 6/2010 | Bowers et al. |

(Continued)

FOREIGN PATENT DOCUMENTS

WO    2012/031097 A2    3/2012

OTHER PUBLICATIONS

Behrens et al., "Dicamba Resistance: Enlarging and Preserving Biotechnology-Based Weed Management Strategies", Science, May 25, 2007, pp. 1185-1188.

(Continued)

*Primary Examiner* — David H Kruse

(74) *Attorney, Agent, or Firm* — Thompson Coburn LLP; William A. Holtz; Chunping Li

(57) ABSTRACT

The present invention provides methods and compositions for the identification and selection of soybean plants that comprise a genotype associated with dicamba tolerance. In addition, methods are provided for screening germplasm entries for the performance and expression of this trait.

13 Claims, 2 Drawing Sheets

Specification includes a Sequence Listing.

(56) References Cited

U.S. PATENT DOCUMENTS

| | | | |
|---|---|---|---|
| 7,812,224 | B2 | 10/2010 | Weeks et al. |
| 7,964,777 | B2 | 6/2011 | Eby |
| 8,921,647 | B2 | 12/2014 | Cerny et al. |
| 9,617,605 | B2 | 4/2017 | Cerny et al. |
| 10,604,767 | B2 * | 3/2020 | DeVries Gelder ......................... C12N 15/8274 |
| 2006/0288444 | A1 | 12/2006 | McCarroll et al. |
| 2009/0036308 | A1 | 2/2009 | Guida, Jr. et al. |
| 2009/0064354 | A1 | 3/2009 | Narvel et al. |
| 2009/0105077 | A1 | 4/2009 | Bhatti et al. |
| 2009/0165166 | A1 | 6/2009 | Feng et al. |
| 2009/0208964 | A1 | 8/2009 | McCarroll et al. |
| 2010/0099859 | A1 | 4/2010 | Malven et al. |
| 2010/0122372 | A1 | 5/2010 | Sebastian et al. |
| 2012/0084879 | A1 | 4/2012 | Cerny et al. |
| 2015/0216135 | A1 | 8/2015 | Gilsinger et al. |

OTHER PUBLICATIONS

Charlson et al., "Associating SSR Markers With Soybean Resistance to Iron Deficiency Chlorosis", Journal of Plant Nutrition, Nov. 2003, vol. 26, No. 10-11, pp. 2267-2276.

Choi et al., "A Soybean Transcript Map: Gene Distribution, Haplotype and Single-Nucleotide Polymorphism Analysis", Genetics, May 2007, pp. 685-696, vol. 176.

Collard et al., "Marker-assisted selection: an approach for precision plant breeding in the twenty-first century", Philosophical Transactions of the Royal Society, Aug. 22, 2007, pp. 557-572, vol. 363.

Delannay et al., "Yield Evaluation of a Glyphosate-Tolerant Soybean Line after Treatment with Glyphosate", Crop Science, 1995, pp. 1461-1467, vol. 35.

GenBank BG406195.1, "sac36g03.y1 Gm-c1051 Glycine Max cDNA CloneGenome Systems Clone ID: Gm-c1051-4518 5-, mRNA Sequence", Jul. 22, 2004 (online), retrieved Dec. 27, 2011, Available on the Internet: <URL: http://www.ncbi.nlm.nih.gov/nucest/BG406195>.

GenBank BU082700.1, "saq36h09.y.1 Gm-c1045 Glycine Max cDNA Clone Soybean Clone ID: Gm-c1045-6906 5-Similar to TR:Q9SSA4 Hypothetical 46.0 KD Protein, mRNA Sequence", Jul. 2, 2004 (online), retrieved Dec. 27, 2011, Available on the Internet: <URL: http://www.ncbi.nlm.nih.gov/nucest/BU082700>.

Grant et al., "SoyBase, the USDA-ARS Soybean Genetics and Genomics Database", Nucleic Acids Research, 2010, pp. D843-D846, vol. 38.

Heffner et al., "Genomic Selection for Crop Improvement", Crop Science, Jan.-Feb. 2009, pp. 1-12, vol. 49.

Hyten et al., "A High Density Integrated Genetic Linkage Map of Soybean and the Development of a 1536 Universal Soy Linkage Panel for Quantitative Trait Locus Mapping", Crop Science, May-Jun. 2010, pp. 960-968, vol. 50.

Hyten et al., "High-throughput SNP Discovery Through Deep Resequencing of a Reduced Representation Library to Anchor and Orient Scaffolds in the Soybean Whole Genome Sequence", BMC Genomics, 2010, pp. 1-8, vol. 11 No. 38.

Kilen, T.C., "A favorable linkage combination in the soybean", The Journal of Heredity, Jul.-Aug. 1986, pp. 275-277, vol. 77.

Krueger et al., "Use of Dicamba-Degrading Microorganisms to Protect Dicamba Susceptible Plant Species", Journal of Agricultural and Food Chemistry, American Chemical Society, Jan. 1, 1991, vol. 29, pp. 1000-1003.

Meyer et al., "Genetic Factors Influencing Adverse Effects of Mesotrione and Nicosulfuron on Sweet Corn Yield", Agronomy Journal, May 10, 2010, pp. 1138-1144, vol. 102 No. 4.

Padgette et al., "Development, Identification, and Characterization of a Glyphosate-Tolerant Soybean Line", Crop Science, 1995, pp. 1451-1461, vol. 35.

Que et al., "Trait Stacking in Transgenic Crops: Challenges and Opportunities", GM Crops, Jul.-Aug. 2010, pp. 220-229, vol. 1 No. 4.

Ray et al., "Soybean natural cross-pollination rates under field conditions", Environmental Biosafety Research, Apr.-Jun. 2003, pp. 133-138, vol. 2 No. 2, Abstract Only.

Shoemaker et al., "Public Soybean EST Project", Genbank [database online], 1999 [retrieved on Dec. 6, 2013], retrieved from the internet: <URL: http://www.ncbi.nlm.nih.gov/nucest/23735360?report=genbank> Acession: BU765955.

Song et al., "A New Integrated Genetic Linkage Map of the Soybean", Theoretical and Applied Genetics, Jun. 2004, pp. 122-128, vol. 109, No. 1.

Wang et al., "Association Mapping of Iron Deficiency Chlorosis Loci in Soybean (*Glycine max* L. Merr.) Advance Breeding Lines", Theoretical and Applied Genetics, Apr. 2008, pp. 777-787, vol. 116, No. 6.

Wax et al., "Differential Response of Soybean Cultivars to Metribuzin", Agronomy Journal, May-Jun. 1976, pp. 484-486, vol. 68.

Yoon et al., "BARCSoySNP23: A Panel of 23 Selected SNPs for Soybean Cultivar Identification", Theoretical and Applied Genetics, 2007, pp. 885-899, vol. 114.

* cited by examiner

HAPLOTYPES ASSOCIATED WITH IMPROVED DICAMBA TOLERANCE AND GLYPHOSATE TOLERANCE IN TRANSGENIC SOYBEAN PLANTS

CROSS-REFERENCE TO RELATED APPLICATIONS

This application is a divisional of U.S. patent application Ser. No. 14/402,700, filed Nov. 21, 2014, now U.S. Pat. No. 10,604,767, which is a national stage application, filed under 35 U.S.C. § 371, of International Patent Application No. PCT/US2013/042349, filed May 23, 2013, which claims the benefit of U.S. Provisional Patent Application No. 61/779,739, filed Mar. 13, 2013; U.S. Provisional Patent Application No. 61/753,725, filed Jan. 17, 2013; U.S. Provisional Patent Application No. 61/753,693, filed Jan. 17, 2013; U.S. Provisional Patent Application No. 61/650,869, filed May 23, 2012; and U.S. Provisional Patent Application No. 61/650,852, filed May 23, 2012, each of which are incorporated by reference herein in its entirety.

INCORPORATION OF SEQUENCE LISTING

A sequence listing containing the file named "46_21_59246_A_PCT.txt" which is 33,292 bytes (measured in MS-Windows®) and created on May 20, 2013, comprises 56 nucleotide sequences, is provided herewith via the USPTO's EFS system and is herein incorporated by reference in its entirety.

INCORPORATION OF TABLE 2

A listing of various soybean linkage group L (chromosome 19) markers is provided herewith in the Specification as Table 2.

BACKGROUND

International Patent Application Publication WO 2012/031097 describes genetic regions of soybean linkage group L that contain polymorphic loci that are associated with an undesirable "yellow flash" phenotype that is observed in the foliage of certain soybean varieties that comprise a transgene that confers resistance to glyphosate that are exposed to glyphosate.

SUMMARY

"Dicamba intolerance" is an undesirable phenotype observed in certain soybean varieties that comprise a transgene that can confer resistance to the broad-spectrum herbicide dicamba. After application of dicamba, it has been discovered that the leaves of certain soybean plant varieties comprising the transgene that confers resistance to dicamba can exhibit a "dicamba intolerance phenotype" comprising malformation (epinasty) of the main stem and petioles upon exposure to dicamba. The epinastic growth habit of such "dicamba intolerant" transgenic plants is manifest in pronounced bending/twisting of the main stem and petioles. In dicamba intolerant transgenic soybean plants exposed to dicamba, the upper nodes and petioles may die, but lower portion of the plant may remain vegetative and new growth can be limited. However, other soybean plant varieties containing the same transgene that confers resistance to dicamba do not exhibit the dicamba intolerance phenotype when co-exposed to the same dosage of dicamba. The dicamba intolerance phenotype can be observed within approximately 2 to 10 days after herbicide application in certain soybean varieties comprising the transgene that confers resistance to dicamba. The dicamba intolerance phenotype is undesirable as it can lead to reduced yield in certain transgenic soybean plant varieties exposed to dicamba.

Although the dicamba intolerance phenotype can be observed within approximately 2 to 10 days after dicamba application in certain soybean varieties comprising the transgene that confers dicamba resistance, distinct soybean varieties that comprise the same dicamba resistance transgene integrated at the same chromosomal locus (i.e. the same transgenic event) can show various degrees of dicamba intolerance upon exposure to high doses of dicamba. Some varieties comprising the dicamba resistance transgene insertion are highly tolerant to high dosages of dicamba, showing no dicamba intolerance phenotype (i.e. a "dicamba tolerance phenotype"), while other varieties comprising the same dicamba resistance transgene insertion are highly susceptible to high dosages of dicamba, showing a severe dicamba intolerance phenotype. Provided herein are soybean plants comprising an introgressed genomic region associated with a dicamba tolerance phenotype. Also provided herein are markers that reside outside of a genomic region associated with a dicamba tolerance phenotype and that facilitate breeding activities that include, but are not limited to, introgression of this genomic region. Markers and specific alleles thereof that are associated with a dicamba tolerance phenotype are also provided. Methods of obtaining a soybean plant that exhibits a dicamba tolerance phenotype and methods of obtaining a soybean plant comprising in its genome at least one dicamba tolerance locus are also provided. Methods that provide for the introgression of a genomic region associated with a dicamba tolerance phenotype into soybean germplasm that has a genomic region associated with a dicamba intolerance phenotype are also provided. Identification of molecular markers associated with loci that confer the dicamba tolerance phenotype has significant economic value. By using markers associated with the dicamba tolerance trait, breeders can select soybean varieties with the favorable alleles (i.e. alleles that are not associated with the dicamba intolerance trait) for use in trait integration. They can also use the markers to help them eliminate unfavorable alleles (i.e. alleles that are associated with the dicamba intolerance trait) in soybeans. In certain embodiments, commercially desirable transgenic soybean lines that carry a genomic region that is associated with a "dicamba tolerance" phenotype and tolerate high dosages of dicamba are thus provided.

It has also been surprisingly observed that soybean plants comprising the dicamba tolerance loci, a transgene conferring resistance to dicamba, and a transgene conferring resistance to glyphosate also exhibit improved reproductive tolerance to glyphosate application relative to plants with the same two transgenes that lack the dicamba tolerance loci. Although the glyphosate reproductive intolerance phenotype can be observed after late stage (i.e. V6/R1) glyphosate application in certain soybean varieties comprising the transgenes that confer dicamba and glyphosate resistance, distinct soybean varieties that comprise the same dicamba and glyphosate resistance transgene integrated at the same chromosomal loci (i.e. the same transgenic events) can show various degrees of glyphosate reproductive intolerance (i.e. varying degrees of sterility) upon such exposure to glyphosate. Some varieties comprising the dicamba and glyphosate resistance transgene insertions are highly tolerant to late stage glyphosate application, showing no sterility phenotype (i.e. a "glyphosate reproductive intolerance phenotype"), while other varieties comprising the same dicamba and glyphosate resistance transgene insertions are highly susceptible to late stage glyphosate application, showing varying levels of sterility. Provided herein are soybean plants comprising an introgressed genomic region associated with a dicamba tolerance phenotype that also provide for reproductive tolerance to glyphosate. Also provided herein are markers that reside outside of a genomic region associated with a dicamba tolerance/reproductive tolerance to glyphosate phenotype and that facilitate breeding activities that include, but are not limited to, introgression of this genomic region. Markers and specific alleles thereof that are associated with a dicamba tolerance/reproductive tolerance to glyphosate are also provided. Methods of obtaining a soybean plant that exhibits reproductive tolerance to glyphosate and methods of obtaining a soybean plant comprising in its genome at least one dicamba tolerance/reproductive tolerance to glyphosate locus are also provided. Methods that provide for the introgression of a genomic region associated with reproductive tolerance to glyphosate into soybean germplasm that has a genomic region associated with a reproductive tolerance to glyphosate are also provided. Identification of molecular markers associated with loci that confer reproductive tolerance to glyphosate has significant economic value. By using markers associated with the reproductive tolerance to glyphosate trait, breeders can select soybean varieties with the favorable alleles (i.e. alleles that are not associated with the glyphosate reproductive intolerance trait) for use in trait integration. They can also use the markers to help them eliminate unfavorable alleles (i.e. alleles that are associated with the glyphosate reproductive intolerance trait) in soybeans. In certain embodiments, commercially desirable transgenic soybean lines that carry a genomic region that is associated with a "glyphosate reproductive tolerance" phenotype and tolerate late stage (i.e. V6/R1) application of glyphosate are thus provided.

Methods of identifying a soybean plant that comprises a genotype associated with a dicamba tolerance phenotype and/or a glyphosate reproductive tolerance phenotype are thus provided.

In certain embodiments, the plurality of soybean plants comprises a population that is obtained by: i) crossing a parent plant comprising at least one dicamba tolerance locus with a parent plant comprising at least one dicamba intolerance locus; or, ii) obtaining seed or progeny from a parental plant segregating for at least one dicamba tolerance locus. In certain embodiments, the population contains plants that comprise a transgene that confers resistance to dicamba. In certain embodiments, the aforementioned methods can further comprise the step of assaying for the presence of at least one additional marker, where the additional marker is either linked or unlinked to the linkage group L genomic region. In certain embodiments of the aforementioned methods, the plurality of soybean plants, the soybean plant, and/or progeny thereof are exposed to a dosage of dicamba sufficient to cause dicamba intolerance in a susceptible variety. In certain embodiments of the aforementioned methods, a plant that exhibits a dicamba tolerance phenotype is selected.

Also provided herewith are methods for producing a soybean plant comprising in its genome at least one introgressed dicamba tolerance locus. Also provided herewith are soybean plants comprising an introgressed dicamba tolerance locus made by the aforementioned methods. In certain embodiments, a soybean plant comprising an introgressed dicamba tolerance locus and one or more polymorphic loci comprising alleles or combinations of alleles that are not found in a dicamba tolerant soybean variety and that are linked to the introgressed dicamba tolerance locus, where the plant is produced by the aforementioned methods are provided.

Also provided are soybean plants comprising an introgressed dicamba tolerance locus and one or more polymorphic loci comprising alleles or combinations of alleles that are not found in a dicamba tolerant soybean variety and that are linked to the introgressed dicamba tolerance locus.

Methods of identifying a soybean plant that comprises a genotype associated with dicamba tolerance and/or reproductive tolerance to glyphosate are thus provided. In certain embodiments, the methods can comprise detecting in a soybean plant an allele in at least one genetic locus associated with dicamba tolerance and/or reproductive tolerance to glyphosate, where the genetic locus is in a linkage group L genomic region flanked by loci M0205928 (SEQ ID NO: 4) and BU765955 (SEQ ID NO: 12), and denoting that the plant comprises a genotype associated with dicamba tolerance. In certain embodiments, the methods can further comprise the step of selecting the denoted plant from a population of plants. In certain embodiments, the plant comprises a transgene that confers resistance to dicamba and/or a transgene that confers resistance to glyphosate. In certain embodiments, the soybean plant or progeny thereof is exposed to a dosage of dicamba sufficient to cause a deleterious effect in a susceptible variety comprising the transgene and/or is exposed to a dosage of glyphosate sufficient to cause sterility in a susceptible variety comprising the transgene(s). In certain embodiments of any of the aforementioned methods, a plant that exhibits dicamba tolerance and/or reproductive tolerance to glyphosate is selected. In certain embodiments of any of the aforementioned methods, a genotype associated with a dicamba tolerance comprises at least one polymorphic allele of at least one marker in a first sub-region of the linkage group L region that is flanked by loci M0205928 (SEQ ID NO: 4) and M0129138 (SEQ ID NO: 6) and/or at least one polymorphic allele of at least one marker in a second sub-region of the linkage group L region that is flanked by loci BU551363 (SEQ ID NO: 9) and BU765955 (SEQ ID NO: 12) and/or at least one polymorphic allele of at least one marker in a third sub-region of the linkage group L region that is flanked by loci BU55345 (SEQ ID NO:7) and M0114388 (SEQ ID NO:8) is provided. In certain embodiments of any of the aforementioned methods, the genotype associated with dicamba tolerance comprises at least one polymorphic allele of at least one marker in the linkage group L region selected from the group consisting of a TT allele M0205350 (SEQ ID NO: 10), a TT allele of M0101742 (SEQ ID NO: 5), a CC allele of M0102027 (SEQ ID NO: 11), and an AA allele of NGMAX008197032 (SEQ ID NO:52).

Methods for obtaining a soybean plant comprising in its genome at least one dicamba tolerance locus are also provided. In certain embodiments, these methods can compromise the steps of: (a) genotyping a plurality of soybean plants with respect to at least one genetic locus in a linkage group L genomic region flanked by loci M0205928 (SEQ ID NO: 4) and BU765955 (SEQ ID NO: 12); and, (b) selecting a soybean plant comprising in its genome at least one genetic locus comprising a genotype associated with dicamba tolerance. In certain embodiments of these methods, the genotype associated with dicamba tolerance comprises at least one polymorphic allele of at least one marker in a first sub-region of the linkage group L region flanked by loci M0205928 (SEQ ID NO: 4) and M0129138 (SEQ ID NO: 6) and/or at least one polymorphic allele of at least one marker in a second sub-region of the linkage group L region that is flanked by loci BU551363 (SEQ ID NO: 9) and BU765955 (SEQ ID NO: 12) and/or at least one polymorphic allele of at least one marker in a third sub-region of the linkage group L region that is flanked by loci BU55345 (SEQ ID NO:7) and M0114388 (SEQ ID NO:8). In certain embodiments of any of these aforementioned methods, the genotype associated with dicamba tolerance comprises at least one polymorphic allele of at least one marker in the first linkage group L region, the first sub-region, the second sub-region, or the third sub-region, where the marker is selected from the group consisting of a TT allele M0205350 (SEQ ID NO: 10), a TT allele of M0101742 (SEQ ID NO: 5), a CC allele of M0102027 (SEQ ID NO: 11), and an AA allele of NGMAX008197032 (SEQ ID NO:52). In certain embodiments of these methods, the plurality of soybean plants comprises a population that is obtained by: i) crossing a parent plant comprising at least one dicamba tolerance locus with a parent plant comprising at least one dicamba sensitivity locus; or, ii) obtaining seed or progeny from a parental plant segregating for at least one dicamba tolerance locus. In certain embodiments of these methods, the population contains plants that comprise at least one transgene that confers resistance to dicamba and/or a transgene that confers resistance to glyphosate. In certain embodiments of any of the aforementioned methods, the methods can further comprise the step of assaying for the presence of at least one additional marker, where the additional marker is either linked or unlinked to the linkage group L genomic region. In certain embodiments of any of the aforementioned methods, the plurality of soybean plants, the soybean plant, and/or progeny thereof are exposed to a dosage of dicamba sufficient to cause a deleterious effect in a susceptible variety comprising the transgene and/or is exposed to a dosage of glyphosate sufficient to cause sterility in a susceptible variety comprising the transgene. In certain embodiments of any of the aforementioned methods, a plant that exhibits dicamba tolerance and/or reproductive tolerance to glyphosate is selected.

Methods for producing a soybean plant comprising in its genome at least one introgressed dicamba tolerance locus are also provided. In certain embodiments, these methods comprise the steps of: (a) crossing a first soybean plant with a dicamba tolerance locus with a second soybean plant comprising: a dicamba sensitivity locus in a first linkage group L genomic region flanked by loci M0205928 (SEQ ID NO: 4) and M0129138 (SEQ ID NO: 6) and/or at least one polymorphic allele of at least one marker in a second sub-region of the linkage group L region that is flanked by loci BU551363 (SEQ ID NO: 9) and BU765955 (SEQ ID NO: 12) and/or at least one polymorphic allele of at least one marker in a third sub-region of the linkage group L region that is flanked by loci BU55345 (SEQ ID NO:7) and M0114388 (SEQ ID NO:8) and at least one linked polymorphic locus not present in the first soybean plant to obtain a population segregating for the dicamba tolerance loci and the linked polymorphic locus; (b) detecting at least two polymorphic nucleic acids in at least one soybean plant from the population, where at least one of the polymorphic nucleic acids is located in the first linkage group L region and/or the second linkage group L region and where at least one of the polymorphic amino acids is a linked polymorphic locus not present in the first soybean plant; and (c) selecting a soybean plant comprising a genotype associated with dicamba tolerance and at least one linked marker found in the second soybean plant comprising a dicamba sensitivity locus but not in the first soybean plant, thereby obtaining a soybean plant comprising in its genome at least one introgressed dicamba tolerance locus. In certain embodiments of these methods, at least one of the first or the second soybean plants comprises a transgene that confers resistance to dicamba and/or a transgene that confers resistance to glyphosate. In certain embodiments of these methods, the population, the selected soybean plant, and/or progeny of selected soybean plant is exposed to a dosage of dicamba sufficient to cause a deleterious effect in a susceptible variety comprising the transgene and/or is exposed to a dosage of glyphosate sufficient to cause sterility in a susceptible variety comprising the transgene. In certain embodiments of these methods, the polymorphic nucleic acid detected in step (b) is detected with at least one marker selected from the group consisting of M0205350 (SEQ ID NO: 10), M0101742 (SEQ ID NO: 5), M0102027 (SEQ ID NO: 11), and NGMAX008197032 (SEQ ID NO:52). In certain embodiments of these methods, the polymorphic nucleic acid detected in step (b) comprises a TT allele of M0205350 (SEQ ID NO: 10), a TT allele of M0101742 (SEQ ID NO: 5), a CC allele of M0102027 (SEQ ID NO: 11), and an AA allele of NGMAX008197032 (SEQ ID NO:52). In certain embodiments of these methods, the polymorphic nucleic acid detected in step (b) is detected with marker M0205350 (SEQ ID NO: 10) or M0102027 (SEQ ID NO: 11). In certain embodiments of these methods, the polymorphic nucleic acids are detected with marker M0101742 (SEQ ID NO: 5). In certain embodiments of these methods, the polymorphic nucleic acids are detected with marker NGMAX008197032 (SEQ ID NO:52). In certain embodiments of any of the aforementioned methods, the linked polymorphic locus is detected with a genotypic marker, a phenotypic marker, or both. In certain embodiments of these methods, the linked polymorphic locus is detected with a marker that is located within about 1000, 500, 100, 40, 20, 10, or 5 kilobases (Kb) of the dicamba tolerance locus. In certain embodiments of these methods, the linked polymorphic locus is detected with at least one marker selected from the group consisting of asmbl_11856 (SEQ ID NO: 1), TC122822 (SEQ ID NO: 2), BI967232 (SEQ ID NO: 3), M0205537 (SEQ ID NO: 15), M0202715 (SEQ ID NO: 16), M0206286 (SEQ ID NO: 17), M0206054 (SEQ ID NO: 18), and M0205375 (SEQ ID NO: 19).

Transgenic soybean plants comprising introgressed linkage group L regions comprising at least one polymorphic allele of at least one marker in a first sub-region of the linkage group L region that flanked by loci M0205928 (SEQ ID NO: 4) and M0129138 (SEQ ID NO: 6) and/or at least one polymorphic allele of at least one marker in a second sub-region of the linkage group L region that is flanked by loci BU551363 (SEQ ID NO: 9) and BU765955 (SEQ ID NO: 12) and/or at least one polymorphic allele of at least one marker in a third sub-region of the linkage group L region that is flanked by loci BU55345 (SEQ ID NO:7) and M0114388 (SEQ ID NO:8), where the polymorphic alleles are associated with dicamba tolerance and/or reproductive tolerance to glyphosate, and where the plant comprises a transgene that confers resistance to dicamba are also provided. In certain embodiments, the polymorphic alleles comprise a TT allele of M0205350 (SEQ ID NO: 10), a TT allele of M0101742 (SEQ ID NO: 5), a CC allele of M0102027 (SEQ ID NO: 11), and an AA allele of NGMAX008197032 (SEQ ID NO:52). In certain embodiments, the transgenic plant exhibits dicamba tolerance. In certain embodiments, the transgenic plant further comprises a transgene that confers resistance to glyphosate and exhibits reproductive tolerance to glyphosate. In certain embodiments of any one of the aforementioned methods, the plant further comprises at least one of a 2,4-D, glufosinate, bromoxynil, acetolactate synthase (ALS), acetyl CoA carboxylase (ACCase), hydroxyphenyl pyruvate dioxygenase (HPPD), or sulfonylurea herbicide resistance transgenes and/or at least one transgene selected from the group of transgenes conferring insect resistance, nematode resistance, fungal resistance, an improvement in seed oil quantity, an improvement in seed oil quality, abiotic stress resistance, and intrinsic yield increases. In certain embodiments, the insect resistance conferring transgene is a transgene that expresses an insecticidal *Bacillus thuringiensis* protein.

Also provided herein are soybean plants comprising a dicamba tolerance locus, a transgene conferring resistance to glyphosate, a transgene conferring resistance to dicamba, where the plants exhibit both improved dicamba tolerance and improved reproductive tolerance to glyphosate relative to soybean plants comprising the same two transgenes but lacking the dicamba tolerance locus. Such improved reproductive tolerance to glyphosate is reflected in reduced sterility when the plants are exposed to glyphosate.

In certain embodiments, the dicamba tolerance locus provided herein can provide for improved performance of additional combinations of transgenic traits (i.e. "stacked transgenic traits") in soybean plants. In such embodiments, the dicamba tolerance locus provided herein can be alternatively referred to and considered a "stacked transgenic trait improvement" locus. Allele(s) of the dicamba tolerance locus or "stacked transgenic trait improvement" locus that do not confer such dicamba tolerance or such stacked transgenic trait improvements are referred to herein as dicamba sensitivity or "stacked transgenic trait sensitivity" loci. Transgenic plants comprising the stacked transgenic trait improvement locus provided herein exhibit improved performance of both transgenes present in the transgenic plant relative to plants comprising the same two transgenes that lack the stacked transgenic trait improvement locus. Such improved performance can manifest in any of enhanced transgenic trait performance, increased transgene efficacy, and/or increased transgene expression. Transgenic plants comprising the stacked transgenic trait improvement locus and two transgenes are thus provided herein. Thus, in certain embodiments the two independent and distinct transgenes that exhibit improved performance in the presence of the stacked transgenic trait improvement locus both contribute to the same trait. In certain embodiments, this same trait is selected from the group consisting of resistance to a single herbicide, resistance to an insect, resistance to a nematode, resistance to a fungal disease, resistance to an abiotic stress, an improvement in seed oil quantity, an improvement in seed oil quality, and intrinsic yield increases. In certain embodiments, the two transgenes can contribute to the same herbicide resistance trait where the herbicide resistance is selected from the group consisting of glyphosate, dicamba, 2,4-D, glufosinate, bromoxynil, synthetic auxins, and inhibitors of acetolactate synthase (ALS), acetyl CoA carboxylase (ACCase) and hydroxyphenyl pyruvate dioxygenase (HPPD) resistance. In certain embodiments, the two transgenes can contribute to the same insect, fungal, or nematode resistance trait where the resistance to the same insect, fungal, or nematode pest is by a different mode of action to provide for improved pest resistance management. In other embodiments, the two transgenes can be two independent and distinct transgenes that encode different genes but contribute to a different trait. In certain embodiments, this different trait is independently selected from the group consisting of resistance to one or more herbicide(s), resistance to one or more insect(s), resistance to one or more nematode(s), resistance to one or more fungal disease(s), resistance to one or more abiotic stress(es), one or more improvement(s) in seed oil quantity or quantities, one or more improvement(s) in seed oil quality or qualities, intrinsic yield increases, and combinations thereof. In certain embodiments the stacked trait improvement locus is an herbicide tolerance locus that provides for improved tolerance to at least two distinct herbicides in plants comprising at least two transgenes that respectively confer resistance to those two herbicides. In certain embodiments, the herbicide tolerance locus provides for improved tolerance to at least two herbicides selected from the group consisting of glyphosate, dicamba, 2,4-D, glufosinate, bromoxynil, synthetic auxins, and inhibitors of acetolactate synthase (ALS), acetyl CoA carboxylase (ACCase) and hydroxyphenyl pyruvate dioxygenase (HPPD) resistance in plants comprising at least two transgenes that confer resistance to those two herbicides. In certain embodiments, the herbicide tolerance locus confers improved tolerance to dicamba, improved reproductive tolerance to glyphosate, and improved tolerance to a synthetic auxin that includes, but is not limited to 2, 4-D, in a plant comprising transgenes that confer resistance to dicamba, glyphosate, and the synthetic auxin that includes, but is not limited to 2, 4-D. In certain embodiments, the two transgenes can confer a distinct herbicide resistance trait where the herbicide resistance is selected from the group consisting of glyphosate, dicamba, 2,4-D, glufosinate, bromoxynil, synthetic auxins other than 2,4-D, acetolactate synthase (ALS), acetyl CoA carboxylase (ACCase) and hydroxyphenyl pyruvate dioxygenase (HPPD) resistance. Provided herein are soybean plants comprising any combination of a stacked trait improvement locus and at least two transgenes conferring herbicide tolerance selected from the group consisting of glyphosate, dicamba, 2,4-D, glufosinate, bromoxynil, synthetic auxins, and inhibitors of acetolactate synthase (ALS), acetyl CoA carboxylase (ACCase) and hydroxyphenyl pyruvate dioxygenase (HPPD). In certain embodiments, soybean plants comprising an introgressed stacked trait improvement locus, at least one transgene selected from the group consisting of glyphosate, dicamba, 2,4-D, glufosinate, bromoxynil, synthetic auxins other than 2,4-D, acetolactate synthase (ALS), acetyl CoA carboxylase (ACCase), hydroxyphenyl pyruvate dioxygenase (HPPD), and sulfonylurea herbicide resistance transgenes, and at least one transgene selected from the group of transgenes conferring insect resistance, nematode resistance, fungal resistance, an improvement in seed oil quantity, an improvement in seed oil quality, abiotic stress resistance, and intrinsic yield increases are provided. In still other embodiments, soybean plants comprising an introgressed stacked trait improvement locus, at least one transgene selected from the group consisting of glyphosate, dicamba, 2,4-D, and at least one transgene conferring resistance to an insect are provided. In still other embodiments, soybean plants comprising an introgressed stacked trait improvement locus, at least one transgene selected from the group consisting of glyphosate, dicamba, glufosinate, and 2,4-D resistance conferring transgenes, and at least one transgene conferring resistance to an insect that encodes a *Bacillus thuringiensis* toxin are provided. In certain embodiments, soybean plants comprising an introgressed stacked trait improvement locus, a glyphosate and a dicamba resistance conferring transgene, and a cry1Ac insect resistance transgene are provided. In still other embodiments, soybean plants comprising at least one herbicide resistance transgene selected from the group consisting of a dicamba resistance conferring transgene, a glyphosate resistance conferring transgene, a 2,4-D resistance conferring transgene, and a glufosinate resistance conferring transgene and/or at least one transgene encoding a product that confers insect resistance selected from the group consisting of a dsRNA that inhibits a target gene of an insect pest, a patatin, a *Bacillus thuringiensis* insecticidal protein, a *Xenorhabdus* insecticidal protein, a *Photorhabdus* insecticidal protein, a *Bacillus laterosporous* insecticidal protein, a *Bacillus sphaericus* insecticidal protein, and a lignin are provided.

Methods of identifying a soybean plant that comprises a genotype associated with stacked transgenic trait improvement are thus provided. In certain embodiments, the methods can comprise detecting in a soybean plant an allele in at least one genetic locus associated with stacked transgenic trait improvement, where the genetic locus is in a linkage group L genomic region flanked by loci M0205928 (SEQ ID NO: 4) and BU765955 (SEQ ID NO: 12), and denoting that the plant comprises a genotype associated with stacked transgenic trait improvement. In certain embodiments, the methods can further comprise the step of selecting the denoted plant from a population of plants. In certain embodiments, the plant comprises at least two transgenes that contribute to the same trait. In certain embodiments, this same trait is selected from the group consisting of resistance to a single herbicide, resistance to an insect, resistance to a nematode, resistance to a fungal disease, resistance to an abiotic stress, an improvement in seed oil quantity, an improvement in seed oil quality, and intrinsic yield increases. In certain embodiments, the plant comprises at least two transgenes that contribute to different traits. In certain embodiments, this different trait is independently selected from the group consisting of resistance to one or more herbicide(s), resistance to one or more insect(s), resistance to one or more nematode(s), resistance to one or more fungal disease(s), resistance to one or more abiotic stress(es), one or more improvement(s) in seed oil quantity or quantities, one or more improvement(s) in seed oil quality or qualities, intrinsic yield increases, and combinations thereof. In certain embodiments, the soybean plant or progeny thereof is exposed to a dosage of an herbicide sufficient to cause a deleterious effect in a susceptible variety comprising the transgene conferring resistance to that herbicide but lacking the stacked transgenic trait improvement locus. In certain embodiments of any of the aforementioned methods, a plant that exhibits stacked transgenic trait improvement is selected. In certain embodiments of any of the aforementioned methods, a genotype associated with stacked transgenic trait improvement comprises at least one polymorphic allele of at least one marker in a first sub-region of the linkage group L region that is flanked by loci M0205928 (SEQ ID NO: 4) and M0129138 (SEQ ID NO: 6) and/or at least one polymorphic allele of at least one marker in a second sub-region of the linkage group L region that is flanked by loci BU551363 (SEQ ID NO: 9) and BU765955 (SEQ ID NO: 12) and/or at least one polymorphic allele of at least one marker in a third sub-region of the linkage group L region that is flanked by loci BU55345 (SEQ ID NO:7) and M0114388 (SEQ ID NO:8) is provided. In certain embodiments of any of the aforementioned methods, the genotype associated with stacked transgenic trait improvement comprises at least one polymorphic allele of at least one marker in the linkage group L region selected from the group consisting of a TT allele M0205350 (SEQ ID NO: 10), a TT allele of M0101742 (SEQ ID NO: 5), a CC allele of M0102027 (SEQ ID NO: 11), and an AA allele of NGMAX008197032 (SEQ ID NO:52).

Methods for obtaining a soybean plant comprising in its genome at least one stacked transgenic trait improvement locus are also provided. In certain embodiments, these methods can compromise the steps of: (a) genotyping a plurality of soybean plants with respect to at least one genetic locus in a linkage group L genomic region flanked by loci M0205928 (SEQ ID NO: 4) and BU765955 (SEQ ID NO: 12); and, (b) selecting a soybean plant comprising in its genome at least one genetic locus comprising a genotype associated with stacked transgenic trait improvement. In certain embodiments, the plant comprises at least two transgenes that contribute to the same trait. In certain embodiments, this same trait is selected from the group consisting of resistance to a single herbicide, resistance to an insect, resistance to a nematode, resistance to a fungal disease, resistance to an abiotic stress, an improvement in seed oil quantity, an improvement in seed oil quality, and intrinsic yield increases. In certain embodiments, the plant comprises at least two transgenes that contribute to different traits. In certain embodiments, this different trait is independently selected from the group consisting of resistance to one or more herbicide(s), resistance to one or more insect(s), resistance to one or more nematode(s), resistance to one or more fungal disease(s), resistance to one or more abiotic stress(es), one or more improvement(s) in seed oil quantity or quantities, one or more improvement(s) in seed oil quality or qualities, intrinsic yield increases, and combinations thereof. In certain embodiments of these methods, the genotype associated with stacked transgenic trait improvement comprises at least one polymorphic allele of at least one marker in a first sub-region of the linkage group L region flanked by loci M0205928 (SEQ ID NO: 4) and M0129138 (SEQ ID NO: 6) and/or at least one polymorphic allele of at least one marker in a second sub-region of the linkage group L region that is flanked by loci BU551363 (SEQ ID NO: 9) and BU765955 (SEQ ID NO: 12) and/or at least one polymorphic allele of at least one marker in a third sub-region of the linkage group L region that is flanked by loci BU55345 (SEQ ID NO:7) and M0114388 (SEQ ID NO:8). In certain embodiments of any of these aforementioned methods, the genotype associated with stacked transgenic trait improvement comprises at least one polymorphic allele of at least one marker in the first linkage group L region, the first sub-region, the second sub-region, the third sub-region, where the marker is selected from the group consisting of a TT allele M0205350 (SEQ ID NO: 10), a TT allele of M0101742 (SEQ ID NO: 5), a CC allele of M0102027 (SEQ ID NO: 11), and an AA allele of NGMAX008197032 (SEQ ID NO:52). In certain embodiments of these methods, the plurality of soybean plants comprises a population that is obtained by: i) crossing a parent plant comprising at least one stacked transgenic trait improvement locus with a parent plant lacking a stacked transgenic trait improvement locus; or, ii) obtaining seed or progeny from a parental plant segregating for at least one stacked transgenic trait improvement locus. In certain embodiments of any of the aforementioned methods, the methods can further comprise the step of assaying for the presence of at least one additional marker, where the additional marker is either linked or unlinked to the linkage group L genomic region. In certain embodiments of any of the aforementioned methods, the plurality of soybean plants, the soybean plant, and/or progeny thereof are exposed to a dosage of an herbicide sufficient to cause a deleterious effect in a susceptible variety comprising the transgene conferring resistance to that herbicide but lacking the stacked transgenic trait improvement locus. In certain embodiments of any of the aforementioned methods, a plant that exhibits stacked transgenic trait improvement is selected.

Methods for producing a soybean plant comprising in its genome at least one introgressed stacked transgenic trait improvement locus are also provided. In certain embodiments, these methods comprise the steps of: (a) crossing a first soybean plant with a stacked transgenic trait improvement locus with a second soybean plant lacking a stacked transgenic trait improvement locus in a first linkage group L genomic region flanked by loci M0205928 (SEQ ID NO: 4) and M0129138 (SEQ ID NO: 6) and/or at least one polymorphic allele of at least one marker in a second sub-region of the linkage group L region that is flanked by loci BU551363 (SEQ ID NO: 9) and BU765955 (SEQ ID NO: 12) and/or at least one polymorphic allele of at least one marker in a third sub-region of the linkage group L region that is flanked by loci BU55345 (SEQ ID NO:7) and M0114388 (SEQ ID NO:8) and at least one linked polymorphic locus not present in the first soybean plant to obtain a population segregating for the stacked transgenic trait improvement loci and the linked polymorphic locus; (b) detecting at least two polymorphic nucleic acids in at least one soybean plant from the population, where at least one of the polymorphic nucleic acids is located in the first linkage group L region and/or the second linkage group L region and where at least one of the polymorphic amino acids is a linked polymorphic locus not present in the first soybean plant; and (c) selecting a soybean plant comprising a genotype associated with stacked transgenic trait improvement and at least one linked marker found in the second soybean plant lacking the stacked transgenic trait improvement locus but not found in the first soybean plant, thereby obtaining a soybean plant comprising in its genome at least one introgressed stacked transgenic trait improvement locus. In certain embodiments, the first and/or second plant comprises at least two transgenes that contribute to the same trait. In certain embodiments, this same trait is selected from the group consisting of resistance to a single herbicide, resistance to an insect, resistance to a nematode, resistance to a fungal disease, resistance to an abiotic stress, an improvement in seed oil quantity, an improvement in seed oil quality, and intrinsic yield increases. In certain embodiments, the plant comprises at least two transgenes that contribute to different traits. In certain embodiments, this different trait is independently selected from the group consisting of resistance to one or more herbicide(s), resistance to one or more insect(s), resistance to one or more nematode(s), resistance to one or more fungal disease(s), resistance to one or more abiotic stress(es), one or more improvement(s) in seed oil quantity or quantities, one or more improvement(s) in seed oil quality or qualities, intrinsic yield increases, and combinations thereof. In certain embodiments of these methods, the population, the selected soybean plant, and/or progeny of selected soybean plant is exposed to a dosage of an herbicide sufficient to cause a deleterious effect in a susceptible variety comprising the transgene that confers resistance to the herbicide but lacking the stacked transgenic trait improvement locus. In certain embodiments of these methods, the polymorphic nucleic acid detected in step (b) is detected with at least one marker selected from the group consisting of M0205350 (SEQ ID NO: 10), M0101742 (SEQ ID NO: 5), M0102027 (SEQ ID NO: 11), and an AA allele of NGMAX008197032 (SEQ ID NO:52). In certain embodiments of these methods, the polymorphic nucleic acid detected in step (b) comprises a TT allele of M0205350 (SEQ ID NO: 10), a TT allele of M0101742 (SEQ ID NO: 5), a CC allele of M0102027 (SEQ ID NO: 11) and an AA allele of NGMAX008197032 (SEQ ID NO:52). In certain embodiments of these methods, the polymorphic nucleic acid detected in step (b) is detected with marker M0205350 (SEQ ID NO: 10), M0102027 (SEQ ID NO: 11) or NGMAX008197032 (SEQ ID NO: 52). In certain embodiments of these methods, the polymorphic nucleic acids are detected with marker M0101742 (SEQ ID NO: 5). In certain embodiments of these methods, the polymorphic nucleic acids are detected with marker NGMAX008197032 (SEQ ID NO:52). In certain embodiments of any of the aforementioned methods, the linked polymorphic locus is detected with a genotypic marker, a phenotypic marker, or both. In certain embodiments of these methods, the linked polymorphic locus is detected with a marker that is located within about 1000, 500, 100, 40, 20, 10, or 5 kilobases (Kb) of the stacked transgenic trait improvement locus. In certain embodiments of these methods, the linked polymorphic locus is detected with at least one marker selected from the group consisting of asmbl_11856 (SEQ ID NO: 1), TC122822 (SEQ ID NO: 2), BI967232 (SEQ ID NO: 3), M0205537 (SEQ ID NO: 15), M0202715 (SEQ ID NO: 16), M0206286 (SEQ ID NO: 17), M0206054 (SEQ ID NO: 18), and M0205375 (SEQ ID NO: 19).

Transgenic soybean plants comprising introgressed linkage group L regions comprising at least one polymorphic allele of at least one marker in a first sub-region of the linkage group L region that flanked by loci M0205928 (SEQ ID NO: 4) and M0129138 (SEQ ID NO: 6) and/or at least one polymorphic allele of at least one marker in a second sub-region of the linkage group L region that is flanked by loci BU551363 (SEQ ID NO: 9) and BU765955 (SEQ ID NO: 12) and/or at least one polymorphic allele of at least one marker in a third sub-region of the linkage group L region that is flanked by loci BU55345 (SEQ ID NO:7) and M0114388 (SEQ ID NO:8), where the polymorphic alleles are associated with a stacked transgenic trait improvement locus, and where the plant comprises: (a) at least two transgenes that contribute to the same trait; or, (b) at least two transgenes that contribute different traits. In certain embodiments, this same trait is selected from the group consisting of resistance to a single herbicide, resistance to an insect, resistance to a nematode, resistance to a fungal disease, resistance to an abiotic stress, an improvement in seed oil quantity, an improvement in seed oil quality, and intrinsic yield increases. In certain embodiments, this different trait is independently selected from the group consisting of resistance to one or more herbicide(s), resistance to one or more insect(s), resistance to one or more nematode(s), resistance to one or more fungal disease(s), resistance to one or more abiotic stress(es), one or more improvement(s) in seed oil quantity or quantities, one or more improvement(s) in seed oil quality or qualities, intrinsic yield increases, and combinations thereof. In certain embodiments, the polymorphic alleles comprise a TT allele of M0205350 (SEQ ID NO: 10), a TT allele of M0101742 (SEQ ID NO: 5), a CC allele of M0102027 (SEQ ID NO: 11), and an AA allele of NGMAX008197032 (SEQ ID NO:52). In certain embodiments, the transgenic plant exhibits a stacked transgenic trait improvement. In certain embodiments, the transgenic plant further comprises a transgene that confers resistance to glyphosate and exhibits reproductive tolerance to glyphosate. In certain embodiments of any one of the aforementioned methods, the plant further comprises at least one of a 2,4-D, glufosinate, bromoxynil, synthetic auxins other than 2,4-D, acetolactate synthase (ALS), acetyl CoA carboxylase (ACCase), hydroxyphenyl pyruvate dioxygenase (HPPD), or sulfonylurea herbicide resistance transgenes and/or at least one transgene selected from the group of transgenes conferring insect resistance, nematode resistance, fungal resistance, an improvement in seed oil quantity, an improvement in seed oil quality, abiotic stress resistance, and intrinsic yield increases.

Also provided herein are methods of identifying a soybean plant that comprises a genotype associated with stacked transgenic trait improvement, comprising: detecting in a soybean plant an allele in at least one genetic locus associated with stacked transgenic trait improvement, wherein the genetic locus is in a linkage group L genomic region flanked by loci M0205928 (SEQ ID NO: 4) and BU765955 (SEQ ID NO: 12), and denoting that the plant comprises a genotype associated with stacked transgenic trait improvement. In certain embodiments, the method further comprises the step of selecting the denoted plant from a population of plants and wherein the detection is performed either before or after the selection. In certain embodiments, the denoted plant comprises at least one transgene that confer resistance to an herbicide and is selected for improved tolerance to that herbicide. In certain embodiments, the selection comprises exposing the population of plants to a dosage of herbicide sufficient to cause a deleterious effect in a susceptible variety comprising the transgene that confers resistance to the herbicide. In certain embodiments: (i) the plants comprise an herbicide resistance transgene selected from the group consisting of a dicamba resistance conferring transgene, a glyphosate resistance conferring transgene, a 2,4-D resistance conferring transgene, and a glufosinate resistance conferring transgene; and (ii) the plants comprising the herbicide resistance transgene are exposed to a dosage of a corresponding herbicide selected from the group consisting of dicamba, glyphosate, glufosinate, and 2,4-D that is sufficient to cause a deleterious effect in a susceptible variety comprising the herbicide resistant transgene that confers resistance to the corresponding herbicide. In certain embodiments, the stacked transgenic trait improvement is independently selected from the group consisting of an improvement in transgene-mediated resistance to one or more herbicide(s), an improvement in transgene-mediated resistance to one or more insect(s), an improvement in transgene-mediated resistance to one or more nematode(s), an improvement in transgene-mediated resistance to one or more fungal disease(s), an improvement in transgene-mediated resistance to one or more abiotic stress(es), in one or more improvement(s) in transgene-mediated seed oil quantity trait(s), one or more improvement(s) in seed oil quality trait(s), an improvement in transgene-mediated intrinsic yield increases, and combinations thereof. In certain embodiments, the denoted plant comprises at least one herbicide resistance transgene and/or at least one insect resistance conferring transgene that encodes a *Bacillus thuringiensis* toxin. In certain embodiments, the denoted plant comprises at least one herbicide resistance transgene selected from the group consisting of a dicamba resistance conferring transgene. a glyphosate resistance conferring transgene, a 2,4-D resistance conferring transgene, and a glufosinate resistance conferring transgene and/or at least one transgene encoding a product that confers insect resistance selected from the group consisting of a dsRNA that inhibits a target gene of an insect pest, a patatin, a *Bacillus thuringiensis* insecticidal protein, a *Xenorhabdus* insecticidal protein, a *Photorhabdus* insecticidal protein, a *Bacillus laterosporous* insecticidal protein, a *Bacillus sphaericus* insecticidal protein, and a lignin. In certain embodiments of any of the preceding methods, the genotype associated with stacked transgenic trait improvement comprises at least one polymorphic allele of at least one marker in a first sub-region of the linkage group L region that is flanked by loci M0205928 (SEQ ID NO: 4) and M0129138 (SEQ ID NO: 6) and/or at least one polymorphic allele of at least one marker in a second sub-region of the linkage group L region that is flanked by loci BU551363 (SEQ ID NO: 9) and BU765955 (SEQ ID NO: 12) and/or at least one polymorphic allele of at least one marker in a third sub-region of the linkage group L region that is flanked by loci BU55345 (SEQ ID NO:7) and M0114388 (SEQ ID NO:8). In certain embodiments of any of the preceding methods, the genotype associated with stacked transgenic trait improvement comprises at least one polymorphic allele of at least one marker in the linkage group L region selected from the group consisting of a TT allele M0205350 (SEQ ID NO: 10), a TT allele of M0101742 (SEQ ID NO: 5), a CC allele of M0102027 (SEQ ID NO: 11), and an AA allele of NGMAX008197032 (SEQ ID NO:52).

Also provided are methods for obtaining a soybean plant comprising in its genome at least one stacked transgenic trait improvement locus, comprimising the steps of: genotyping a plurality of soybean plants with respect to at least one genetic locus in a linkage group L genomic region flanked by loci M0205928 (SEQ ID NO: 4) and BU765955 (SEQ ID NO: 12); and selecting a soybean plant comprising in its genome at least one genetic locus comprising a genotype associated with stacked transgenic trait improvement. In certain embodiments of the methods, the genotype associated with stacked transgenic trait improvement comprises at least one polymorphic allele of at least one marker in a first sub-region of the linkage group L region flanked by loci M0205928 (SEQ ID NO: 4) and M0129138 (SEQ ID NO: 6) and/or at least one polymorphic allele of at least one marker in a second sub-region of the linkage group L region that is flanked by loci BU551363 (SEQ ID NO: 9) and BU765955 (SEQ ID NO: 12) and/or at least one polymorphic allele of at least one marker in a third sub-region of the linkage group L region that is flanked by loci BU55345 (SEQ ID NO:7) and M0114388 (SEQ ID NO:8). In certain embodiments of any of the preceding methods, the genotype associated with stacked transgenic trait improvement comprises at least one polymorphic allele of at least one marker in the first linkage group L region, the first sub-region, or the second sub-region, wherein the marker is selected from the group consisting of a TT allele M0205350 (SEQ ID NO: 10), a TT allele of M0101742 (SEQ ID NO: 5), a CC allele of M0102027 (SEQ ID NO: 11), and an AA allele of NGMAX008197032 (SEQ ID NO:52). In certain embodiments of the methods, the plurality of soybean plants comprises a population that is obtained by: i) crossing a parent plant comprising at least one stacked transgenic trait improvement locus with a parent plant comprising at least one stacked transgenic trait sensitivity locus; or, ii) obtaining seed or progeny from a parental plant segregating for at least one stacked transgenic trait improvement locus. In certain embodiments of the methods, the population contains plants that comprise at least one transgene that confers resistance to an herbicide and the stacked transgenic trait improvement comprises improved tolerance to a corresponding herbicide. In certain embodiments of any of the preceding methods, the methods further comprise the step of assaying for the presence of at least one additional marker, wherein the additional marker is either linked or unlinked to the linkage group L genomic region. In certain embodiments of any of the preceding methods, the plurality of soybean plants, the soybean plant, and/or progeny thereof are exposed to a dosage of herbicide sufficient to cause a deleterious effect in a susceptible variety comprising the transgene that confers resistance to the herbicide. In certain embodiments of any of the preceding methods, a plant that exhibits dicamba tolerance and/or reproductive tolerance to glyphosate and/or glufosinate tolerance and/or 2,4-D tolerance is selected. In certain embodiments of any of the preceding methods, the stacked transgenic trait improvement is selected from the group consisting of an improvement in transgene-mediated resistance to one or more herbicide(s), an improvement in transgene-mediated resistance to one or more insect(s), an improvement in transgene-mediated resistance to one or more nematode(s), an improvement in transgene-mediated resistance to one or more fungal disease(s), an improvement in transgene-mediated resistance to one or more abiotic stress(es), in one or more improvement(s) in transgene-mediated seed oil quantity trait(s), one or more improvement(s) in seed oil quality trait(s), an improvement in transgene-mediated intrinsic yield increases, and combinations thereof.

Also provided herein are methods for producing a soybean plant comprising in its genome at least one introgressed stacked transgenic trait improvement locus comprising the steps of: crossing a first soybean plant with a stacked transgenic trait improvement locus with a second soybean plant comprising: a stacked transgenic trait sensitivity locus in a first linkage group L genomic region flanked by loci M0205928 (SEQ ID NO: 4) and M0129138 (SEQ ID NO: 6) and/or at least one polymorphic allele of at least one marker in a second sub-region of the linkage group L region that is flanked by loci BU551363 (SEQ ID NO: 9) and BU765955 (SEQ ID NO: 12) and/or at least one polymorphic allele of at least one marker in a third sub-region of the linkage group L region that is flanked by loci BU55345 (SEQ ID NO:7) and M0114388 (SEQ ID NO:8) and at least one linked polymorphic locus not present in the first soybean plant to obtain a population segregating for the stacked transgenic trait improvement loci and the linked polymorphic locus; detecting at least two polymorphic nucleic acids in at least one soybean plant from the population, wherein at least one of the polymorphic nucleic acids is located in the first linkage group L region and/or the second linkage group L region and at least one of the polymorphic amino acids is a linked polymorphic locus not present in the first soybean plant; and selecting a soybean plant comprising a genotype associated with stacked transgenic trait improvement and at least one linked marker found in the second soybean plant comprising a stacked transgenic trait sensitivity locus but not in the first soybean plant, thereby obtaining a soybean plant comprising in its genome at least one introgressed stacked transgenic trait improvement locus. In certain embodiments of the methods, at least one of the first or the second soybean plants comprises a transgene that confers resistance to an herbicide. In certain embodiments of the methods, the population, the selected soybean plant, and/or progeny of selected soybean plant is exposed to a dosage of herbicide sufficient to cause a deleterious effect in a susceptible variety comprising the transgene that confers resistance to a corresponding herbicide. In certain embodiments of the methods, the polymorphic nucleic acid detected in step (b) is detected with at least one marker selected from the group consisting of M0205350 (SEQ ID NO: 10), M0101742 (SEQ ID NO: 5), M0102027 (SEQ ID NO: 11), and NGMAX008197032 (SEQ ID NO:52). In certain embodiments of the methods, the polymorphic nucleic acid detected in step (b) comprises a TT allele of M0205350 (SEQ ID NO: 10), a TT allele of M0101742 (SEQ ID NO: 5), a CC allele of M0102027 (SEQ ID NO: 11), and an AA allele of NGMAX008197032 (SEQ ID NO:52). In certain embodiments of the methods, the polymorphic nucleic acid detected in step (b) is detected with marker M0205350 (SEQ ID NO: 10), M0102027 (SEQ ID NO: 11), or marker NGMAX008197032 (SEQ ID NO:52). In certain embodiments of the methods, the polymorphic nucleic acids are detected with marker M0101742 (SEQ ID NO: 5). In certain embodiments of any of the preceding methods, the linked polymorphic locus is detected with a genotypic marker, a phenotypic marker, or both. In certain embodiments, the linked polymorphic locus is detected with a marker that is located within about 1000, 500, 100, 40, 20, 10, or 5 kilobases (Kb) of the stacked transgenic trait improvement locus. In certain embodiments, the linked polymorphic locus is detected with at least one marker selected from the group consisting of asmbl_11856 (SEQ ID NO: 1), TC122822 (SEQ ID NO: 2), BI967232 (SEQ ID NO: 3), M0205537 (SEQ ID NO: 15), M0202715 (SEQ ID NO: 16), M0206286 (SEQ ID NO: 17), M0206054 (SEQ ID NO:18), and M0205375 (SEQ ID NO: 19).

Also provided are transgenic soybean plants comprising introgressed linkage group L regions comprising at least one polymorphic allele of at least one marker in a first sub-region of the linkage group L region that flanked by loci M0205928 (SEQ ID NO: 4) and M0129138 (SEQ ID NO: 6) and/or at least one polymorphic allele of at least one marker in a second sub-region of the linkage group L region that is flanked by loci BU551363 (SEQ ID NO: 9) and BU765955 (SEQ ID NO: 12) and/or at least one polymorphic allele of at least one marker in a third sub-region of the linkage group L region that is flanked by loci BU55345 (SEQ ID NO:7) and M0114388 (SEQ ID NO:8), wherein the polymorphic alleles are associated with stacked transgenic trait improvement and wherein the plant comprises at least one transgene. In certain embodiments, the transgene confers resistance to an herbicide. In certain embodiments, the polymorphic alleles comprise a TT allele of M0205350 (SEQ ID NO: 10), a TT allele of M0101742 (SEQ ID NO: 5), a CC allele of M0102027 (SEQ ID NO: 11), and an AA allele of NGMAX008197032 (SEQ ID NO:52). In certain embodiments of any of the preceding methods, the plant exhibits tolerance to at least one herbicide. In certain embodiments, the plant comprises: i) a transgene that confers resistance to glyphosate and exhibits reproductive tolerance to glyphosate; and/or (ii) a dicamba resistance conferring transgene and exhibits dicamba tolerance; and/or (iii) a glufosinate resistance conferring transgene and exhibits glufosinate tolerance; and/or (iv) a 2,4-D resistance conferring transgene and exhibits 2,4-D tolerance. In certain embodiments, the plant comprises at least one transgene conferring resistance to a herbicide selected from the group consisting of dicamba, 2,4-D, glufosinate, bromoxynil, synthetic auxins other than 2,4-D, acetolactate synthase (ALS), acetyl CoA carboxylase (ACCase), hydroxyphenyl pyruvate dioxygenase (HPPD), and a sulfonylurea herbicide and/or at least one transgene selected from the group of transgenes conferring insect resistance, nematode resistance, fungal resistance, an improvement in seed oil quantity, an improvement in seed oil quality, abiotic stress resistance, and intrinsic yield increases. In certain embodiments, the plant comprises at least one herbicide resistance transgene and/or at least one insect resistance conferring transgene that encodes a *Bacillus thuringiensis* toxin. In certain embodiments, the plant comprises at least one herbicide resistance transgene selected from the group consisting of a dicamba resistance conferring transgene a glyphosate resistance conferring transgene, a 2,4-D resistance conferring transgene, and a glufosinate resistance conferring transgene and/or at least one transgene encoding a product that confers insect resistance selected from the group consisting of a dsRNA that inhibits a target gene of an insect pest, a patatin, a *Bacillus thuringiensis* insecticidal protein, a *Xenorhabdus* insecticidal protein, a *Photorhabdus* insecticidal protein, a *Bacillus laterosporous* insecticidal protein, a *Bacillus sphaericus* insecticidal protein, and a lignin.

Also provided herein are methods of identifying a transgenic soybean plant that comprises a genotype associated with stacked transgenic trait improvement, the method comprising: (a) scoring at least one transgenic plant in a population of transgenic soybean plants that had been exposed to dicamba for dicamba tolerance, the plants having a transgene that confers resistance to dicamba; and, (b) selecting a transgenic plant that exhibits dicamba tolerance, thereby identifying a transgenic soybean plant that comprises a genotype associated with stacked transgenic trait improvement. In certain embodiments, the population is segregating for to at least one genetic locus in a linkage group L genomic region flanked by loci M0205928 (SEQ ID NO: 4) and BU765955 (SEQ ID NO: 12) that is associated with stacked transgenic trait improvement. In certain embodiments, the method further comprises genotyping the selected soybean plant with respect to at least one genetic locus in a linkage group L genomic region flanked by loci M0205928 (SEQ ID NO: 4) and BU765955 (SEQ ID NO: 12). In certain embodiments, the selected transgenic plant further comprises a transgene that confers resistance to glyphosate and the selected transgenic plant or progeny thereof is scored for reproductive tolerance to glyphosate following exposure to glyphosate. In certain embodiments of any of the preceding methods, the methods further comprise exposing the population of transgenic soybean plants to dicamba. In certain embodiments of any of the preceding methods, dicamba tolerance is scored by determining a reduction in malformation when compared to a dicamba sensitive transgenic plant that comprises the transgene that confers resistance to dicamba. In certain embodiments of any of the preceding methods, the stacked transgenic trait improvement is selected from the group consisting of an improvement in transgene-mediated resistance to one or more herbicide(s), an improvement in transgene-mediated resistance to one or more insect(s), an improvement in transgene-mediated resistance to one or more nematode(s), an improvement in transgene-mediated resistance to one or more fungal disease(s), an improvement in transgene-mediated resistance to one or more abiotic stress(es), in one or more improvement(s) in transgene-mediated seed oil quantity trait(s), one or more improvement(s) in seed oil quality trait(s), an improvement in transgene-mediated intrinsic yield increases, and combinations thereof. In certain embodiments of any of the preceding methods, the selected plant comprises at least one additional herbicide resistance transgene selected from the group consisting of a glyphosate resistance conferring transgene, a 2,4-D resistance conferring transgene, and a glufosinate resistance conferring transgene and/or at least transgene encoding a product that confers insect resistance selected from the group consisting of a dsRNA that inhibits a target gene of an insect pest, a patatin, a *Bacillus thuringiensis* insecticidal protein, a *Xenorhabdus* insecticidal protein, a *Photorhabdus* insecticidal protein, a *Bacillus laterosporous* insecticidal protein, a *Bacillus sphaericus* insecticidal protein, and a lignin.

Also provided herein are methods of identifying a transgenic soybean plant that comprises a genotype associated with stacked transgenic trait improvement, comprising: (a) scoring at least one plant in a population of transgenic soybean plants that had been exposed to glyphosate for reproductive tolerance to glyphosate, wherein the plants comprise a transgene that confers resistance to glyphosate; and, (b) selecting a transgenic plant that exhibits reproductive tolerance to glyphosate, thereby identifying a transgenic soybean plant that comprises a genotype associated with stacked transgenic trait improvement. In certain embodiments, the population is segregating for to at least one genetic locus in a linkage group L genomic region flanked by loci M0205928 (SEQ ID NO: 4) and BU765955 (SEQ ID NO: 12) that is associated with stacked transgenic trait improvement. In certain embodiments, the method further comprises genotyping the selected soybean plant with respect to at least one genetic locus in a linkage group L genomic region flanked by loci M0205928 (SEQ ID NO: 4) and BU765955 (SEQ ID NO: 12). In certain embodiments of any of the preceding methods, the selected transgenic plant further comprises a transgene that confers resistance to dicamba and the selected transgenic plant or progeny thereof is scored for tolerance to dicamba following exposure to dicamba. In certain embodiments of any of the preceding methods, the methods further comprise exposing the population of transgenic soybean plants to glyphosate. In certain embodiments of any of the preceding methods, glyphosate reproductive tolerance is scored by determining a reduction in sterility when compared to a transgenic plant that exhibits glyphosate reproductive sensitivity and comprises the transgene that confers resistance to glyphosate. In certain embodiments of any of the preceding methods, the stacked transgenic trait improvement is selected from the group consisting of an improvement in transgene-mediated resistance to one or more herbicide(s), an improvement in transgene-mediated resistance to one or more insect(s), an improvement in transgene-mediated resistance to one or more nematode(s), an improvement in transgene-mediated resistance to one or more fungal disease(s), an improvement in transgene-mediated resistance to one or more abiotic stress(es), in one or more improvement(s) in transgene-mediated seed oil quantity trait(s), one or more improvement(s) in seed oil quality trait(s), an improvement in transgene-mediated intrinsic yield increases, and combinations thereof. In certain embodiments of any of the preceding methods, the selected plant comprises at least one additional herbicide resistance transgene selected from the group consisting of a dicamba resistance conferring transgene, a 2,4-D resistance conferring transgene, and a glufosinate resistance conferring transgene and/or at least one transgene encoding a product that confers insect resistance selected from the group consisting of a dsRNA that inhibits a target gene of an insect pest, a patatin, a *Bacillus thuringiensis* insecticidal protein, a *Xenorhabdus* insecticidal protein, a *Photorhabdus* insecticidal protein, a *Bacillus laterosporous* insecticidal protein, a *Bacillus sphaericus* insecticidal protein, and a lignin.

Also provided are methods of obtaining a transgenic soybean plant that comprises a genotype associated with stacked transgenic trait improvement, the methods comprising: exposing a population of transgenic soybean plants to an herbicide, wherein the plants have a transgene that confers resistance to the herbicide; observing herbicide tolerance exhibited by one or more soybean plants following exposure to the herbicide; and, (c) selecting a transgenic plant that exhibits herbicide tolerance, thereby obtaining a transgenic soybean plant that comprises a genotype associated with stacked transgenic trait improvement. In certain embodiments, the population is segregating for to at least one genetic locus in a linkage group L genomic region flanked by loci M0205928 (SEQ ID NO: 4) and BU765955 (SEQ ID NO: 12) that is associated with stacked transgenic trait improvement. In certain embodiments, the method further comprises genotyping the selected soybean plant with respect to at least one genetic locus in a linkage group L genomic region flanked by loci M0205928 (SEQ ID NO: 4) and BU765955 (SEQ ID NO: 12). In certain embodiments of any of the preceding methods, the transgene that confers resistance to the herbicide is selected from the group consisting of a dicamba resistance conferring transgene, a glyphosate resistance conferring transgene, a 2,4-D resistance conferring transgene, and a glufosinate resistance conferring transgene and the plants are exposed to the corresponding herbicide. In certain embodiments of any of the preceding methods, the transgene confers resistance to glyphosate and the selected transgenic plant or progeny thereof is scored for reproductive tolerance to glyphosate following exposure to glyphosate. In certain embodiments of any of the preceeding methods, the transgene confers resistance to dicamba and the selected transgenic plant or progeny thereof are scored for dicamba tolerance.

Also provided herein are methods of identifying a transgenic soybean plant that comprises a genotype associated with reproductive tolerance to glyphosate, the method comprising: (a) scoring at least one transgenic plant in a population of transgenic soybean plants that had been exposed to dicamba for dicamba tolerance, the plants having a transgene that confers resistance to dicamba; and, (b) selecting a transgenic plant that exhibits dicamba tolerance, thereby identifying a transgenic soybean plant that comprises a genotype associated with reproductive tolerance to glyphosate. In certain embodiments of the methods, the population is segregating for to at least one genetic locus in a linkage group L genomic region flanked by loci M0205928 (SEQ ID NO: 4) and BU765955 (SEQ ID NO: 12) that is associated with dicamba tolerance. In certain embodiments of the methods, the methods further comprise genotyping the selected soybean plant with respect to at least one genetic locus in a linkage group L genomic region flanked by loci M0205928 (SEQ ID NO: 4) and BU765955 (SEQ ID NO: 12). In certain embodiments of any of the aforementioned methods, the selected transgenic plant further comprises a transgene that confers resistance to glyphosate and wherein the selected transgenic plant or progeny thereof is scored for reproductive tolerance to glyphosate following exposure to glyphosate. In certain embodiments of any of the aforementioned methods, the methods further comprise exposing the population of transgenic soybean plants to dicamba. In certain embodiments of any of the aforementioned methods, the dicamba tolerance is scored by determining a reduction in malformation when compared to a dicamba sensitive transgenic plant that comprises the transgene that confers resistance to dicamba.

Also provided herein are methods of identifying a transgenic soybean plant that comprises a genotype associated with tolerance to dicamba, comprising: (a) scoring at least one plant in a population of transgenic soybean plants that had been exposed to glyphosate for reproductive tolerance to glyphosate, wherein the plants comprise a transgene that confers resistance to glyphosate; and, (b) selecting a transgenic plant that exhibits reproductive tolerance to glyphosate, thereby identifying a transgenic soybean plant that comprises a genotype associated with dicamba tolerance. In certain embodiments of the methods, the population is segregating for to at least one genetic locus in a linkage group L genomic region flanked by loci M0205928 (SEQ ID NO: 4) and BU765955 (SEQ ID NO: 12) that is associated with dicamba tolerance. In certain embodiments of the methods, the method further comprises genotyping the selected soybean plant with respect to at least one genetic locus in a linkage group L genomic region flanked by loci M0205928 (SEQ ID NO: 4) and BU765955 (SEQ ID NO: 12). In certain embodiments of any of the aforementioned methods, the selected transgenic plant further comprises a transgene that confers resistance to dicamba and wherein the selected transgenic plant or progeny thereof is scored for tolerance to dicamba following exposure to dicamba. In certain embodiments of any of the aforementioned methods, the methods further comprise exposing the population of transgenic soybean plants to glyphosate. In certain embodiments of any of the aforementioned methods, the glyphosate reproductive tolerance is scored by determining a reduction in sterility when compared to a transgenic plant that exhibits glyphosate reproductive sensitivity and comprises the transgene that confers resistance to glyphosate.

Also provided herein are methods of obtaining a transgenic soybean plant that comprises a genotype associated with reproductive tolerance to glyphosate, the methods comprising: (a) exposing a population of transgenic soybean plants to dicamba, wherein the plants have a transgene that confers resistance to dicamba; (b) observing dicamba tolerance exhibited by one or more soybean plants following exposure to dicamba; and, (c) selecting a transgenic plant that exhibits dicamba tolerance, thereby obtaining a transgenic soybean plant that comprises a genotype associated with reproductive tolerance to glyphosate. In certain embodiments of the methods, the population is segregating for to at least one genetic locus in a linkage group L genomic region flanked by loci M0205928 (SEQ ID NO: 4) and BU765955 (SEQ ID NO: 12) that is associated with dicamba tolerance. In certain embodiments of the methods, the methods further comprise genotyping the selected soybean plant with respect to at least one genetic locus in a linkage group L genomic region flanked by loci M0205928 (SEQ ID NO: 4) and BU765955 (SEQ ID NO: 12). In certain embodiments of any of the aforementioned methods, the selected transgenic plant further comprises a transgene that confers resistance to glyphosate and the selected transgenic plant or progeny thereof is scored for reproductive tolerance to glyphosate following exposure to glyphosate. In certain embodiments of any of the aforementioned methods, the dicamba tolerance is scored by determining a reduction in malformation when compared to a dicamba sensitive transgenic plant that comprises the transgene that confers resistance to dicamba. Further areas of applicability will become apparent from the description provided herein. It should be understood that the description and specific examples are intended for purposes of illustration only and are not intended to limit the scope of the present disclosure.

is "Unfavorable Haplotype". The data show that presence of the favorable haplotype is associated with improved tolerance to dicamba.

Figure 2:
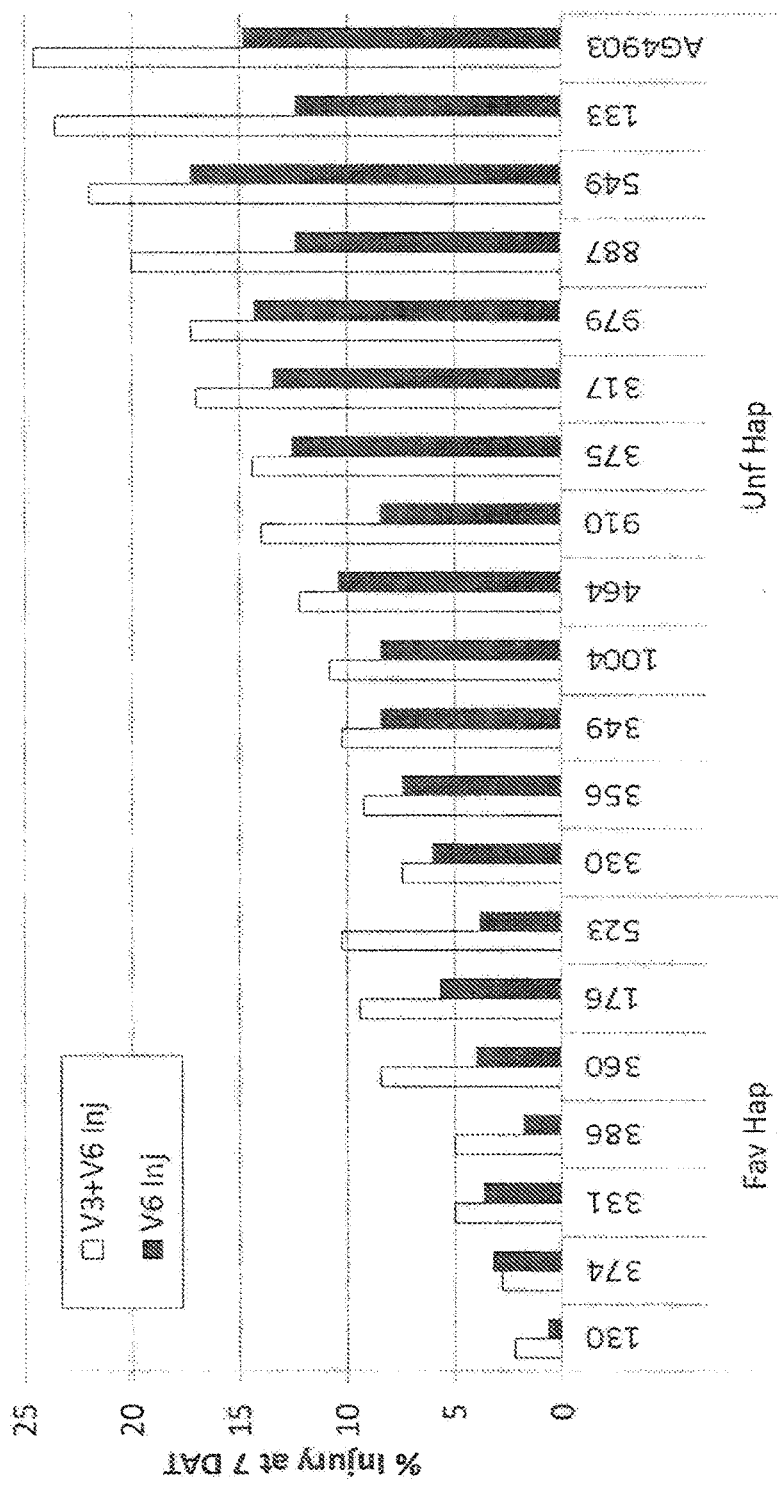

FIG. 2 shows a bar graph of the percent injury at 7 days after treatment with either a single treatment (V6 stage, solid bars) or two treatments (V3+V6 stages, open bars) of Dicamba (y-axis) for various favorable and unfavorable soybean plant haplotypes (x-axis) containing a dicamba resistance conferring transgene (x-axis). In the graph, "Fav Hap is "Favorable Haplotype" and "Unf Hap" is "Unfavorable Haplotype". The data show that favorable haplotypes can be selected with either a single treatment at the V6 stage or two treatments at the V3 and V6 stages.

DETAILED DESCRIPTION

Definitions

As used herein, an "allele" refers to one of two or more alternative forms of a genomic sequence at a given locus on a chromosome. When all the alleles present at a given locus on a chromosome are the same, that plant is homozygous at that locus. If the alleles present at a given locus on a chromosome differ, that plant is heterozygous at that locus.

As used herein, the term "denoting" when used in reference to a plant genotype refers to any method whereby a plant is indicated to have a certain genotype. Such indications of a certain genotype include, but are not limited to, any method where a plant is physically marked or tagged. Physical markings or tags that can be used include, but not limited to, a barcode, a radio-frequency identification (RFID), a label or the like. Indications of a certain genotype also include, but are not limited to, any entry into any type of written or electronic database whereby the plant's genotype is provided.

A "locus" is a position on a genomic sequence that is usually found by a point of reference; e.g., a short DNA sequence that is a gene, or part of a gene or intergenic region. A locus may refer to a nucleotide position at a reference point on a chromosome, such as a position from the end of the chromosome.

As used herein, "linkage group L" corresponds to the soybean linkage group L described in Choi, et al., Genetics. 2007 May; 176(1): 685-696. Linkage group L, as used herein, also corresponds to soybean chromosome 19 (as described on the World Wide Web at soybase.org/LG2Xsome.php). As used herein, "polymorphism" means the presence of one or more variations of a nucleic acid sequence at one or more loci in a population of at least two members. The variation can comprise but is not limited to one or more nucleotide base substitutions, the insertion of one or more nucleotides, a nucleotide sequence inversion, and/or the deletion of one or more nucleotides.

As used herein, the term "single nucleotide polymorphism," also referred to by the abbreviation "SNP," means a polymorphism at a single site wherein the polymorphism constitutes any or all of a single base pair change, an insertion of one or more base pairs, and/or a deletion of one or more base pairs.

As used herein, "marker" means a detectable characteristic that can be used to discriminate between organisms. Examples of such characteristics include, but are not limited to, genetic markers, biochemical markers, fermentation yield, fermentation efficiency, energy yield, secondary compounds, metabolites, morphological characteristics, and agronomic characteristics.

As used herein, "marker assay" means a method for detecting a polymorphism at a particular locus using a particular method. Marker assays thus include, but are not limited to, measurement of at least one phenotype (such as seed color, flower color, or other visually detectable trait as well as any biochemical trait), restriction fragment length polymorphism (RFLP), single base extension, electrophoresis, sequence alignment, allelic specific oligonucleotide hybridization (ASO), random amplified polymorphic DNA (RAPD), microarray-based polymorphism detection technologies, and the like.

As used herein, "genotype" means the genetic component of the phenotype and it can be indirectly characterized using markers or directly characterized by nucleic acid sequencing.

As used herein, the term "introgressed", when used in reference to a genetic locus, refers to a genetic locus that has been introduced into a new genetic background. Introgression of a genetic locus can thus be achieved through both plant breeding methods or by molecular genetic methods. Such molecular genetic methods include, but are not limited to, various plant transformation techniques and/or methods that provide for homologous recombination, non-homologous recombination, site-specific recombination, and/or genomic modifications that provide for locus substitution or locus conversion. In certain embodiments, introgression could thus be achieved by substitution of a dicamba intolerance locus with a corresponding dicamba tolerance locus or by conversion of a locus from a dicamba intolerance genotype to a dicamba tolerance genotype.

As used herein, "phenotype" means the detectable characteristics of a cell or organism which can be influenced by gene expression.

As used herein, "linkage" refers to relative frequency at which types of gametes are produced in a cross. For example, if locus A has genes "A" or "a" and locus B has genes "B" or "b" and a cross between parent I with AABB and parent B with aabb will produce four possible gametes where the genes are segregated into AB, Ab, aB and ab. The null expectation is that there will be independent equal segregation into each of the four possible genotypes, i.e. with no linkage ¼ of the gametes will of each genotype. Segregation of gametes into a genotypes differing from ¼ are attributed to linkage.

As used herein, the termed "linked", when used in the context of markers and/or genomic regions, means that the markers and/or genomic regions are located on the same linkage group or chromosome.

As used herein, a "nucleic acid molecule," be it a naturally occurring molecule or otherwise may be "substantially purified", if desired, referring to a molecule separated from substantially all other molecules normally associated with it in its native state. More preferably, a substantially purified molecule is the predominant species present in a preparation. A substantially purified molecule may be at least about 60% free, preferably at least about 75% free, more preferably at least about 90% free, and most preferably at least about 95% free from the other molecules (exclusive of solvent) present in the natural mixture. The term "substantially purified" is not intended to encompass molecules present in their native state.

As used herein, "quantitative trait locus (QTL)" means a locus that controls to some degree numerically representable traits that are usually continuously distributed. As used herein, the term "transgene" means nucleic acid molecules in the form of DNA, such as cDNA or genomic DNA, and RNA, such as mRNA or microRNA, which may be single or double stranded.

As used herein, the term "event", when used in the context of describing a transgenic plant, refers to a particular transformed plant line. In a typical transgenic breeding program, a transformation construct responsible for a trait is introduced into the genome via a transformation method. Numerous independent transformants (events) are usually generated for each construct. These events are evaluated to select those with superior performance.

As used herein, the term "soybean" means *Glycine max* and includes all plant varieties that can be bred with soybean, including wild soybean species. In certain embodiments, soybean plants from the species *Glycine max* and the subspecies *Glycine max* L. ssp. max or *Glycine max* ssp. *formosana* can be genotyped using the compositions and methods of the present invention. In an additional aspect, the soybean plant is from the species *Glycine soja*, otherwise known as wild soybean, can be genotyped using these compositions and methods. Alternatively, soybean germplasm derived from any of *Glycine max, Glycine max* L. ssp. max, *Glycine max* ssp. *Formosana*, and/or *Glycine soja* can be genotyped using compositions and methods provided herein.

As used herein, the term "bulk" refers to a method of managing a segregating population during inbreeding that involves growing the population in a bulk plot, harvesting the self-pollinated seed of plants in bulk, and using a sample of the bulk to plant the next generation.

As used herein, the phrase "transgene that confers tolerance to dicamba" refers to the ability of a transgene to provide a soybean plant capable of surviving exposure to dicamba at a rate of about 0.5 pounds of acid equivalent per acre of dicamba acid to about 1.5 pounds of acid equivalent per acre of dicamba acid applied at either pre-emergence and/or postemergence. Transgenic plants comprising a transgene that confers tolerance to dicamba can exhibit either a "dicamba tolerant" phenotype in certain soybean germplasms or a "dicamba sensitive" phenotype in other distinct soybean germplasms when exposed to dicamba.

As used herein, the phrase "dicamba intolerant" refers to undesirable phenotypic traits observed in certain soybean germplasms that comprise a transgene that confers resistance to dicamba after exposure to dicamba at a rate of about 0.5 pounds of acid equivalent per acre of dicamba acid to about 1.5 pounds of acid equivalent per acre of dicamba acid. Such undesirable phenotypic traits include, but are not limited to, pronounced bending/twisting of the main stem and petioles, necrosis of the upper nodes and petioles, and/or limitation of new growth.

As used herein, the phrase "dicamba tolerant" refers to either the absence or reduction of undesirable phenotypic traits observed after exposure to dicamba in "dicamba intolerant" soybean germplasms that comprise a transgene that confers resistance to dicamba.

As used herein, the term "comprising" means "including but not limited to".

As used herein, the terms "scoring" or "score", refer to any qualitative, semi-quantitive, or quantitive method for determining the presence, absence, and/or the partial presence or absence, of a phenotypic trait.

As used herein, the phrase "susceptible variety", when used in reference to herbicide tolerance in a soybean plant comprising a transgene that confers resistance to that herbicide, refers to a soybean variety that allele(s) of the stacked transgenic trait improvement locus that do not confer such stacked transgenic trait improvements. "Susceptible varieties' are also referred to herein as "sensitive varieties" in the context of herbicide tolerance in a soybean plant comprising a transgene that confers resistance to that herbicide.

As used herein, the phrase "corresponding herbicide", when used in reference to a transgene that confers herbicide resistance, refers to the herbicide that the transgene confers resistance to. Thus, a corresponding herbicide for a transgene that confers resistance to glyphosate, dicamba, 2,4-D, or glufosinate is respectively glyphosate, dicamba, 2,4-D, or glufosinate.

Description

In accordance with the present invention, Applicants have discovered genomic regions, associated markers, and associated methods for identifying and associating genotypes that effect the levels of dicamba tolerance observed in soybean plants comprising a transgene that confers resistance to dicamba. Dicamba (3, 6-dichloro-o-anisic acid) is a useful broad spectrum herbicide for controlling weeds. For example, in one embodiment, a method of the invention comprises screening a plurality of transgenic germplasm entries displaying a heritable variation for at least one transgene mediated dicamba resistance trait wherein the heritable variation is linked to at least one genotype; and associating at least one genotype from the transgenic germplasm entries to at least one dicamba tolerance trait. In another embodiment, a method of the invention comprises crossing at least two germplasm entries with a test germplasm entry for the evaluation of performance of at least one dicamba tolerance trait in order to determine preferred crossing schemes. The methods of the present invention can be used with traditional breeding techniques as described below to more efficiently screen and identify genotypes affecting a dicamba tolerance trait.

The use of markers to infer a phenotype of interest results in the economization of a breeding program by substituting costly, time-intensive phenotyping assays with genotyping assays. Further, breeding programs can be designed to explicitly drive the frequency of specific, favorable phenotypes by targeting particular genotypes (U.S. Pat. No. 6,399, 855). Fidelity of these associations may be monitored continuously to ensure maintained predictive ability and, thus, informed breeding decisions (US Patent Application 2005/0015827). In this case, costly, time-intensive phenotyping assays required for determining if a plant or plants contains a genomic region associated with a "dicamba tolerance" or "Dicamba intolerance" phenotype can be supplanted by genotypic assays that provide for identification of a plant or plants that contain the desired genomic region that confers dicamba tolerance.

A Genomic Region Associated with a Dicamba Tolerance Phenotype

Provided herewith is a soybean genomic region that is shown herein to be associated with a desirable dicamba tolerance phenotype when present in certain allelic forms and when combined with certain transgenic loci that confer dicamba tolerance.

A soybean genomic region provided that can be associated with a desirable dicamba tolerance phenotype when present in certain allelic forms is located on the telomere proximal end of the short arm of soybean linkage group L (chromosome 19). A series of markers useful in practicing the methods of this invention are provided herewith in Table 1. Additional markers useful in the practice of the invention are provided herewith in Table 2 of the Specification, which is incorporated herewith by reference in its entirety. Table 2 provides the Table 1 markers, additional nucleic acid markers or loci that have been disclosed in various databases, the relative positions of the markers on a physical map of linkage group L (soybean chromosome 19), and sources for the markers.

TABLE 1

Markers spanning a genomic region associated with a desirable dicamba tolerance phenotype

| Marker or Locus Name | SEQ ID NO: | Map Position [1] | Allelic form(s) Associated with Dicamba Tolerance [2] |
|---|---|---|---|
| asmbl_11856 | 1 | 16506 | |
| TC122822 | 2 | 32108 | |
| BI967232 | 3 | 66686 | |
| M0205928 | 4 | 92526 | |
| M0101742[3] | 5 | 112836 | TT[6] |
| M0129138 | 6 | 114013 | |
| BU551345 | 7 | 116147 | |
| M0114388 | 8 | 380897 | |
| BU551363 | 9 | 422447 | |
| M0205350[4] | 10 | 423935 | TT[7] |
| M0102027[5] | 11 | 466558 | CC[8] |
| BU765955 | 12 | 474316 | |
| M0093116 | 13 | 805580 | |
| M0129925 | 14 | 831128 | |
| M0205537 | 15 | 890254 | |
| M0202715 | 16 | 921431 | |
| M0206286 | 17 | 1209977 | |
| M0206054 | 18 | 1465354 | |
| M0205375 | 19 | 2009800 | |
| NGMAX008197032[9] | 52 | 314997 | AA[10] |

[1] The relative positions of the approximate middle position of the listed markers or loci based on nucleotide positions on a physical map of soybean linkage group L (chromosome 19) of Table 2 are provided where nucleotide position 0 (zero) is telomere proximal and nucleotide position 2009800 is centromere proximal. Polymorphic nucleotide bases are designated in the sequence listing provided herewith according to the WIPO Standard ST.25 (1998), Table 1, as follows: r = g or a (purine); y = t/u or c (pyrimidine); m = a or c; (amino); k = g or t/u (keto); s = g or c (strong interactions 3 H-bonds); w = a or t/u (weak interactions 2H-bonds); b = g or c or t/u (not a); d = a or g or t/u (not c); h = a or c or t/u (not g); v = a or g or c (not t, not u); and n = a or g or c or t/u (unknown, or other; any.)
[2] Both the maternal and paternal alleles of the single nucleotide polymorphisms that can be associated with a dicamba tolerance phenotype are shown.
[3] The identified polymorphic allele of marker M0101742 is located at nucleotide 1206 of SEQ ID NO: 5.
[4] The identified polymorphic allele of marker M0205350 is located at nucleotide 148 of SEQ ID NO: 10.
[5] The identified polymorphic allele of marker M0102027 is located at nucleotide 349 of SEQ ID NO: 11.
[6] The identified polymorphic allele of marker M0101742 "TT" can be associated with a dicamba tolerance phenotype when the identified polymorphic alleles of the other markers are: "TT" for M0205350 and, in certain embodiments, "CC" for M0102027.
[7] The identified polymorphic allele of marker M020350 "TT" can be associated with a dicamba tolerance phenotype when the identified polymorphic alleles of the other markers are: "TT" for M0101742 and, in certain embodiments, "CC" for M0102027.
[8] In certain embodiments, the identified polymorphic allele "CC" for marker M0102027 can be associated with a dicamba tolerance phenotype when the identified polymorphic alleles of the other markers are: "TT" for M0101742 and "TT" for M020350.
[9] The identified polymorphic allele of marker NGMAX008197032 is located at nucleotide 201 of SEQ ID NO: 52.
[10] In certain embodiments, the identified polymorphic allele of marker NGMAX008197032 "AA" can be associated with a dicamba tolerance phenotype when the identified polymorphic alleles of the other markers are: "TT" for M0205350 and, in certain embodiments, "CC" for M0102027, and "TT" for M0101742.

Also provided herein are sub-regions of the linkage group L region that is flanked by loci M0205928 (SEQ ID NO: 4) and BU765995 (SEQ ID NO: 12) that are associated with a dicamba tolerance phenotype. A first sub-region of the linkage group L region associated with a dicamba tolerance phenotype is flanked by loci M0205928 (SEQ ID NO: 4) and M0129138 (SEQ ID NO: 6). These loci flank a first sub-region that spans telomere proximal nucleotide 92334 to centromere proximal nucleotide 113494 in the physical map of linkage group L provided in Table 2 of the specification. Polymorphisms located in this first sub-region that are associated with a dicamba tolerance phenotype can be detected with markers that include, but are not limited to, M0101742 (SEQ ID NO: 5). A second sub-region of the linkage group L region associated with a dicamba tolerance phenotype is flanked by loci BU551363 (SEQ ID NO: 9) and BU765955 (SEQ ID NO: 12). These loci flank the second sub-region that spans telomere proximal nucleotide 422447 to centromere proximal nucleotide 474316 in the physical map of linkage group L provided in Table 2 of the specification. Polymorphisms located in this second sub-region that are associated with a dicamba tolerance phenotype can be detected with markers that include, but are not limited to, M0205350 (SEQ ID NO: 10) or M0102027 (SEQ ID NO: 11). A third sub-region of the linkage group L region associated with a dicamba tolerance phenotype is flanked by loci BU55345 (SEQ ID NO:7) and M0114388 (SEQ ID NO:8). These loci flank the second sub-region that spans telomere proximal nucleotide 115,956 to centromere proximal nucleotide 380,486 in the physical map of linkage group L provided in Table 2 of the specification. Polymorphisms located in this third sub-region that are associated with a dicamba tolerance phenotype can be detected with markers that include, but are not limited to, NGMAX008197032 (SEQ ID NO:52). In certain embodiments of invention, a polymorphism associated with a dicamba tolerant phenotype is detected in only one of these sub-regions. In other embodiments of the invention, at least one polymorphism associated with a dicamba tolerant phenotype is detected in any two of these sub-regions. Thus, a marker including, but not limited to, M0101742 (SEQ ID NO: 5) can be used either independently of, or in combination with, one or more markers selected from the group consisting of M0205350 (SEQ ID NO: 10) and/or M0102027 (SEQ ID NO: 11) to detect polymorphisms associated with a dicamba tolerance phenotype. In certain embodiments, a marker including, but not limited to, M0101742 (SEQ ID NO: 5) can be used either independently of, or in combination with, marker NGMAX008197032 (SEQ ID NO:52) to detect polymorphisms associated with a dicamba tolerance phenotype. In certain embodiments, a marker including, but not limited to, marker NGMAX008197032 (SEQ ID NO:52) can be used either independently of, or in combination with, one or more markers selected from the group consisting of M0205350 (SEQ ID NO: 10) and/or M0102027 (SEQ ID NO: 11) to detect polymorphisms associated with a dicamba tolerance phenotype. In certain embodiments, a polymorphism in the first sub-region is detected with marker M0101742 (SEQ ID NO: 5) and a polymorphism in the second sub-region is detected with markers M0205350 (SEQ ID NO: 10) and/or M0102027 (SEQ ID NO: 11). In certain embodiments, a polymorphism in the first sub-region is detected with marker M0101742 (SEQ ID NO: 5) and a polymorphism in the third sub-region is detected with marker NGMAX008197032 (SEQ ID NO: 52). In certain embodiments, the alleles of these markers associated with dicamba tolerance are a TT allele M0101742 (SEQ ID NO: 5), a TT allele of M0205350 (SEQ ID NO: 10), and, in certain embodiments, a CC allele of M0102027 (SEQ ID NO: 11), and an AA allele of NGMAX008197032 (SEQ ID NO:52).

Additional genetic markers can be used either in conjunction with the markers provided in Table 1 and/or Table 2 or independently of the markers provided in Table 1 and/or Table 2 to practice the methods of the instant invention. Publicly available marker databases from which useful markers can be obtained include, but are not limited to, the soybase.org website on the internet (World Wide Web) that is administered by the United States Agricultural Research Service, the United States Department of Agriculture, and Iowa State University. Additional soybean markers that can be used and that have been described in the literature include, but are not limited to, Hyten et al., BMC Genomics.

11:38, 2010; Choi et al., Genetics. 176(1):685-96, 2007; Yoon et al., Theor Appl Genet. 2007 March; 114(5):885-99; and Hyten et al. Crop Sci. 2010 50: 960-968. Given the provision herein of a genomic region on linkage group L (chromosome 19) delimited or flanked by the telomere proximal locus M0205928 (SEQ ID NO: 4) of Table 2 and the centromere proximal locus BU765955 (SEQ ID NO: 12) of Table 2 as well as an assortment of soybean germplasms exhibiting either a "dicamba intolerant" or "dicamba tolerant" phenotype, additional markers located either within or near this genomic region that are associated with these phenotypes can be obtained by merely typing the new markers in the various germplasms provided herewith. The genomic region on linkage group L (chromosome 19) delimited or flanked by the telomere proximal locus M0205928 (SEQ ID NO: 5) of Table 2 and the centromere proximal locus BU765955 (SEQ ID NO: 12) of Table 2 can also be mapped relative to markers provided in any publicly available or other soybean physical or genetic map to place this genetic locus on that map.

Identification of Plants Exhibiting the "Dicamba Intolerance" or "Dicamba Tolerance" Phenotype To observe the presence or absence of the "dicamba intolerance" or dicamba tolerance phenotypes, transgenic soybean plants comprising a transgene that confers resistance to dicamba are typically exposed in early to mid-vegetative growth stages to one or more high doses of dicamba. Typical doses of dicamba that can elicit a dicamba intolerance phenotype can range from about a 2-fold label application rate of a commercially available dicamba formulation to about a 3-fold label application rate of a commercially available dicamba formulation. In terms of acid equivalents of dicamba acid applied, typical doses of dicamba that can elicit a dicamba intolerance phenotype can range from an application rate of about 1.0 pounds of acid equivalent per acre of dicamba acid to about 1.5 pounds of acid equivalent per acre of dicamba acid when the indicated amounts of dicamba acid are provided in either a commercially available dicamba formulation or when the indicated amounts of dicamba acid is provided in a similar formulation suitable for application to dicamba-tolerant crops. Commercially available dicamba formulations that can be used include, but are not limited to, Clarity® (BASF, N.C., USA); Banvel®, Banvel M®, Banvel Banvel SGF®, or Vanquish® (Syngenta, Wilmington, Del., USA); or Rifle® (Loveland Products, Inc., Loveland, Colo., USA). In certain embodiments, the commercially available dicamba formulation used is Clarity®. In certain embodiments, doses of dicamba that can elicit a dicamba intolerance phenotype can range from about a 2 fold application rate of about 0.25 gallons per acre Clarity® to about a three fold application rate of about 0.375 gallons per acre per acre Clarity®.

The dicamba intolerance phenotype can be observed approximately a week after herbicide application in certain soybean varieties comprising the transgene that confers resistance to dicamba. Dicamba is typically applied during pre and post-emergent vegetative growth stages. In certain embodiments of these methods, dicamba can be applied in weekly intervals (i.e. once a week) for any of 2, 3, 4 or more successive weeks to score for the presence of the dicamba intolerance phenotype. In certain embodiments, soybean plants at about the V3 vegetative development stage are exposed to an initial dicamba spray followed by a subsequent spray at V6/R1. Genotypes provided herein are especially useful for providing dicamba tolerance to plants sprayed at the V6 stage. As discussed herein, the vegetative stages of soybean are as follows: VE (emergence), VC (cotyledon stage), V1 (first trifoliate leaf), V2 (second trifoliate leaf), V3 (third trifoliate leaf), V(n) (nth trifoliate leaf), and V6 (flowering will soon start). As discussed herein, the reproductive stages of soybean are as follows: R1 (beginning bloom), R2 (full bloom), R3 (beginning pod), R4 (full pod), R5 (beginning seed), R6 (full seed), R7 (beginning maturity) and R8 (full maturity). A description of the soybean vegetative and reproductive stages can be found on the world wide web (internet) at ag.ndsu.edu/pubs/plantsci/rowcrops/a1174/a1174 w.htm (North Dakota State University publication A-1174, June 1999, Reviewed and Reprinted August 2004).

A rating scale that evaluates the degree of dicamba intolerance can also be employed to identify "dicamba intolerant" and "dicamba tolerant" plants. An exemplary and non-limiting scale for evaluating the Dicamba intolerance phenotype is as follows, where a low number corresponds to a "dicamba tolerance" phenotype and the a high number correlates to a "dicamba intolerance" phenotype:

A rating of 1: Less than 10% of plants show malformation
A rating of 2: 10-50% of plants show malformation
A rating of 3: Greater than 50% of plants show malformation Identification of Plants Exhibiting Reproductive Tolerance to Glyphosate Phenotype To observe the presence or absence of reproductive tolerance to glyphosate phenotypes, transgenic soybean plants comprising a transgene that confers glyphosate resistance are typically exposed in mid- to late-vegetative growth stages to one or more high doses of glyphosate. Doses of glyphosate that can elicit a reproductive sensitivity phenotype are usually at least about twice the typical application rates of commercial glyphosate formulations that are used to provide weed control in transgenic, glyphosate resistant soybean plants. In terms of acid equivalents of glyphosate acid applied, typical doses of glyphosate that can elicit a reproductive sensitivity phenotype can range from an application rate of about 1.0 pounds of acid equivalent per acre (about 1.12 kilograms per hectare) of glyphosate acid to about 2.25 pounds of acid equivalent per acre (i.e. about 2.52 kilograms per hectare) of glyphosate acid when the indicated amounts of glyphosate acid are provided in either a commercially available glyphosate formulation or when the indicated amounts of glyphosate acid is provided in a similar formulation suitable for application to glyphosate-tolerant crops. Commercially available glyphosate formulations that can be used include, but are not limited to, Roundup Original MAX®, Roundup PowerMAX®, Roundup UltraMax®, or RoundUp WeatherMAX® (Monsanto Co., St. Louis, Mo., USA); Touchdown IQ® or Touchdown Total® (Syngenta, Wilmington, Del., USA); Glyphomax®, Glyphomax Plus®, or Glyphomax XRT® (Dow Agrosciences LLC, Indianapolis, Ind., USA). In certain embodiments, the commercially available glyphosate formulation used is RoundUp WeatherMAX®. In certain embodiments, doses of glyphosate that can elicit a reproductive sensitivity phenotype can range from about a 2 fold application rate of about 42.6 ounces per acre RoundUp WeatherMax® (1.68 kilograms per hectare) to about a three fold application rate of about 63.9 ounces per acre RoundUp WeatherMax® (i.e. about 2.52 kilograms per hectare).

The reproductive sensitivity phenotype can be observed at an appropriate stage of reproductive development after herbicide application in certain soybean varieties comprising the transgene that confers glyphosate resistance. Glyphosate is typically applied during vegetative growth stages, where applications in later vegetative growth stages can typically elicit reproductive sensitivity at lower application rates. In certain embodiments of these methods, glyphosate can be applied in weekly intervals (i.e. once a week) for any of 2, 3, 4 or more successive weeks to score for the presence of the reproductive sensitivity phenotype. In certain embodiments, soybean plants at about the V3 vegetative development stage are exposed to an initial glyphosate spray followed by a subsequent spray at the V6 vegetative stage. In certain embodiments, soybean plants at about the V6 vegetative development stage are exposed to a glyphosate spray. As discussed herein, the vegetative stages of soybean are as follows: VE (emergence), VC (cotyledon stage), V1 (first trifoliolate leaf), V2 (second trifoliolate leaf), V3 (third trifoliolate leaf), V(n) (nth trifoliolate leaf), and V6 (flowering will soon start). As discussed herein, the reproductive stages of soybean are as follows R1 (beginning bloom, first flower); R2 (full bloom, flower in top 2 nodes); R3 (beginning pod, 3/16" pod in top 4 nodes); R4 (full pod, 3/4" pod in top 4 nodes); R5 (1/8" seed in top 4 nodes); R6 (full size seed in top 4 nodes); R7 (beginning maturity, one mature pod); and, R8 (full maturity, 95% of pods on the plant are mature). A description of the soybean vegetative and reproductive stages can be found on the world wide web (internet) at ag.ndsu.edu/pubs/plantsci/rowcrops/a1174/a1174w.htm (North Dakota State University publication A-1174, June 1999, Reviewed and Reprinted August 2004). Expression of the reproductive sensitivity trait can also be influenced by temperature, where the trait in varieties that display the reproductive sensitivity phenotype is more pronounced following treatment at temperatures of about 32 degrees Celsius or more.

A rating scale that evaluates the degree of reproductive sensitivity can also be employed to identify "tolerant" and "sensitive" plants. An exemplary and non limiting scale for evaluating the reproductive sensitivity phenotype is as follows, where the low numbers correspond to a "glyphosate reproductive tolerance" phenotype and the high numbers correlate to a "glyphosate reproductive sensitivity" phenotype where sterility is monitored as follows:

A rating scale of 1: Less than 10% of plants show sterility (glyphosate reproductive tolerance)

A rating scale of 2: Less than 10-50% of plants show sterility

A rating scale 3: Greater than 50% of plants show sterility (glyphosate reproductive sensitivity)

Soybean plant sterility can be measured by a variety of methods that include, but are not limited to, determining pollen counts, seed yield per plant, seed yield per pod, and the like. Controls used to determine glyphosate reproductive sensitivity or tolerance of a given transgenic soybean test plant comprising a transgenic insertion event that confers glyphosate resistance in a certain genetic background (i.e. genotype) in comparison tests include, but are not limited to, (a) co-cultivated soybean plants comprising the same transgenic insertion event in a genetic background that provides for glyphosate reproductive sensitivity; and/or (b) co-cultivated soybean plants comprising the same transgenic insertion event in a genetic background that provides for glyphosate reproductive tolerance, where the test and control plants are sprayed with glyphosate. Additional controls used to determine glyphosate reproductive sensitivity or tolerance can also include, but are not limited to, co-cultivated soybean plants of the same genotypes (i.e. soybean plants that are isogenic with respect to both the transgenic insertion event and genetic background as either the test or control soybean lines) that are not sprayed with glyphosate.

Introgression of a Genomic Region Associated with a Dicamba Tolerance Phenotype

Also provided herewith is unique soybean germplasm comprising an introgressed genomic region that is associated with a dicamba tolerance phenotype and methods of obtaining the same. Marker-assisted introgression involves the transfer of a chromosomal region, defined by one or more markers, from one germplasm to a second germplasm. Offspring of a cross that contain the introgressed genomic region can be identified by the combination of markers characteristic of the desired introgressed genomic region from a first germplasm (i.e. such as a dicamba tolerance germplasm) and both linked and unlinked markers characteristic of the desired genetic background of a second germplasm (i.e. a dicamba intolerance germplasm). In addition to the markers provided herewith that identify alleles of genomic region that is associated with a dicamba tolerance phenotype, flanking markers that fall on both the telomere proximal end of the genomic region on linkage group L (chromosome 19) and the centromere proximal end of the linkage group L (chromosome 19) genomic region are also provided in Tables 1 and 2. Table 2 is provided at the end of the specification immediately before the claims. Such flanking markers are useful in a variety of breeding efforts that include, but are not limited to, introgression of the genomic region associated with a dicamba tolerance phenotype into a genetic background comprising markers associated with germplasm that ordinarily contains the allelic forms of the genomic region that is associated with a "Dicamba intolerance" phenotype. Telomere proximal flanking markers that can be used in these methods include, but are not limited to, asmbl_11856 (SEQ ID NO: 1), TC122822 (SEQ ID NO: 2), BI967232 (SEQ ID NO: 3), and/or polymorphisms in any of the loci listed in Table 2 of the Specification located between starting base 16426 (the telomere proximal base) of locus asmbl_11856 and starting base 92334 of locus M0205928 (SEQ ID NO: 4). Centromere proximal flanking markers that can be used in these methods include, but are not limited to, M0205537 (SEQ ID NO: 15), M0202715 (SEQ ID NO: 16), M0206286 (SEQ ID NO: 17), M0206054 (SEQ ID NO: 18) and M0205375 (SEQ ID NO: 19) and/or polymorphisms in any of the other loci listed in Table 2 that are centromere proximal to BU765955 (SEQ ID NO: 12). Soybean plants wherein the two subregions that are respectively flanked by loci M0205928 (SEQ ID NO: 4) and M0129138 (SEQ ID NO: 6 and by loci BU551363 (SEQ ID NO: 9) and BU765955 (SEQ ID NO: 12) are selectively introgressed can be obtained by using the BU551345 (SEQ ID NO: 7), SATT723, and/or M0114388 (SEQ ID NO: 8) markers, or by using any of the markers located between these two subregions that are provided in Table 2. Any of the aforementioned polymorphisms can be identified by sequencing loci from dicamba intolerant and dicamba tolerance germplasms. Additional markers located on linkage group L (chromosome 19) and other chromosomes are disclosed in US Patent Application Publication 20090208964. Publicly available marker databases from which additional useful markers located on linkage group L (chromosome 19) and other chromosomes can be obtained include, but are not limited to, the soybase.org website on the internet that is administered by the United States Agricultural Research Service, the United States Department of Agriculture, and Iowa State University. Soybean plants or germplasm comprising an introgressed genomic region that is associated with a dicamba tolerance phenotype wherein at least 10%, 25%, 50%, 75%, 90%, or 99% of the remain genomic sequences carry markers characteristic of soybean plants or germplasm that are otherwise or ordinarily comprise a genomic region associated with the Dicamba intolerance phenotype are thus provided.

Soybean Plants Comprising Genomic Region Associated with the Dicamba Intolerance and Dicamba Tolerance Phenotypes and Transgenes that Confer Resistance to Dicamba A non-limiting and exemplary list of soybean plants that comprise genomic regions associated with either a dicamba-intolerance or a dicamba tolerance phenotype are provided herewith in Table 3.

embodiments, the dicamba tolerant soybean plants can comprise a transgene encoding a dicamba-degrading dicamba monoxygenase (DMO) enzyme that catalyzes the conversion of herbicidal dicamba (3, 6-dichloro-o-anisic acid) to a non-toxic 3, 6-dichlorosalicylic acid. In certain embodiments, the dicamba-degrading dicamba monoxygenase (DMOw) comprise a DMO enzyme disclosed in U.S. Pat. Nos. 7,022,896, 7,105,724, and 7,812,224, each incorporated herein by reference in their entireties. Exemplary and non-limiting DMOw dicamba monooxygenase encoding

TABLE 3

Soybean varieties comprising a genomic region associated with a dicamba tolerance or dicamba intolerant phenotype.

| Branded Name [1] | Dicamba Phenotype | U.S. Pat. No. | Variety Name in Patent | ATCC Depository Accession Number [2] | Date of Patent Issue |
|---|---|---|---|---|---|
| AG3102 | Intolerant | 7,964,777 | 7629164 | PTA-10825 | Jun. 21, 2011 |
| AG3603 | Intolerant | 7,592,516 | D4328762 | PTA-9797 | Sep. 22, 2009 |
| AG4903 | | | | | |
| AG4907 | Intolerant | 7,687,685 | D5703684 | PTA-10153 | Mar. 30, 2010 |
| AG0803 | Tolerant | 7,498,489 | 4498438 | PTA-9064 | |
| AG3102 | Tolerant | 7,964,777 | 7629164 | PTA-10825 | Jun. 21, 2011 |
| AG3603 | Tolerant | 7,592,516 | D4328762 | PTA-9797 | Sep. 22, 2009 |
| BBL3606N0R | | | | | |
| BL3307M2-D0RL | | | | | |
| AG4903 | | | | | |
| AG4907 | Tolerant | 7,687,685 | D5703684 | PTA-10153 | Mar. 30, 2010 |
| 260744-14 | | | | | |
| AFL0506C0R | Tolerant | 7,723,583 | D5864369 | PTA-10719 | May 25, 2010 |
| AG0808 | Tolerant | 7,732,672 | D5142326 | PTA-10168 | Jun. 8, 2010 |
| 263619-24 | | | | | |
| 4065735-51 | | | | | |
| 5463213-25 | | | | | |
| AG1002 | Tolerant | 7,294,770 | 5826175 | PTA-8148 | Nov. 13, 2007 |
| AG1403 | Tolerant | 7,557,273 | 6943322 | PTA-9554 | Jul. 7, 2009 |
| AG1406 | Tolerant | 7,732,673 | D5232589 | PTA-10268 | Jun. 8, 2010 |
| CSR1920 | Tolerant | 7,728,199 | 7821295 | PTA-10519 | Jun. 1, 2010 |
| 15733-79-59 | | | | | |
| 5081541-27 | | | | | |
| 5464705-06 | | | | | |
| AG2110 | Tolerant | 7,678,965 | D5624834 | PTA-10134 | Mar. 16, 2010 |
| AG2606 | Tolerant | 7,622,644 | D4201139 | PTA-9749 | Nov. 24, 2009 |
| AG2909 | Tolerant | 7,999,153 | D5502014 | PTA-11081 | Aug. 16, 2011 |
| AG2921V | Tolerant | 7,390,940 | 4858197 | PTA-9072 | Jun. 24, 2008 |
| AG3021V | Tolerant | 7,572,958 | D4361423 | PTA-9801 | Aug. 11, 2009 |
| BOX2906H0R | | | | | |
| DFN3306B0R | Tolerant | 7,626,089 | D4311702 | PTA-9781 | Dec. 1, 2009 |
| CSRS4782N | Tolerant | 7,700,847 | D5898941 | PTA-10598 | Apr. 20, 2010 |
| GL4807A2-D0RN | Tolerant | 7,868,230 | D5523145 | PTA-11362 | Jan. 11, 2011 |

[1] Branded names of Asgrow ® (designated "AG") and DEKALB ® soybean varieties from Monsanto Co. 800 N. Lindbergh Blvd., St. Louis, MO, USA.
[2] Deposit numbers of seed available through the American Type Culture Collection (ATCC), 10801 University Blvd., Manassas, Va., USA, 20110-2209.
[3] Dicamba phenotype is the phenotype observed in the indicated germplasm containing a transgene that confers resistance to dicamba when exposed to dicamba.

Also provided herewith are additional soybean plants that comprising a genomic region associated with a dicamba intolerant or dicamba tolerance phenotype that are identified by use of the markers provided in Table 1 and/or Table 2 and/or methods provided herein. Any of the soybean plants identified in Table 3 or other soybean plants that are otherwise identified using the markers or methods provided herein can be used in methods that include, but are not limited to, methods of obtaining soybean plants with an introgressed dicamba tolerance locus, obtaining a soybean plant that exhibits a dicamba tolerance phenotype, or obtaining a soybean plant comprising in its genome a genetic region associated with a dicamba tolerance phenotype.

In certain embodiments, the soybean plants provided herein or used in the methods provided herein can comprise a transgene that confers resistance to dicamba. In certain nucleic acid and protein sequences are provided herewith as SEQ ID NO: 20 and SEQ ID NO: 21. In certain embodiments, the dicamba tolerant soybean plants can comprise a dicamba monoxygenase variant which exhibits improved catalytic parameters such as increased turnover number and/or a lower km for the substrate, improved catalysis at lower pH values, and/or improved catalysis at higher temperatures relative to an unaltered dicamba monooxygenase. In certain embodiments, the dicamba monoxygenase variant comprises a DMOc variant enzyme disclosed in U.S. Pat. No. 7,884,262, incorporated herein by reference in its entirety. Exemplary and non-limiting DMOc dicamba monooxygenase variant encoding nucleic acid and protein sequences are provided herewith as SEQ ID NO: 22 and SEQ ID NO: 23. In certain embodiments, a dicamba monooxygenase is operably linked to a chloroplast transit peptide (CTP). Operable linkage of certain CTPs to DMO is disclosed in U.S. Pat. No. 8,084,666, which is incorporated herein by reference in its entirety. In certain embodiments, it is contemplated that the soybean plants used herein can comprise one or more specific genomic insertion(s) of a dicamba tolerant transgene including, but not limited to, as those found in MON87708 soybean (deposited under ATCC accession number PTA-9670 and described in US Patent Application Publication Number 20110067134).

In certain embodiments, the soybean plants provided herein or used in the methods provided herein can comprise a transgene that confers tolerance to glyphosate. Transgenes that can confer tolerance to glyphosate include, but are not limited to, transgenes that encode glyphosate tolerant Class I EPSPS (5-enolpyruvylshikimate-3-phosphate synthases) enzymes or glyphosate tolerant Class II EPSPS (5-enolpyruvylshikimate-3-phosphate synthases) enzymes. Useful glyphosate tolerant EPSPS enzymes provided herein are disclosed in U.S. Pat. Nos. 6,803,501, RE39,247, 6,225,114, 5,188,642, and 4,971,908. In certain embodiments, the glyphosate tolerant soybean plants can comprise a transgene encoding a glyphosate oxidoreductase or other enzyme which degrades glyphosate. Glyphosate oxidoreductase enzymes had been described in U.S. Pat. No. 5,776,760 and US Reissue patent RE38,825. In certain embodiments the soybean plant can comprise a transgene encoding a glyphosate N-acetyltransferase gene that confers tolerance to glyphosate. In certain embodiments, the soybean plant can comprise a glyphosate n-acetyltransferase encoding transgene such as those described in U.S. Pat. No. 7,666,644. In still other embodiments, soybean plants comprising combinations of transgenes that confer glyphosate tolerance are provided. Soybean plants comprising both a glyphosate resistant EPSPS and a glyphosate N-acetyltransferase are also provided herewith. In certain embodiments, it is contemplated that the soybean plants used herein can comprise one or more specific genomic insertion(s) of a glyphosate tolerant transgene including, but not limited to, as those found in: i) MON89788 soybean (deposited under ATCC accession number PTA-6708 and described in US Patent Application Publication Number 20100099859), ii) GTS 40-3-2 soybean (Padgette et al., Crop Sci. 35: 1451-1461, 1995), iii) event 3560.4.3.5 soybean (seed deposited under ATCC accession number PTA-8287 and described in US Patent Publication 20090036308), or any combination of i (MON89788 soybean), ii (GTS 40-3-2 soybean), and iii (event 3560.4.3.5 soybean).

In certain embodiments, the gene that confers resistance to dicamba is a gene encoding a Dicamba monooxygenase (DMO). The DMO gene is a microbial gene that has been transformed into soybean and cotton to confer tolerance to the dicamba herbicide. The DMO protein expressed in the plants transformed with the DMO gene actively metabolizes dicamba to 3,6-dichloro salicylic acid (DCSA), which lacks herbicidal activity. In certain embodiments, Dicamba resistant (DR) soybeans can be crossed with "RoundUp Ready 2 Yield™" (RR2Y) soybeans to generate a stack (RR2Y×DR) which can confer resistance to both dicamba and glyphosate. It has been observed in certain germplasms that a herbicide traits (i.e. transgene conferred glyphosate and dicamba resistance)×germplasm interaction can result in increased sensitivity to dicamba (i.e. "dicamba intolerance") that may be commercially undesirable. In certain embodiments, favorable haplotypes are provided herein which are associated with robust tolerance to dicamba and glyphosate, and which are useful for selection of RR2Y×DR soybeans that do not exhibit dicamba intolerance.

In certain embodiments, it is contemplated that genotypic assays that provide for non-destructive identification of the plant or plants can be performed either in seed, the emergence stage, the "VC" stage (i.e. cotyledons unfolded), the V1 stage (appearance of first node and unifoliate leaves), the V2 stage (appearance of the first trifoliate leaf), and thereafter. In certain embodiments, non-destructive genotypic assays are performed in seed using apparati and associated methods as described in U.S. Pat. Nos. 6,959,617; 7,134,351; 7,454,989; 7,502,113; 7,591,101; 7,611,842; and 7,685,768, which are incorporated herein by reference in their entireties. In certain embodiments, non-destructive genotypic assays are performed in seed using apparati and associated methods as described in US Patent Application Publications 20100086963, 20090215060, and 20090025288, which are incorporated herein by reference in their entireties. Published U.S. Patent Applications US 2006/0042527, US 2006/0046244, US 2006/0046264, US 2006/0048247, US 2006/0048248, US 2007/0204366, and US 2007/0207485, which are incorporated herein by reference in their entirety, also disclose apparatus and systems for the automated sampling of seeds as well as methods of sampling, testing and bulking seeds. Thus, in a certain embodiments, any of the methods provided herein can comprise screening for markers in individual seeds of a population wherein only seed with at least one genotype of interest is advanced.

Soybean Plants Comprising a Genomic Region Associated with Stacked Transgenic Trait Improvement and Transgenes that Confer Resistance to Other Herbicides and/or Insects In certain embodiments, soybean plants comprising a genomic region associated with stacked transgenic trait improvement (or the dicamba tolerance phenotype) and at least one additional herbicide resistance transgene selected from the group consisting of a dicamba resistance conferring transgene, a 2,4-D resistance conferring transgene, and a glufosinate resistance conferring transgene and/or at least one transgene encoding a product that confers insect resistance selected from the group consisting of a dsRNA that inhibits a target gene of an insect pest, a patatin, a *Bacillus thuringiensis* insecticidal protein, a *Xenorhabdus* insecticidal protein, a *Photorhabdus* insecticidal protein, a *Bacillus laterosporous* insecticidal protein, a *Bacillus sphaericus* insecticidal protein, and a lignin are provided herein. Such transgenic trait improvements that can occur in plants comprising the genomic regions provided herein can be ascertained by comparing transgenic trait performance in varieties containing the genomic regions to the transgenic trait performance in other varieties lacking the genomic region. Such transgenic herbicide resistance trait improvements that can occur in plants comprising the genomic regions provided herein can include, but are not limited to, decreased phytotoxicity upon herbicide exposure in varieties containing the genomic regions conferring the improved transgenic trait performance and the corresponding herbicide resistance conferring transgene in comparison to other varieties lacking the genomic region and the corresponding herbicide resistance conferring transgene upon herbicide exposure. Various dsRNAs that inhibit a target gene of an insect pest are described in US Patent Application Publication Number 20120137387, which is specifically incorporated herein by reference in its entirety. A *Bacillus thuringiensis* insecticidal protein can be any of a number of insecticidal proteins including but not limited to a Cry1, a Cry3, a TIC851, a CryET70, a Cry22, a TIC901, a TIC1201, a TIC407, a TIC417, a binary insecticidal protein CryET33 and CryET34, a binary insecticidal protein CryET80 and CryET76, a binary insecticidal protein TIC100 and TIC101, a binary insecticidal protein PS149B1, a VIP insecticidal protein, a TIC900 or related protein, or combinations of the insecticidal proteins ET29 or ET37 with insecticidal proteins TIC810 or TIC812, and insecticidal chimeras of any of the preceding insecticidal proteins. A *Bacillus thuringiensis* insecticidal protein can be any of a number of insecticidal proteins including but not limited to a Cry1Aa, Cry1Ab, Cry1Ac, Cry1Ad, Cry1Ae, Cry1Ba, Cry1Bb, Cry1Ca, Cry1Cb, Cry1Da, Cry1db, Cry1Ea, Cry1Eb, Cry1Fa, Cry1Fb, Cry1Ga, Cry1Ha, Cry2Aa, Cry2Ab, Cry1Ja, Cry1Ka, Cry11Aa, Cry11Ab, Cry12Aa, Cry3Ba, Cry3Bb, Cry3C, Cry4a, Cry4Ba, Cry5a, Cry5Ab, Cry6Aa, Cry6Ba, Cry7Aa, Cry7Ab, Cry8Aa, Cry8Ba, Cry8Ca, Cry9Aa, Cry9Ba, Cry9Ca, Cry10Aa, Cry11Aa, Cry12Aa, Cry13Aa, Cry14Aa, Cry15Aa, Cyt1Aa, and Cyt2Aa protein or an insecticidal chimeras thereof. Insecticidal chimeras of certain *Bacillus thuringiensis* insecticidal proteins include, but are not limited to, Cry1A/F and other chimeras disclosed in US Patent Application Publication No. 20090143298. Such transgenic insect resistance trait improvements that can occur in plants comprising the genomic regions provided herein can include, but are not limited to, decreased insect-mediated plant damage, or increased insect death, inhibition, stunting, or cessation of insect feeding in varieties containing the genomic regions that confer the transgenic trait performance in comparison to other varieties lacking the genomic region.

Molecular Assisted Breeding Techniques

Genetic markers that can be used in the practice of the instant invention include, but are not limited to, are Restriction Fragment Length Polymorphisms (RFLP), Amplified Fragment Length Polymorphisms (AFLP), Simple Sequence Repeats (SSR), Single Nucleotide Polymorphisms (SNP), Insertion or Deletion Polymorphisms (Indels), Variable Number Tandem Repeats (VNTR), and Random Amplified Polymorphic DNA (RAPD), and others known to those skilled in the art. Marker discovery and development in crops provides the initial framework for applications to marker-assisted breeding activities (US Patent Applications 2005/0204780, 2005/0216545, 2005/0218305, and 2006/00504538). The resulting "genetic map" is the representation of the relative position of characterized loci (DNA markers or any other locus for which alleles can be identified) along the chromosomes. The measure of distance on this map is relative to the frequency of crossover events between sister chromatids at meiosis.

As a set, polymorphic markers serve as a useful tool for fingerprinting plants to inform the degree of identity of lines or varieties (U.S. Pat. No. 6,207,367). These markers form the basis for determining associations with phenotype and can be used to drive genetic gain. The implementation of marker-assisted selection is dependent on the ability to detect underlying genetic differences between individuals.

Certain genetic markers for use in the present invention include "dominant" or "codominant" markers. "Codominant markers" reveal the presence of two or more alleles (two per diploid individual). "Dominant markers" reveal the presence of only a single allele. The presence of the dominant marker phenotype (e.g., a band of DNA) is an indication that one allele is present in either the homozygous or heterozygous condition. The absence of the dominant marker phenotype (e.g., absence of a DNA band) is merely evidence that "some other" undefined allele is present. In the case of populations where individuals are predominantly homozygous and loci are predominantly dimorphic, dominant and codominant markers can be equally valuable. As populations become more heterozygous and multiallelic, codominant markers often become more informative of the genotype than dominant markers.

In another embodiment, markers that include, but are not limited to, single sequence repeat markers (SSR), AFLP markers, RFLP markers, RAPD markers, phenotypic markers, isozyme markers, single nucleotide polymorphisms (SNPs), insertions or deletions (Indels), single feature polymorphisms (SFPs, for example, as described in Borevitz et al. 2003 Gen. Res. 13:513-523), microarray transcription profiles, DNA-derived sequences, and RNA-derived sequences that are genetically linked to or correlated with dicamba tolerance loci, regions flanking dicamba tolerance loci, regions linked to dicamba tolerance loci, and/or regions that are unlinked to dicamba tolerance loci can be used in certain embodiments of the instant invention.

In one embodiment, nucleic acid-based analyses for determining the presence or absence of the genetic polymorphism (i.e. for genotyping) can be used for the selection of seeds in a breeding population. A wide variety of genetic markers for the analysis of genetic polymorphisms are available and known to those of skill in the art. The analysis may be used to select for genes, portions of genes, QTL, alleles, or genomic regions (Genotypes) that comprise or are linked to a genetic marker that is linked to or correlated with dicamba tolerance loci, regions flanking dicamba tolerance loci, regions linked to dicamba tolerance loci, and/or regions that are unlinked to dicamba tolerance loci can be used in certain embodiments of the instant invention.

Nucleic acid analysis methods provided herein include, but are not limited to, PCR-based detection methods (for example, TaqMan™ assays), microarray methods, mass spectrometry-based methods and/or nucleic acid sequencing methods. In one embodiment, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

A method of achieving such amplification employs the polymerase chain reaction (PCR) (Mullis et al. 1986 Cold Spring Harbor Symp. Quant. Biol. 51:263-273; European Patent 50,424; European Patent 84,796; European Patent 258,017; European Patent 237,362; European Patent 201,184; U.S. Pat. Nos. 4,683,202; 4,582,788; and 4,683,194), using primer pairs that are capable of hybridizing to the proximal sequences that define a polymorphism in its double-stranded form.

Methods for typing DNA based on mass spectrometry can also be used. Such methods are disclosed in U.S. Pat. Nos. 6,613,509 and 6,503,710, and references found therein. Polymorphisms in DNA sequences can be detected or typed by a variety of effective methods well known in the art including, but not limited to, those disclosed in U.S. Pat. Nos. 5,468,613, 5,217,863; 5,210,015; 5,876,930; 6,030,787; 6,004,744; 6,013,431; 5,595,890; 5,762,876; 5,945,283; 5,468,613; 6,090,558; 5,800,944; 5,616,464; 7,312,039; 7,238,476; 7,297,485; 7,282,355; 7,270,981 and 7,250,252 all of which are incorporated herein by reference in their entireties. However, the compositions and methods of the present invention can be used in conjunction with any polymorphism typing method to type polymorphisms in genomic DNA samples. These genomic DNA samples used include but are not limited to genomic DNA isolated directly from a plant, cloned genomic DNA, or amplified genomic DNA.

For instance, polymorphisms in DNA sequences can be detected by hybridization to allele-specific oligonucleotide (ASO) probes as disclosed in U.S. Pat. Nos. 5,468,613 and 5,217,863. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe.

Target nucleic acid sequence can also be detected by probe ligation methods as disclosed in U.S. Pat. No. 5,800,944 where sequence of interest is amplified and hybridized to probes followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz et al., Genome Res. 13:513-523 (2003); Cui et al., Bioinformatics 21:3852-3858 (2005). On any one microarray, it is expected there will be a plurality of target sequences, which may represent genes and/or noncoding regions wherein each target sequence is represented by a series of overlapping oligonucleotides, rather than by a single probe. This platform provides for high throughput screening a plurality of polymorphisms. A single-feature polymorphism (SFP) is a polymorphism detected by a single probe in an oligonucleotide array, wherein a feature is a probe in the array. Typing of target sequences by microarray-based methods is disclosed in U.S. Pat. Nos. 6,799,122; 6,913,879; and 6,996,476.

Target nucleic acid sequence can also be detected by probe linking methods as disclosed in U.S. Pat. No. 5,616,464, employing at least one pair of probes having sequences homologous to adjacent portions of the target nucleic acid sequence and having side chains which non-covalently bind to form a stem upon base pairing of the probes to the target nucleic acid sequence. At least one of the side chains has a photoactivatable group which can form a covalent cross-link with the other side chain member of the stem.

Other methods for detecting SNPs and Indels include single base extension (SBE) methods. Examples of SBE methods include, but are not limited to, those disclosed in U.S. Pat. Nos. 6,004,744; 6,013,431; 5,595,890; 5,762,876; and 5,945,283. SBE methods are based on extension of a nucleotide primer that is adjacent to a polymorphism to incorporate a detectable nucleotide residue upon extension of the primer. In certain embodiments, the SBE method uses three synthetic oligonucleotides. Two of the oligonucleotides serve as PCR primers and are complementary to sequence of the locus of genomic DNA which flanks a region containing the polymorphism to be assayed. Following amplification of the region of the genome containing the polymorphism, the PCR product is mixed with the third oligonucleotide (called an extension primer) which is designed to hybridize to the amplified DNA adjacent to the polymorphism in the presence of DNA polymerase and two differentially labeled dideoxynucleosidetriphosphates. If the polymorphism is present on the template, one of the labeled dideoxynucleosidetriphosphates can be added to the primer in a single base chain extension. The allele present is then inferred by determining which of the two differential labels was added to the extension primer. Homozygous samples will result in only one of the two labeled bases being incorporated and thus only one of the two labels will be detected. Heterozygous samples have both alleles present, and will thus direct incorporation of both labels (into different molecules of the extension primer) and thus both labels will be detected.

In another method for detecting polymorphisms, SNPs and Indels can be detected by methods disclosed in U.S. Pat. Nos. 5,210,015; 5,876,930; and 6,030,787 in which an oligonucleotide probe having a 5' fluorescent reporter dye and a 3' quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5'→3' exonuclease activity cleaves the probe and separates the reporter dye from the quencher dye resulting in increased fluorescence of the reporter.

In another embodiment, the locus or loci of interest can be directly sequenced using nucleic acid sequencing technologies. Methods for nucleic acid sequencing are known in the art and include technologies provided by 454 Life Sciences (Branford, Conn.), Agencourt Bioscience (Beverly, Mass.), Applied Biosystems (Foster City, Calif.), LI-COR Biosciences (Lincoln, Nebr.), NimbleGen Systems (Madison, Wis.), Illumina (San Diego, Calif.), and VisiGen Biotechnologies (Houston, Tex.). Such nucleic acid sequencing technologies comprise formats such as parallel bead arrays, sequencing by ligation, capillary electrophoresis, electronic microchips, "biochips," microarrays, parallel microchips, and single-molecule arrays, as reviewed by R. F. Service Science 2006 311:1544-1546.

The markers to be used in the methods of the present invention should preferably be diagnostic of origin in order for inferences to be made about subsequent populations. Experience to date suggests that SNP markers may be ideal for mapping because the likelihood that a particular SNP allele is derived from independent origins in the extant populations of a particular species is very low. As such, SNP markers appear to be useful for tracking and assisting introgression of QTLs, particularly in the case of Genotypes.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Marker-assisted backcrossing (MABC) is a common breeding methodology to transfer a gene of interest into a desired recurrent parent. MABC was used to transfer both the dicamba resistance (DMO) transgene (U.S. Patent Appl. US20110067134) and the glyphosate resistant RoundUp Ready 2 Yield™ (RR2Y) CP4 genes (U.S. Pat. No. 7,632, 985) into several recurrent parents. The process involved making three backcrosses to the recurrent parent and using genome wide markers to target the recovery of 95% or greater of the recurrent parent genome. In this process, markers were used to confirm the presence of the DMO and RR2Y CP4 genes and the absence of the RR1 CP4 gene. The haplotype at the dicamba tolerance locus for each recurrent parent was known.

Observations on MABC lines whose recurrent parents contained different haplotypes were made. For each MABC, there were several variants, with each variant tracing to a unique BC3F1 plant. The MABC lines were grown in spray trials at two locations throughout the United States with two replications at each location. Each line was planted in a paired, twelve foot plot. Each plot was sprayed at V3 with 0.75 lb a.e./acre of glyphosate and 1.0 lb a.e./acre dicamba followed by the same treatment at V6. Malformation was measured as the percentage of plants within a plot that were malformed. For each MABC, the data were averaged across variants, replications, and locations to place into one the following categories:

1. No malformation: No severe malformation detected
2. Malformation: >20% severe malformation The data are presented in Table 4. The 6 MABC lines with a CCAATT or TTAATT haplotype all showed malformation whereas the 25 lines with the TTTTCC haplotype showed no malformation. These observations indicated that the presence of certain haplotypes at the dicamba tolerance locus in lines containing the DMO and RR2Y CP4 transgenes leads to malformation following dicamba treatment.

Example 2: Haplotypes Associated with a Malformation and Sterility Phenotypes for MG 6 and 7 BC2F3:4 Populations Upon Herbicide Application The effect of different haplotypes on response to dicamba and glyphosate were evaluated by comparing MG6-7 BC2F3:4 lines that contained a CP4 transgene that confers tolerance to glyphosate and a DMO transgene that confers tolerance to dicamba. The recurrent parent of the population was RP1 that had the CCAACC haplotype for markers NS0101742, NS0205350, and NS0102027 markers, respectively. The donor parent of the population was DP1 that had a TTTTCC haplotype. During the breeding process, the haplotype for each line at the dicamba tolerance locus was not known. Markers were used to select for the absence of the RR1 CP4 gene, and for the presence of the RR2Y CP4 gene and the Dicamba resistance DMO gene. Table 5 describes the breeding history for this material.

TABLE 5

Breeding History for Plant Material in Example 2.

| Gen. | Season | Year | Location | Breeding Activity |
|---|---|---|---|---|
| Cross | Winter | 2007 | Isabella, Puerto Rico | Cross |
| F1 | Summer | 2008 | Isabella, Puerto Rico | Backcross |
| BC1F1 | Winter | 2008 | Isabella, Puerto Rico | Backcross |
| BC2F1 | Summer | 2009 | Isabella, Puerto Rico | Bulk |
| BC2F2 | Winter | 2009 | Isabella, Puerto Rico | Bulk |
| BC2F3 | Summer | 2010 | Mount Olive, NC | Single plant selection |
| BC2F4 | Summer | 2011 | Mount Olive, NC | Progeny row |

TABLE 4

Recurrent Parent Haplotypes and Malformation Phenotypes in Response to Dicamba Application.

| Recurrent Parent | Number of Observations | MG | M0101742 | M0205350 | M0102027 | Response to Dicamba |
|---|---|---|---|---|---|---|
| AG3102 | 24 | 3 | CC | AA | TT | Malformation |
| AG3603 | 30 | 3 | CC | AA | TT | Malformation |
| BBL3606N0R | 30 | 3 | CC | AA | TT | Malformation |
| BL3307M2-D0RL | 30 | 3 | CC | AA | TT | Malformation |
| AG4903 | 36 | 4 | TT | AA | TT | Malformation |
| AG4907 | 36 | 4 | CC | AA | TT | Malformation |
| 260744-14 | 24 | 0 | TT | TT | CC | No Malformation |
| AFL0506C0R | 24 | 0 | TT | TT | CC | No Malformation |
| AG0803 | 24 | 0 | TT | TT | CC | No Malformation |
| AG0808 | 24 | 0 | TT | TT | CC | No Malformation |
| 263619-24 | 24 | 1 | TT | TT | CC | No Malformation |
| 4065735-51 | 24 | 1 | TT | TT | CC | No Malformation |
| 5463213-25 | 36 | 1 | TT | TT | CC | No Malformation |
| AG1002 | 24 | 1 | TT | TT | CC | No Malformation |
| AG1403 | 24 | 1 | TT | TT | CC | No Malformation |
| AG1406 | 24 | 1 | TT | TT | CC | No Malformation |
| CSR1920 | 36 | 1 | TT | TT | CC | No Malformation |
| 15733-79-59 | 30 | 2 | TT | TT | CC | No Malformation |
| 5081541-27 | 12 | 2 | TT | TT | CC | No Malformation |
| 5464705-06 | 30 | 2 | TT | TT | CC | No Malformation |
| AG2110 | 36 | 2 | TT | TT | CC | No Malformation |
| AG2606 | 29 | 2 | TT | TT | CC | No Malformation |
| AG2909 | 30 | 2 | TT | TT | CC | No Malformation |
| AG2921V | 30 | 2 | TT | TT | CC | No Malformation |
| AG3021V | 30 | 3 | TT | TT | CC | No Malformation |
| AG3803 | 30 | 3 | TT | TT | CC | No Malformation |
| BOX2906H0R | 30 | 3 | TT | TT | CC | No Malformation |
| AG3803 | 30 | 3 | TT | TT | CC | No Malformation |
| DFN3306B0R | 24 | 3 | TT | TT | CC | No Malformation |
| CSRS4782N | 36 | 4 | TT | TT | CC | No Malformation |
| GL4807A2-D0RN | 36 | 4 | TT | TT | CC | No Malformation |

A total of 360 BC2F3:4 lines were grown in Mount Olive, N.C. in 2011. The lines were grown in a single four foot rows with one replication. The lines were sprayed with 0.75 lb a.e./acre of glyphosate at V3 plant stage followed by the same rate of glyphosate at V6 plant stage plus 0.5 lb a.e./acre of dicamba.

Rating Scales:
Malformation:
A rating of 1: Less than 10% of plants show malformation
A rating of 2: 10-50% of plants show malformation
A rating of 3: Greater than 50% of plants show malformation
Sterility:
A rating of 1: Less than 10% of plants show sterility
A rating of 2: 10-50% of plants show sterility
A rating of 3: Greater than 50% of plants show sterility Table 6 shows the distribution of lines across the different rating classes.

TABLE 6

Malformation and Sterility Ratings for Soybean Populations.

| Sterility Rating | Malformation Rating | | |
|---|---|---|---|
| | 1 | 2 | 3 |
| | Number of lines per rating class | | |
| 1 | 154 | 18 | 3 |
| 2 | 58 | 61 | 52 |
| 3 | 2 | 2 | 10 |

The 51 lines that were rated "1" for malformation and "1" for sterility and the 62 lines that were rated "3" for malformation and "2" or "3" for sterility were genotyped for the three dicamba tolerance markers as shown in Table 7.

TABLE 7

Haplotypes Associated with a Malformation and Sterility Ratings for 51 Soybean Lines.

| Line Number | Marker Haplotype | | | Rating | |
|---|---|---|---|---|---|
| | M0101742 | M0205350 | M0102027 | Malformation | Sterility |
| 123 | TT | TT | CC | 1 | 1 |
| 124 | CC | AA | CC | 3 | 2 |
| 126 | CC | AA | CC | 3 | 2 |
| 128 | TT | TT | CC | 1 | 1 |
| 135 | TT | TT | CC | 1 | 1 |
| 136 | CC | AA | CC | 3 | 3 |
| 140 | CC | AA | CC | 3 | 2 |
| 141 | TT | TT | CC | 1 | 1 |
| 143 | TT | TT | CC | 1 | 1 |
| 144 | CC | AA | CC | 3 | 2 |
| 145 | CC | AA | CC | 3 | 2 |
| 149 | CT | AT | CC | 1 | 1 |
| 151 | CC | AA | CC | 3 | 2 |
| 154 | CC | AA | CC | 3 | 2 |
| 156 | TT | TT | CC | 1 | 1 |
| 157 | CT | AT | CC | 1 | 1 |
| 159 | CC | AA | CC | 3 | 2 |
| 160 | CC | AA | CC | 3 | 2 |
| 164 | TT | TT | CC | 1 | 1 |
| 171 | CT | AT | CC | 1 | 1 |
| 173 | CC | AA | CC | 3 | 2 |
| 184 | CC | AA | CC | 3 | 2 |
| 189 | CC | AA | CC | 3 | 2 |
| 193 | CC | AA | CC | 3 | 2 |
| 200 | TT | TT | CC | 1 | 1 |
| 201 | CC | AA | CC | 3 | 2 |
| 203 | CC | AA | CC | 3 | 2 |
| 204 | CT | AT | CC | 1 | 1 |
| 212 | CC | AA | CC | 3 | 2 |
| 213 | TT | TT | CC | 1 | 1 |
| 214 | TT | TT | CC | 1 | 1 |
| 216 | CC | AA | CC | 3 | 2 |
| 217 | TT | TT | CC | 1 | 1 |
| 218 | TT | TT | CC | 1 | 1 |
| 222 | CT | AT | CC | 3 | 2 |
| 223 | CC | AA | CC | 3 | 2 |
| 225 | CT | AT | CC | 1 | 1 |
| 228 | TT | TT | CC | 1 | 1 |
| 230 | TT | TT | CC | 1 | 1 |
| 234 | CC | AA | CC | 3 | 2 |
| 235 | TT | TT | CC | 1 | 1 |
| 243 | CC | AA | CC | 3 | 2 |
| 246 | CC | AA | CC | 1 | 1 |
| 251 | CC | AA | CC | 3 | 3 |
| 260 | CC | AA | CC | 3 | 3 |
| 261 | CT | AT | CC | 1 | 1 |
| 262 | CT | AT | CC | 3 | 3 |
| 264 | CT | AT | CC | 1 | 1 |
| 268 | TT | TT | CC | 1 | 1 |
| 274 | CC | AA | CC | 3 | 2 |
| 277 | CC | AA | CC | 3 | 2 |
| 280 | CC | AA | CC | 3 | 2 |
| 281 | CC | AA | CC | 3 | 2 |
| 290 | CC | AA | CC | 3 | 2 |
| 309 | CC | AA | CC | 1 | 1 |
| 314 | CC | AA | CC | 3 | 2 |
| 316 | TT | TT | CC | 1 | 1 |
| 317 | CC | AA | CC | 3 | 2 |
| 318 | TT | TT | CC | 1 | 1 |
| 319 | TT | TT | CC | 1 | 1 |
| 324 | TT | TT | CC | 1 | 1 |
| 329 | CC | AA | CC | 3 | 3 |
| 330 | CC | AA | CC | 1 | 1 |
| 331 | CC | AA | CC | 1 | 1 |
| 333 | CC | AA | CC | 3 | 2 |
| 334 | CC | AA | CC | 1 | 1 |
| 336 | CC | AA | CC | 3 | 2 |
| 337 | CC | AA | CC | 1 | 1 |
| 338 | TT | TT | CC | 1 | 1 |
| 340 | CC | AA | CC | 3 | 2 |
| 347 | TT | TT | CC | 1 | 1 |
| 348 | TT | TT | CC | 1 | 1 |
| 350 | CT | AT | CC | 3 | 2 |
| 352 | CC | AA | CC | 3 | 2 |
| 353 | TT | TT | CC | 1 | 1 |
| 362 | CC | AA | CC | 3 | 2 |
| 379 | TT | TT | CC | 1 | 1 |
| 380 | TT | TT | CC | 1 | 1 |
| 381 | CC | AA | CC | 3 | 2 |
| 382 | CT | AT | CC | 1 | 1 |
| 384 | CC | AA | CC | 3 | 2 |
| 385 | CC | AA | CC | 3 | 2 |
| 393 | CT | AT | CC | 1 | 1 |
| 396 | TT | TT | CC | 1 | 1 |
| 398 | CC | AA | CC | 3 | 2 |
| 399 | CC | AA | CC | 3 | 2 |
| 400 | CC | AA | CC | 3 | 2 |
| 408 | CC | AA | CC | 3 | 2 |
| 409 | CC | AA | CC | 3 | 2 |
| 411 | TT | TT | CC | 1 | 1 |
| 412 | CC | AA | CC | 3 | 2 |
| 417 | TT | TT | CC | 1 | 1 |
| 421 | CC | AA | CC | 3 | 2 |
| 433 | CT | AT | CC | 1 | 1 |
| 434 | TT | TT | CC | 1 | 1 |
| 435 | TT | TT | CC | 1 | 1 |
| 440 | CC | AA | CC | 3 | 2 |
| 446 | CC | AA | CC | 3 | 3 |
| 449 | CC | AA | CC | 3 | 3 |
| 452 | TT | TT | CC | 1 | 1 |
| 457 | CC | AA | CC | 3 | 3 |
| 460 | CC | AA | CC | 3 | 2 |
| 467 | TT | TT | CC | 1 | 1 |

TABLE 7-continued

Haplotypes Associated with a Malformation
and Sterility Ratings for 51 Soybean Lines.

| Line Number | Marker Haplotype | | | Rating | |
|---|---|---|---|---|---|
| | M0101742 | M0205350 | M0102027 | Malformation | Sterility |
| 468 | CC | AA | CC | 3 | 3 |
| 470 | CC | AA | CC | 3 | 2 |
| 488 | CC | AA | CC | 3 | 2 |
| 490 | CC | AA | CC | 3 | 2 |
| 494 | CC | AA | CC | 3 | 3 |
| 495 | CC | AA | CC | 3 | 2 |
| 500 | CC | AA | CC | 3 | 2 |
| 505 | CC | AA | CC | 3 | 2 |
| 510 | TT | TT | CC | 1 | 1 |
| 512 | CC | AA | CC | 1 | 1 |

The 34 lines with the TTTTCC haplotype had a rating of "1" for malformation and "1" for sterility as summarized in Table 8.

TABLE 8

Summary of Table 7.

| No. of lines | Rating | | Marker Haplotype | | |
|---|---|---|---|---|---|
| | Malformation | Sterility | M0101742 | M0205350 | M0102027 |
| 34 | 1 | 1 | TT | TT | CC |
| 59 | 3 | 2 or 3 | CC | AA | CC |
| 7 | 1 | 1 | | | |
| 10 | 1 | 1 | CT | AT | CC |
| 3 | 3 | 2 or 3 | | | |

Out of the 66 lines with the CCAACC haplotype, 59 had a rating of "3" for malformation and a rating of "2" or "3" for sterility. The 13 lines heterozygous for the markers had a range of ratings for malformation and sterility.

These results support the observations that certain haplotypes at the dicamba tolerance locus in lines containing the RR2Y CP4 and DMO transgenes causes sterility from glyphosate and malformation from dicamba applications made at the V6 plant stage Example 3: Haplotypes Associated with a Malformation and Sterility Phenotypes for MG 3 and 4 Populations Upon Herbicide Application in Fontezuela, Argentina The effect of different haplotypes on response to glyphosate were evaluated by measuring observing sterility in MG3 to MG4 lines in glyphosate spray trials in Fontezuela, Argentina in 2012. The lines were from populations known to segregate for markers at the dicamba tolerance locus based on parental haplotypes. During the breeding process, the haplotype for each line at the dicamba tolerance locus was not known. Table 9 describes the breeding history for this material.

TABLE 9

Breeding History for Plant Material in Example 3.

| Gen. | Season | Year | Location | Breeding Activity |
|---|---|---|---|---|
| Cross | Winter or Summer | 2010 | Isabella, Puerto Rico, or Galena, MD | Cross |
| F1 | Summer or Winter | 2010 | Isabella, Puerto Rico | Bulk |
| F2 | Winter | 2011 | Kunia, HI | Bulk |
| F3 | Summer | 2011 | Stonington, IL | Single plant selection |
| F4 | Summer | 2012 | Fontezuela, Argentina | Progeny row |

Markers were used to select for the absence of the RR1 CP4 gene, and for the presence of the RR2Y CP4 gene and the Dicamba resistance (DMO) gene. A total of 1,083 F3:4 lines across six populations were planted in 4 foot single row plots. Remnant seed from each line was used for genotyping the lines across two markers at the dicamba tolerance locus. The lines were sprayed with 1.125 lb a.e./acre of glyphosate at V3 plant stage followed by the same rate applied at V6. Sterility ratings were taken at maturity.
A rating of 1: Less than 10% of plants show sterility
A rating of 2: 10-50% of plants show sterility
A rating of 3: Greater than 50% of plants show sterility
The sterility ratings by haplotype class are shown in Table 10.

TABLE 10

Haplotypes Associated with sterility ratings for Selected Soybean Populations.

| Population | Marker Haplotype | | Total No. of Lines | No. lines per rating class | | |
|---|---|---|---|---|---|---|
| | M0101742 | M0205350 | | 1 | 2 | 3 |
| POP1 | TT | TT | 42 | 42 | | |
| | CC | AA | 27 | | 10 | 17 |
| | CT | AT | 25 | 1 | 23 | 1 |
| POP2 | TT | TT | 83 | 83 | | |
| | TT | AA | 23 | | 8 | 15 |
| | TT | AT | 36 | | 11 | 25 |
| POP3 | TT | TT | 81 | 81 | | |
| | CC | AA | 89 | | 24 | 65 |
| | CT | AT | 40 | 4 | 27 | 9 |
| POP4 | TT | TT | 69 | 69 | | |
| | CC | AA | 43 | 1 | 2 | 40 |
| | CT | AT | 39 | 1 | 27 | 11 |
| | TT | TT | 75 | 75 | | |
| | TT | AA | 62 | | 3 | 59 |
| | TT | AT | 44 | | 44 | |
| POP5 | TT | TT | 185 | 185 | | |
| | CC | AA | 66 | | 2 | 64 |
| | CT | AT | 54 | 4 | 47 | 3 |
| Across populations (POP1-5) | TT | TT | 535 | 535 | 0 | 0 |
| | CC | AA | 225 | 1 | 38 | 186 |
| | TT | AA | 85 | 0 | 11 | 74 |
| | CT | AT | 158 | 10 | 124 | 24 |
| | TT | AT | 80 | 0 | 55 | 25 |

Lines with the TTTT haplotype for markers M0101742 and M0205350 did not show sterility across all populations. Nearly all lines with a CCAA or TTAA haplotype had at least 10% of plants that showed sterility. It is not unexpected that some plants in these lines did no show sterility as some variation in the spray application or other environmental variations can influence the expression of sterility. Lines genotyped as CTAT or TTAT were segregating at the dicamba tolerance locus and progeny from these lines showed a range of response for sterility.

These results support the observations that certain haplotypes at the dicamba tolerance locus in lines containing the RR2Y CP4 and DMO transgenes causes sterility from glyphosate applications made at the V6 plant stage.

Example 4: Exemplary Marker Assays for Detecting Polymorphisms

In one embodiment, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means. Exemplary primers and probes for amplifying and detecting genomic regions associated with a dicamba tolerance phenotype are given in Table 11.

that the SBE method can use three synthetic oligonucleotides. Two of the oligonucleotides serve as PCR primers and are complementary to the sequence of the locus which flanks a region containing the polymorphism to be assayed. Exemplary extension primers that can be used to type polymorphisms disclosed in this invention are provided in Table 12 in the column labeled "Probe (SBE)". Following amplification of the region containing the polymorphism, the PCR product is hybridized with an extension primer which anneals to the amplified DNA adjacent to the polymorphism. DNA polymerase and two differentially labeled dideoxynucleoside triphosphates are then provided. If the polymorphism is present on the template, one of the labeled

TABLE 11

Exemplary Assays for Detecting Polymorphisms

| Marker or Locus Name | Marker SEQ NO ID: | SNP Position | SEQ ID NO Forward Primer | SEQ ID NO Reverse Primer | SEQ ID NO Probe 1 | SEQ ID NO Probe 2 |
|---|---|---|---|---|---|---|
| asmbl_11856 | 1 | | | | | |
| TC122822 | 2 | | | | | |
| BI967232 | 3 | | | | | |
| M0205928 | 4 | | | | | |
| M0101742[3] | 5 | 1206 | 24 | 25 | 26 | 27 |
| M0129138 | 6 | 218 | 28 | 29 | 30 | 31 |
| BU551345 | 7 | | | | | |
| M0114388 | 8 | 502 | 32 | 33 | 34 | 35 |
| BU551363 | 9 | | | | | |
| M0205350[4] | 10 | 148 | 36 | 37 | 38 | 39 |
| M0102027[5] | 11 | 349 | 40 | 41 | 42 | 43 |
| BU765955 | 12 | | | | | |
| M0093116 | 13 | 183 | 44 | 45 | 46 | 47 |
| M0129925 | 14 | 328 | 48 | 49 | 50 | 51 |
| M0205537 | 15 | | | | | |
| M0202715 | 16 | | | | | |
| M0206286 | 17 | | | | | |
| M0206054 | 18 | | | | | |
| M0205375 | 19 | | | | | |
| NGMAX008197032 | 52 | 201 | 53 | 54 | 55 | 56 |

Example 5: Oligonucleotide Probes Useful for Detecting Polymorphisms by Single Base Extension Methods Oligonucleotides can also be used to detect or type the polymorphisms disclosed herein by single base extension (SBE)-based SNP detection methods. Exemplary oligonucleotides for use in SBE-based SNP detection are provided in Table 12. SBE methods are based on extension of a nucleotide primer that is hybridized to sequences adjacent to a polymorphism to incorporate a detectable nucleotide residue upon extension of the primer. It is also anticipated dideoxynucleoside triphosphates can be added to the primer in a single base chain extension. The allele present is then inferred by determining which of the two differential labels was added to the extension primer. Homozygous samples will result in only one of the two labeled bases being incorporated and thus only one of the two labels will be detected. Heterozygous samples have both alleles present, and will thus direct incorporation of both labels (into different molecules of the extension primer) and thus both labels will be detected. Exemplary forward and reverse SBE probes are provided in Table 12.

TABLE 12

Exemplary SBE Probes for Detecting Polymorphisms

| Marker or Locus Name | Marker (SEQ ID NO) | SNP Position | Probe (SBE) | Probe (SEQ ID NO) |
|---|---|---|---|---|
| M0101742 | 5 | 1206 | TGACTAGCATGTATCTAT | 26 |
| | | | ATGACTAACATGTATCTAT | 27 |
| M0129138 | 6 | 218 | TGTGTCCTATATGATCTT | 30 |
| | | | TGTCCTGTATGATCTTA | 31 |
| M0114388 | 8 | 502 | AGTTGGGCTATGCAA | 34 |
| | | | TGGGCTGTGCAAGTA | 35 |

TABLE 12-continued

Exemplary SBE Probes for Detecting Polymorphisms

| Marker or Locus Name | Marker (SEQ ID NO) | SNP Position | Probe (SBE) | Probe (SEQ ID NO) |
|---|---|---|---|---|
| M0205350 | 10 | 148 | AGTTTACACTTACAAATATT | 38 |
|  |  |  | AGAGTTTACACTTACATATATT | 39 |
| M0102027 | 11 | 349 | ACCCCCCTTTTTT | 42 |
|  |  |  | ATTTTAACCCCCTTTTT | 43 |
| M0093116 | 13 | 183 | CCAACACCAAACTA | 46 |
|  |  |  | CAACACCAAACAAA | 47 |
| M0129925 | 14 | 328 | AGTAGTAGCTAGTGAAATA | 50 |
|  |  |  | AGCTAGTCAAATATTT | 51 |
| NGMAX008197032 | 52 | 201 | TTGACAGCCTCTGGATAT | 55 |
|  |  |  | ACAGCCTCCGGATAT | 56 |

Example 6: Haplotypes Associated with a Malformation and Sterility Phenotypes in MG 4 Populations Upon Herbicide Application The effect of different haplotypes on response to dicamba and glyphosate were evaluated by comparing genetically similar lines that contained a CP4 transgene that confers tolerance to glyphosate and a DMO transgene that confers tolerance to dicamba. In 2010, two plants from each of fourteen BC1F2:4 lines, or families, across five backcross populations were harvested individually to develop pairs of BC1F4:6 lines from each family. The haplotype of each recurrent parent for each backcross population is shown in Table 13.

TABLE 13

Haplotypes Associated With Listed Recurrent Parent.

| Backcross population | Recurrent parent | Recurrent parent haplotype | | |
|---|---|---|---|---|
|  |  | M0101742 | M0205350 | M0102027 |
| 1 | CBL3606Q0R | CC | AA | TT |
| 2 | AG4005 | CC | AA | TT |
| 3 | CP4408A3-C0RN | CC | AA | TT |
| 4 | AG4907 | CC | AA | TT |
| 5 | AG4630 | TT | AA | TT |

The donor parent for each population was A3244-RR2Y/A3525-DT that had a TTTTCC haplotype for markers M0101742, M0205350, and M0102027 markers, respectively. During the breeding process, the haplotype for each line at the dicamba tolerance locus was not known. Markers were used to select for the absence of the RR1 CP4 gene, and for the presence of the RR2Y CP4 gene and the Dicamba DMO gene. The BC1F4:5 rows were sprayed with glyphosate at the V6 plant growth stage in Quillota Chile where a pair of lines per family were rated for sterility to glyphosate. Table 14 describes the breeding history for this plant material.

TABLE 14

Breeding History for Plant Material in Example 6.

| Gen. | Season | Year | Location | Breeding Activity |
|---|---|---|---|---|
| Cross | Winter | 2007 | Isabella, Puerto Rico | Cross |
| F1 | Summer | 2008 | Isabella, Puerto Rico | Backcross |
| BC1F1 | Winter | 2008 | Isabella, Puerto Rico | Bulk |

TABLE 14-continued

Breeding History for Plant Material in Example 6.

| Gen. | Season | Year | Location | Breeding Activity |
|---|---|---|---|---|
| BC1F2 | Summer | 2009 | Evansville, IN, Stonington, IL, or Galena, MD | Single plant selection |
| BC1F2:3 | Summer | 2010 | Fontezuela, Argentina | Progeny row |
| BC1F2:4 | Summer | 2010 | Evansville, IN, Stonington, IL, or Galena, MD | Single plant selection |
| BC1F4:5 | Summer | 2011 | Quillota, Chile | Progeny row |
| BC1F4:6 | Summer | 2011 | Evansville, IN, Stonington, IL, Galena, MD, and Stuttgart, AR | Spray trials |

DNA was extracted from each line to generate haplotypes across three markers at the dicamba tolerance locus. The lines were evaluated across four locations in the United States (Stuttgart, Ark.; Stonington Ill.; Evansville, Ind.; and Galena, Md.) in 2011. At each location the lines were grown in four to five foot single-row plots replicated two times and one of seven different herbicide treatments were applied at different plant growth stages (V3 or V6) as described in Table 15.

TABLE 15

Herbicide Treatments (Glyphosate and Dicamba) and Concentrations Applied at Plant Growth Stages (V3 or V6).

| Herbicide Treatment Number | Glyphosate V3 | Dicamba V3 | Glyphosate V6 | Dicamba V6 |
|---|---|---|---|---|
| 1 | none | none | none | none |
| 2 | 0.75 lb a.e./acre | none | none | none |
| 3 | 0.75 lb a.e./acre | none | 1.5 lb a.e./acre | none |
| 4 | none | 1.0 lb a.e./acre | none | none |
| 5 | none | 1.0 lb a.e./acre | none | 1.0 lb a.e./acre |
| 6 | 0.75 lb a.e./acre | 1.0 lb a.e./acre | none | none |
| 7 | 0.75 lb a.e./acre | 1.0 lb a.e./acre | 1.5 lb a.e./acre | 1.0 lb a.e./acre |

Rating Scale:
Malformation to dicamba was rated by the percentage of plants showing malformation Sterility to glyphosate was rated as:

A rating scale of 1: Less than 10% of plants show sterility
A rating scale of 2: Less than 10-50% of plants show sterility
A rating scale 3: Greater than 50% of plants show sterility Data were averaged across replications and locations to place into following classes as described in Table 16.

TABLE 16

Haplotypes Associated with a Malformation and Sterility Phenotypes in Soybean Sister Line Pedigrees in Response to Herbicide Treatment Protocols.

| Backcross Population | Family | Reaction to Glyphosate in Quillota, Chile | Marker haplotype M0101742 | M0205350 | M0102027 | 1 | 2 | 3 | 4 | 5 | 6 | 7 |
|---|---|---|---|---|---|---|---|---|---|---|---|---|
| | | | | | | | | Response | | | | |
| 1 | 1.1 | N | TT | TT | CC | N | N | N | N | N | N | N |
| | | S | CC | AA | TT | N | N | S | N | M | N | M/S |
| 2 | 2.1 | S | CC | AA | TT | N | N | S | N | M | N | M/S |
| | | S | CC | AA | TT | N | N | S | N | M | N | M/S |
| 3 | 3.1 | N | TT | TT | CC | N | N | N | N | N | N | N |
| | | S | CC | AA | TT | N | N | S | N | M | N | M/S |
| 4 | 4.1 | S | CC | AA | TT | N | N | S | N | M | N | M/S |
| | | | N | TT | TT | CC | N | N | N | N | N | N | N |
| | 4.2 | S | CC | AA | TT | N | N | S | N | M | N | M/S |
| | | S | CC | AA | TT | N | N | S | N | M | N | M/S |
| | 4.3 | S | CC | AA | TT | N | N | S | N | M | N | M/S |
| | | S | CC | AA | TT | N | N | S | N | M | N | M/S |
| | 4.4 | S | CC | AA | TT | N | N | S | N | M | N | M/S |
| | | S | CC | AA | TT | N | N | S | N | M | N | M/S |
| | 4.5 | S | CC | AA | TT | N | N | S | N | M | N | M/S |
| | | S | CC | AA | TT | N | N | S | N | M | N | M/S |
| | 4.6 | N | TT | TT | CC | N | N | N | N | N | N | N |
| | | N | TT | TT | CC | N | N | N | N | N | N | N |
| | 4.7 | N | TT | TT | CC | N | N | N | N | N | N | N |
| | | S | CC | AA | TT | N | N | S | N | M | N | M/S |
| | 4.8 | S | CC | AA | TT | N | N | S | N | M | N | M/S |
| | | S | CC | AA | TT | N | N | S | N | M | N | M/S |
| | 4.9 | S | CC | AA | TT | N | N | S | N | M | N | M/S |
| | | S | CC | AA | TT | N | N | S | N | M | N | M/S |
| | 4.10 | S | CC | AA | TT | N | N | S | N | M | N | M/S |
| | | S | CC | AA | TT | N | N | S | N | M | N | M/S |
| 5 | 5.1 | S | TT | AA | TT | N | N | S | N | M | N | M/S |
| | | N | TT | TT | CC | N | N | N | N | N | N | N |

N = normal response to treatment: Average </=1.25 sterility and/or </=30% malformation
S = sterility to a glyphosate treatment: Average >1.25
M = malformation to a dicamba treatment >30% malformation
M/S = malformation dicamba and sterility to glyphosate in a combination treatment Example 7: Selection for Absence of Sterility to Glyphosate Application and Recovery of the Favorable Haplotype As described in Example 3, marker haplotypes corresponded to reaction to glyphosate application. There were several populations grown in Fontezuela, Argentina where plants sprayed with glyphosate were selected for reproductive tolerance to glyphosate in the absence of haplotype information on each line. Table 17 describes four populations that segregated for the haplotype based on parental haplotypes. Table 18 describes the number of lines grown and the number of lines selected.

TABLE 17

Four soybean populations that segregated for the preferred haplotype based on parental haplotypes.

| | | Parent 1 | | Parent 2 | |
|---|---|---|---|---|---|
| | Population Origin | NGMAX-008197032 (SEQ ID NO: 52) | M-0205350 (SEQ ID NO: 10) | NGMAX-008197032 (SEQ ID NO: 52) | M-0205350 (SEQ ID NO: 10) |
| 1 | AG4031/AG3803-T0BAH | GG | AA | AA | TT |
| 2 | AG4130/AG4907-T0BAH | AA | TT | GG | AA |

TABLE 17-continued

Four soybean populations that segregated for the preferred haplotype based on parental haplotypes.

| | | Parent 1 | | Parent 2 | |
|---|---|---|---|---|---|
| Population | Origin | NGMAX-008197032 (SEQ ID NO: 52) | M-0205350 (SEQ ID NO: 10) | NGMAX-008197032 (SEQ ID NO: 52) | M-0205350 (SEQ ID NO: 10) |
| 3 | BL3510A9-D0AAC/AG4907-T0BAH | AA | TT | GG | AA |
| 4 | EI4409C3-D0YN/GL4807A2-D0RN-T0BAH | GG | AA | AA | TT |

TABLE 18

Number of soybean lines grown and the number of soybean lines selected.

| Population | No. Lines Grown | No. Lines Selected |
|---|---|---|
| 1 | 165 | 2 |
| 2 | 92 | 9 |
| 3 | 200 | 10 |
| 4 | 260 | 25 |
| Total | 717 | 46 |

The 46 selected lines were subsequently genotyped and found to possess the favorable AATT haplotype. In addition, the lines were grown at Stonington, Ill. in 2012 and evaluated for herbicide response. The lines were sprayed with 1.0 lb a.e/acre dicamba and 1.5 lb a.e/acre glyphosate at the V6 plant stage and did not show malformation to dicamba or sterility to glyphosate. These results further support the ability to use glyphosate selection as a means to recover the favorable haplotype and tolerance to both glyphosate and dicamba.

Example 8: Comparison of Dicamba Tolerance in Different Haplotypes Containing a Dicamba Resistance Conferring Transgene The effect of different haplotypes on response to dicamba was evaluated by comparing F2 families that contained the DMO transgene for dicamba resistance, but that lacked the CP4 transgene for glyphosate resistance. F2 plants across six different populations that were growing in Kunia, Hi. in 2012 were tissue sampled and genotyped for the CP4 and DMO transgenes and for markers NGMAX008197032 and M0205350. F2 plants that were fixed homozygous for the presence of DMO and absence of CP4 and that were fixed homozygous for a haplotype class were selected and harvested individually to create families. Table 19 shows the number of F2 families per haplotype class. The F2 families were evaluated for tolerance to dicamba in a greenhouse environment.

TABLE 19

Six soybean populations that segregated for the preferred haplotype based on parental haplotypes.

| | | Haplotype Class | |
|---|---|---|---|
| POP | ORIGIN | AATT[1] Number of F2 plants | GGAA[2] |
| 5 | A3525-A3244-BAH/A3431 | 8 | 10 |
| 6 | DKB31-51/A3525-A3244-BAH | 3 | 3 |
| 8 | AG4903/A3525-A3244-BAH | 0 | 3 |
| 9 | AG4907/A3525-A3244-BAH | 2 | 2 |
| 12 | AG4903/(AG4903*2/A3525-A3244-BAH) | 0 | 5 |
| 13 | AG4907/GL4911A9-B0BAH | 0 | 5 |

[1] An "AA" allele for NGMAX-008197032 (SEQ ID NO: 52) and a "TT" allele for M020535 (SEQ ID NO: 10) (i.e. "favorable" haplotype for dicamba tolerance).
[2] A "GG" allele for NGMAX-008197032 (SEQ ID NO: 52) and an "AA" allele for M020535 (SEQ ID NO: 10) (i.e. "unfavorable" haplotype for dicamba tolerance).

Figure 1:
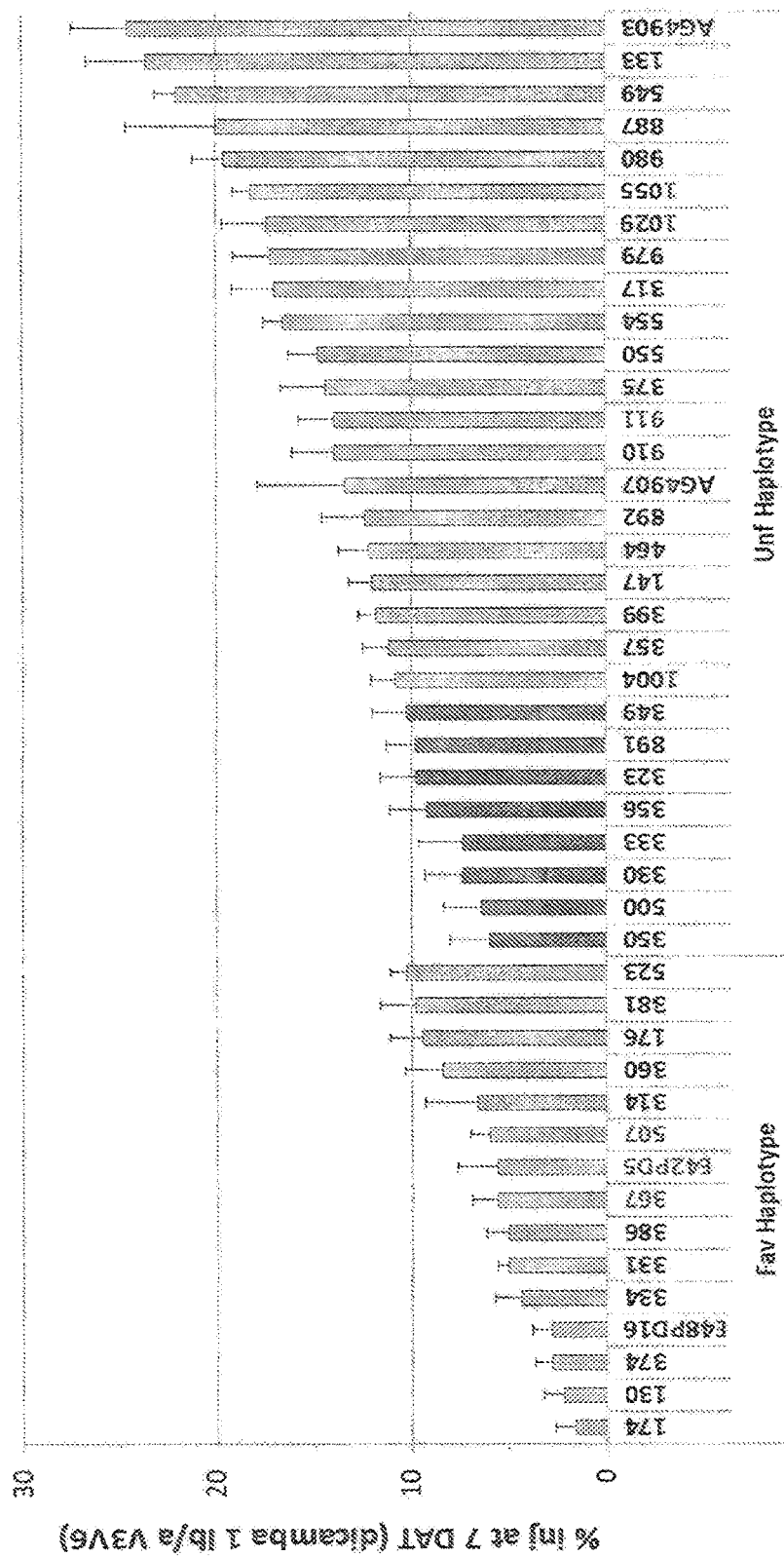
FIG. 1 shows a bar graph of the percent injury at 7 days after treatment with Dicamba (y-axis) for various favorable and unfavorable soybean plant haplotypes containing a dicamba resistance conferring transgene (x-axis). The favorable haplotypes are haplotypes that are not associated with the dicamba intolerance trait and the unfavorable haplotypes are associated with the dicamba intolerance trait. In the graph, "Fav Hap is "Favorable Haplotype" and "Unf Hap"

A comparison of dicamba tolerance in the plants from segregating populations of Table 19 having various "favorable" or "unfavorable" haplotypes of the indicated parental germplasm is provided in FIG. 1. Plants having the favorable haplotypes (i.e. an "AA" allele for NGMAX-008197032 (SEQ ID NO:52) and a "TT" allele for M020535 (SEQ ID NO: 10) showed consistently low dicamba injury (FIG. 1).

Example 9: Selection of Favorable Dicamba Tolerance Haplotypes with One or Two Spray Treatments A comparison of selections of favorable and unfavorable dicamba tolerance haplotypes based on either one or two spray treatments was made. Transgenic soybean plants containing a dicamba resistance conferring transgene and various favorable or unfavorable haplotypes were treated with dicamba at a rate of 1 pound/acre at either: (a) the V3 and V6 stages; or (b) the V6 stage only. The results of this comparison are shown in FIG. 2. Selection of favorable haplotypes by using a single spray at V6 (dicamba 1 lb/a) was found to be as effective as selections with the combination of aV3 and a V6 spray treatment.

Having illustrated and described the principles of the present invention, it should be apparent to persons skilled in the art that the invention can be modified in arrangement and detail without departing from such principles.

Although the materials and methods of this invention have been described in terms of various embodiments and illustrative examples, it will be apparent to those of skill in the art that variations can be applied to the materials and methods described herein without departing from the concept, spirit and scope of the invention. All such similar substitutes and modifications apparent to those skilled in the art are deemed to be within the spirit, scope and concept of the invention as defined by the appended claims.

TABLE 2 of the Specification

| Locus/Display Name (1) | Source (2) | Start Base (3) | End Base (4) | ADDITIONAL LOCUS INFORMATION (5) |
|---|---|---|---|---|
| asmbl_11856 | Vigna_unguiculata | 16426 | 16586 | SEQ ID NO: 1 |
| TA2790_3886 | Phaseolus_coccineus_release_2 | 16423 | 17393 | ADP-ribosylation factor [Vigna unguiculata (Cowpea)] |
| TA43459_3847 | Glycine_max_release_2 | 16434 | 18055 | ADP-ribosylation factor 1 [Oryza sativa (Rice)] |
| TC276541 | GMGI.071508 | 16434 | 18076 | UniRef100_P36397 Cluster: ADP-ribosylation factor 1; n = 1; Arabidopsis thaliana\|Rep: ADP-ribosylation factor 1 - Arabidopsis thaliana (Mouse-ear cress) = partial (38%) |
| CD392203 | Glycine_max_release_2 | 16216 | 18687 | ADP-ribosylation factor [Glycine max (Soybean)] |
| BQ610865 | Glycine_max_release_2 | 16327 | 18667 | ADP-ribosylation factor 1 [Oryza sativa (Rice)] |
| EH046324 | Arachis_stenosperma_release_5 | 16405 | 18745 | Cluster: ADP-ribosylation factor 1, n = 1, Arabidopsis thaliana\|Rep: ADP-ribosylation factor 1 - Arabidopsis thaliana (Mouse-ear cress) |
| AW202311 | Glycine_max_release_2 | 16378 | 19070 | ADP-ribosylation factor [Glycine max (Soybean)] |
| TC242702 | GMGI.071508 | 16234 | 20195 | UniRef100_Q38JU3 Cluster: ADP ribosylation factor 002; n = 2; core eudicotyledons\|Rep: ADP ribosylation factor 002 - Daucus carota (Carrot) = complete |
| BI321678 | Glycine_max_release_2 | 17384 | 19066 | ADP-ribosylation factor [Zea mays (Maize)] |
| AW348317 | Glycine_max_release_2 | 16355 | 20097 | ADP-ribosylation factor [Glycine max (Soybean)] |
| EH042959 | Arachis_stenosperma_release_5 | 16401 | 20182 | Cluster: ADP-ribosylation factor 1, n = 2, Medicago\|Rep: ADP-ribosylation factor 1 - Medicago truncatula (Barrel medic) |
| TC20337 | LJGI.070108 | 16420 | 20191 | UniRef100_Q5QQ33 Cluster: ADP-ribosylation factor 1, n = 2, Medicago\|Rep: ADP-ribosylation factor 1 - Medicago truncatula (Barrel medic), complete |
| EH047563 | Arachis_stenosperma_release_5 | 16430 | 20182 | Cluster: ADP-ribosylation factor 1, n = 2, Medicago\|Rep: ADP-ribosylation factor 1 - Medicago truncatula (Barrel medic) |
| TA2789_3886 | Phaseolus_coccineus_release_2 | 16436 | 20196 | ADP-ribosylation factor 1-like protein [Solanum tuberosum (Potato)] |
| TA43462_3847 | Glycine_max_release_2 | 16229 | 20438 | ADP-ribosylation factor [Medicago sativa (Alfalfa)] |
| TA1120_34305 | Lotus_japonicus_release_1 | 16522 | 20191 | ADP-ribosylation factor [Medicago sativa (Alfalfa)] |
| TA2306_3848 | Glycine_soja_release_2 | 16442 | 20440 | ADP-ribosylation factor [Medicago sativa (Alfalfa)] |
| TC273941 | GMGI.071508 | 16426 | 20464 | homologue to UniRef100_Q38JU3 Cluster: ADP ribosylation factor 002; n = 2; core eudicotyledons\|Rep: ADP ribosylation factor 002 - Daucus carota (Carrot) = complete |

TABLE 2-continued of the Specification

| Locus/Display Name (1) | Source (2) | Start Base (3) | End Base (4) | ADDITIONAL LOCUS INFORMATION (5) |
|---|---|---|---|---|
| TC238119 | GMGI.071508 | 16455 | 20449 | UniRef100_Q38JU3 Cluster: ADP ribosylation factor 002; n = 2; core eudicotyledons\|Rep: ADP ribosylation factor 002 - *Daucus carota* (Carrot) = complete |
| EG373880 | *Arachis_hypogaea_* release_5 | 17101 | 20182 | Cluster: ADP-ribosylation factor 1, n = 2, *Medicago*\|Rep: ADP-ribosylation factor 1 - *Medicago truncatula* (Barrel medic) |
| BF066818 | *Glycine_max*_release_2 | 17081 | 20378 | ADP-ribosylation factor 1 [*Populus tomentosa*] |
| BF596154 | *Glycine_max*_release_2 | 17083 | 20397 | ADP-ribosylation factor [*Hyacinthus orientalis* (Common hyacinth)] |
| AW760997 | *Glycine_max*_release_2 | 17116 | 20397 | ADP-ribosylation factor [*Hyacinthus orientalis* (Common hyacinth)] |
| BF424079 | *Glycine_max*_release_2 | 17112 | 20417 | ADP-ribosylation factor [*Hyacinthus orientalis* (Common hyacinth)] |
| AW596022 | *Glycine_max*_release_2 | 17121 | 20415 | ADP-ribosylation factor 1 [*Populus tomentosa*] |
| TA43446_3847 | *Glycine_max*_release_2 | 17106 | 20436 | ADP-ribosylation factor [*Hyacinthus orientalis* (Common hyacinth)] |
| TA43455_3847 | *Glycine_max*_release_2 | 17125 | 20452 | ADP-ribosylation factor [*Hyacinthus orientalis* (Common hyacinth)] |
| BW595867 | *Lotus_japonicus_* release_1 | 17418 | 20191 | ADP-ribosylation factor [*Hyacinthus orientalis* (Common hyacinth)] |
| AW507598 | *Glycine_max*_release_2 | 17343 | 20437 | ADP-ribosylation factor [*Hyacinthus orientalis* (Common hyacinth)] |
| TA43447_3847 | *Glycine_max*_release_2 | 17343 | 20445 | ADP-ribosylation factor [*Hyacinthus orientalis* (Common hyacinth)] |
| TA43448_3847 | *Glycine_max*_release_2 | 17355 | 20438 | ADP-ribosylation factor 1 [*Populus tomentosa*] |
| AW596189 | *Glycine_max*_release_2 | 17358 | 20442 | ADP-ribosylation factor 1 [*Populus tomentosa*] |
| BI469983 | *Glycine_max*_release_2 | 17410 | 20438 | ADP-ribosylation factor 1 [*Populus tomentosa*] |
| AW472058 | *Glycine_max*_release_2 | 18655 | 20160 | ADP-ribosylation factor 1 [*Daucus carota* (Carrot)] |
| CB063805 | *Glycine_max*_release_2 | 18623 | 20432 | ADP-ribosylation factor 1 [*Populus tomentosa*] |
| BM891090 | GMGI.071508 | 18995 | 20429 | homologue to UniRef100_A7PRL9 Cluster: Chromosome chr14 scaffold_27 = whole genome shotgun sequence; n = 1; *Vitis vinifera*\|Rep: Chromosome chr14 scaffold_27 = whole genome shotgun sequence - *Vitis vinifera* (Grape) = partial (42%) |
| BM731935 | *Glycine_max*_release_2 | 19949 | 20444 | ADP-ribosylation factor 1 [*Populus tomentosa*] |
| AW695591 | MTGI.071708 | 30054 | 31388 | similar to UniRef100_Q40542 Cluster: NPK2, n = 1, *Nicotiana tabacum*\|Rep: NPK2 - *Nicotiana tabacum* (Common tobacco), partial (35%) |
| TC130040 | MTGI.071708 | 30054 | 31482 | similar to UniRef100_A7PM42 Cluster: Chromosome chr14 scaffold_21, whole |

TABLE 2-continued

| Locus/Display Name (1) | Source (2) | Start Base (3) | End Base (4) | ADDITIONAL LOCUS INFORMATION (5) |
|---|---|---|---|---|
| | | | | genome shotgun sequence, n = 1, *Vitis vinifera*\|Rep: Chromosome chr14 scaffold_21, whole genome shotgun sequence - *Vitis vinifera* (Grape), partial (30%) |
| TC122822 | MTGI.071708 | 30054 | 34162 | Protein kinase, Nuclear transport factor 2. SEQ ID NO: 2 |
| Pvcon9203 | *Phaseolus_vulgaris* | 31194 | 34247 | UniRef100_A7PM42 Chromosome chr14 scaffold_21, whole genome shotgun sequence n = 1 Tax = *Vitis vinifera* RepID = A7PM42_VITVI E-0 |
| TA66103_3847 | *Glycine_max*_release_2 | 31879 | 34559 | Protein kinase; Nuclear transport factor 2 [*Medicago truncatula* (Barrel medic)] |
| CA801261 | GMGI.071508 | 33896 | 34304 | similar to UniRef100_Q40542 Cluster: NPK2; n = 1; *Nicotiana tabacum*\|Rep: NPK2 - *Nicotiana tabacum* (Common tobacco) = partial (16%) |
| TC120073 | MTGI.071708 | 35367 | 38178 | Glycoside hydrolase, family 28 |
| NP004759 | GMGI.071508 | 34976 | 39622 | GB\|AF128266.1\|AAD46483.1 polygalacturonase PG1 |
| AF128266 | *Glycine_max*_release_2 | 34980 | 39622 | Polygalacturonase PG1 [*Glycine max* (Soybean)] |
| TA69799_3847 | *Glycine_max*_release_2 | 58988 | 65870 | Ubiquitin-associated [*Medicago truncatula* (Barrel medic)] |
| TA7619_47247 | *Lotus_corniculatus*_release_1 | 63855 | 65940 | Putative DNA cytosine methyltransferase Zmet3 related cluster |
| TA8711_34305 | *Lotus_japonicus*_release_1 | 63855 | 65940 | UBA-like [*Medicago truncatula* (Barrel medic)] |
| TC34762 | LJGI.070108 | 65619 | 65940 | NA |
| Pvcon5587 | *Phaseolus_vulgaris* | 65216 | 67090 | UniRef100_A7PM76 Chromosome chr14 scaffold_21, whole genome shotgun sequence n = 1 Tax = *Vitis vinifera* RepID = A7PM76_VITVI E-0 |
| TA5046_3885 | *Phaseolus_vulgaris*_release_2 | 65808 | 67002 | UBA-like [*Medicago truncatula* (Barrel medic)] |
| asmbl_11857 | *Vigna_unguiculata* | 65951 | 67042 | NA |
| TA58707_3847 | *Glycine_max*_release_2 | 66006 | 67253 | UBA-like [*Medicago truncatula* (Barrel medic)] |
| TC241193 | GMGI.071508 | 66006 | 67253 | similar to UniRef100_A7PM76 Cluster: Chromosome chr14 scaffold_21 = whole genome shotgun sequence; n = 1; *Vitis vinifera*\|Rep: Chromosome chr14 scaffold_21 = whole genome shotgun sequence - *Vitis vinifera* (Grape) = partial (38%) |
| BI967232 | *Glycine_max*_release_2 | 66170 | 67203 | UBA-like [*Medicago truncatula* (Barrel medic)]. SEQ ID NO: 3 |
| AV417590 | LJGI.070108 | 66745 | 67090 | similar to UniRef100_A7PM76 Cluster: Chromosome chr14 scaffold_21, whole genome shotgun sequence, n = 1, *Vitis vinifera*\|Rep: Chromosome chr14 |

TABLE 2-continued of the Specification

| Locus/Display Name (1) | Source (2) | Start Base (3) | End Base (4) | ADDITIONAL LOCUS INFORMATION (5) |
|---|---|---|---|---|
| | | | | scaffold_21, whole genome shotgun sequence - *Vitis vinifera* (Grape), partial (19%) |
| AV768315 | *Lotus_japonicus_*release_1 | 66699 | 67155 | UBA-like [*Medicago truncatula* (Barrel medic)] |
| TC32114 | LJGI.070108 | 66699 | 67275 | similar to UniRef100_Q76KU6 Cluster: DNA methyltransferase, n = 1, *Nicotiana tabacum*|Rep: DNA methyltransferase - *Nicotiana tabacum* (Common tobacco), partial (20%) |
| TA1535_34305 | *Lotus_japonicus_*release_1 | 66745 | 67277 | UBA-like [*Medicago truncatula* (Barrel medic)] |
| TA2793_47247 | *Lotus_corniculatus_*release_1 | 66745 | 67277 | DNA methyltransferase related cluster |
| AV768911 | *Lotus_japonicus_*release_1 | 66943 | 67155 | Ubiquitin-associated [*Medicago truncatula* (Barrel medic)] |
| CB540531 | *Phaseolus_vulgaris* | 73267 | 73561 | UniRef100_A7PM74 Chromosome chr14 scaffold_21, whole genome shotgun sequence n = 1 Tax = *Vitis vinifera* RepID = A7PM74_VITVI 5.00E−27 |
| BE347690 | GMGI.071508 | 73509 | 73770 | similar to UniRef100_Q5VQL1-2 Cluster: Isoform 2 of Q5VQL1; n = 1; *Oryza sativa Japonica* Group|Rep: Isoform 2 of Q5VQL1 - *Oryza sativa* subsp. *japonica* (Rice) = partial (5%) |
| BE347690 | *Glycine_max_*release_2 | 73509 | 73822 | WW/Rsp5/WWP; Helicase = C-terminal [*Medicago truncatula* (Barrel medic)] |
| BE608496 | GMGI.071508 | 73444 | 73947 | similar to UniRef100_A7PM74 Cluster: Chromosome chr14 scaffold_21 = whole genome shotgun sequence; n = 1; *Vitis vinifera*|Rep: Chromosome chr14 scaffold_21 = whole genome shotgun sequence - *Vitis vinifera* (Grape) = partial (16%) |
| AI416763 | GMGI.071508 | 74073 | 74520 | similar to UniRef100_Q9SP26 Cluster: P72 DEAD box protein; n = 1; *Pisum sativum*|Rep: P72 DEAD box protein - *Pisum sativum* (Garden pea) = partial (16%) |
| AI416763 | *Glycine_max_*release_2 | 74073 | 74743 | ATP-dependent RNA helicase-like protein DB10 [*Nicotiana sylvestris* (Wood tobacco)] |
| BW615083 | LJGI.070108 | 74256 | 74855 | similar to UniRef100_A7PM74 Cluster: Chromosome chr14 scaffold_21, whole genome shotgun sequence, n = 1, *Vitis vinifera*|Rep: |

TABLE 2-continued of the Specification

| Locus/Display Name (1) | Source (2) | Start Base (3) | End Base (4) | ADDITIONAL LOCUS INFORMATION (5) |
|---|---|---|---|---|
| | | | | Chromosome chr14 scaffold_21, whole genome shotgun sequence - *Vitis vinifera* (Grape), partial (24%) |
| TA8332_34305 | *Lotus_japonicus_* release_1 | 74256 | 75446 | WW/Rsp5/WWP, Helicase, C-terminal [*Medicago truncatula* (Barrel medic)] |
| TC27807 | LJGI.070108 | 74343 | 75446 | similar to UniRef100_Q9SP26 Cluster: P72 DEAD box protein, n = 1, *Pisum sativum*\|Rep: P72 DEAD box protein - *Pisum sativum* (Garden pea), partial (34%) |
| asmbl_11858 | *Vigna_unguiculata* | 75228 | 75500 | NA |
| TA60825_3847 | *Glycine_max*_release_2 | 74963 | 75981 | P72 DEAD box protein [*Pisum sativum* (Garden pea)] |
| TC249436 | GMGI.071508 | 74985 | 75966 | similar to UniRef100_Q9SP26 Cluster: P72 DEAD box protein; n = 1; *Pisum sativum*\|Rep: P72 DEAD box protein - *Pisum sativum* (Garden pea) = partial (12%) |
| TC269249 | GMGI.071508 | 86882 | 87576 | similar to UniRef100_A7PM72 Cluster: Chromosome chr14 scaffold_21 = whole genome shotgun sequence; n = 1; *Vitis vinifera*\|Rep: Chromosome chr14 scaffold_21 = whole genome shotgun sequence - *Vitis vinifera* (Grape) = partial (42%) |
| TA64136_3847 | *Glycine_max*_release_2 | 86882 | 89066 | Putative phosphate/phosphoenolpyruvate translocator [*Arabidopsis thaliana* (Mouse-ear cress)] |
| CO982132 | *Glycine_max*_release_2 | 87225 | 91497 | Phosphate/phosphoenolpyruvate translocator [*Nicotiana tabacum* (Common tobacco)] |
| TC274531 | GMGI.071508 | 87225 | 91497 | similar to UniRef100_A4UTS3 Cluster: Chloroplast phosphoenolpyruvate/ phosphate translocator; n = 1; *Pisum sativum*\|Rep: Chloroplast phosphoenolpyruvate/ phosphate translocator - *Pisum sativum* (Garden pea) = partial (53%) |
| Pvcon2802 | *Phaseolus_vulgaris* | 87119 | 92616 | UniRef100_A9PD12 Putative uncharacterized protein n = 1 Tax = *Populus trichocarpa* RepID = A9PD12_POPTR 1.00E−121 |
| TA4406_3885 | *Phaseolus_vulgaris_* release_2 | 89055 | 92616 | Phosphate/phosphoenolpyruvate translocator [*Nicotiana tabacum* (Common tobacco)] |
| TA74766_3847 | *Glycine_max*_release_2 | 91397 | 92725 | Phosphoenolpyruvate/ phosphate translocator [*Mesembryanthemum crystallinum* (Common ice plant)] |

TABLE 2-continued of the Specification

| Locus/Display Name (1) | Source (2) | Start Base (3) | End Base (4) | ADDITIONAL LOCUS INFORMATION (5) |
|---|---|---|---|---|
| TC265023 | GMGI.071508 | 91686 | 92725 | similar to UniRef100_A7PM71 Cluster: Chromosome chr14 scaffold_21 = whole genome shotgun sequence; n = 1; *Vitis vinifera*|Rep: Chromosome chr14 scaffold_21 = whole genome shotgun sequence - *Vitis vinifera* (Grape) = partial (15%) |
| M0205928 | SEQ. LISTING | 92718 | 92334 | SEQ ID NO: 4 |
| BG406195 | GMGI.071508 | 107039 | 107366 | |
| BG406195 | *Glycine_max_release_2* | 107039 | 107375 | NA |
| M0101742 | SEQ. LISTING | 112189 | 113483 | SEQ ID NO: 5 |
| BG550728 | GMGI.071508 | 112663 | 113757 | weakly similar to UniRef100_A7PM60 Cluster: Chromosome chr14 scaffold_21 = whole genome shotgun sequence; n = 1; *Vitis vinifera*|Rep: Chromosome chr14 scaffold_21 = whole genome shotgun sequence - *Vitis vinifera* (Grape) = partial (13%) |
| BG550728 | *Glycine_max_release_2* | 112663 | 113867 | Receptor-like serine/threonine kinase [*Arabidopsis thaliana* (Mouse-ear cress)] |
| CV535605 | *Phaseolus_vulgaris* | 112548 | 113982 | UniRef100_A7PM60 Chromosome chr14 scaffold_21, whole genome shotgun sequence n = 1 Tax = *Vitis vinifera* RepID = A7PM60_VITVI 9.00E−79 |
| M0129138 | SEQ. LISTING | 114532 | 113494 | SEQ ID NO: 6 |
| BU551345 | *Glycine_max_release_2* | 115956 | 116339 | SEQ ID NO: 7 |
| TA58315_3847 | *Glycine_max_release_2* | 118318 | 120087 | NA |
| TC236438 | GMGI.071508 | 118318 | 120087 | NA |
| BE611751 | *Glycine_max_release_2* | 119165 | 119645 | NA |
| BE611751 | GMGI.071508 | 119229 | 119645 | NA |
| TA70371_3847 | *Glycine_max_release_2* | 137417 | 137864 | Hypothetical protein [*Medicago truncatula* (Barrel medic)] |
| TC267549 | GMGI.071508 | 137417 | 137864 | similar to UniRef100_Q9FI64 Cluster: Genomic DNA = chromosome 5 = TAC clone: K21I16; n = 1; *Arabidopsis thaliana*|Rep: Genomic DNA = chromosome 5 = TAC clone: K21I16 - *Arabidopsis thaliana* (Mouse-ear cress) = partial (43%) |
| BG156330 | GMGI.071508 | 155872 | 156903 | similar to UniRef100_A7PM41 Cluster: Chromosome chr14 scaffold_21 = whole genome shotgun sequence; n = 2; *Vitis vinifera*|Rep: Chromosome chr14 scaffold_21 = whole genome shotgun sequence - *Vitis vinifera* (Grape) = partial (23%) |

TABLE 2-continued of the Specification

| Locus/Display Name (1) | Source (2) | Start Base (3) | End Base (4) | ADDITIONAL LOCUS INFORMATION (5) |
|---|---|---|---|---|
| BG156330 | Glycine_max_release_2 | 155872 | 157058 | WD40-like [Medicago truncatula (Barrel medic)] |
| Pvcon10326 | Phaseolus_vulgaris | 155691 | 157835 | UniRef100_A7PM41 Chromosome chr14 scaffold_21, whole genome shotgun sequence n = 1 Tax = Vitis vinifera RepID = A7PM41_VITVI 3.00E−93 |
| CD397113 | Glycine_max_release_2 | 157474 | 157813 | NA |
| TA12653_34305 | Lotus_japonicus_release_1 | 159489 | 161341 | NADP-specific isocitrate dehydrogenase [Lupinus albus (White lupin)] |
| TC27381 | LJGI.070108 | 159489 | 161341 | similar to UniRef100_Q7Y0W7 Cluster: NADP-specific isocitrate dehydrogenase, n = 1, Lupinus albus\|Rep: NADP-specific isocitrate dehydrogenase - Lupinus albus (White lupin), partial (25%) |
| DT084057 | Glycine_soja_release_2 | 161638 | 162192 | NADP-specific isocitrate dehydrogenase [Lupinus albus (White lupin)] |
| BE661051 | Glycine_max_release_2 | 170271 | 172034 | Cyclin-like F-box [Medicago truncatula (Barrel medic)] |
| TA11305_34305 | Lotus_japonicus_release_1 | 170700 | 172307 | Cyclin-like F-box [Medicago truncatula (Barrel medic)] |
| TC34049 | LJGI.070108 | 170700 | 172307 | similar to UniRef100_A7PF14 Cluster: Chromosome chr11 scaffold_13, whole genome shotgun sequence, n = 1, Vitis vinifera\|Rep: Chromosome chr11 scaffold_13, whole genome shotgun sequence - Vitis vinifera (Grape), partial (32%) |
| NP7256876 | MTGI.071708 | 171929 | 173188 | GB\|AC157983.16\|ABE865 10.1 Cyclin-like F-box |
| TA68495_3847 | Glycine_max_release_2 | 194920 | 195696 | Oleosin [Sesamum indicum (Oriental sesame) (Gingelly)] |
| TC265354 | GMGI.071508 | 194920 | 195696 | weakly similar to UniRef100_P29530 Cluster: P24 oleosin isoform A; n = 1; Glycine max\|Rep: P24 oleosin isoform A - Glycine max (Soybean) = partial (40%) |
| BE658264 | Glycine_max_release_2 | 195176 | 195925 | Oleosin [Sesamum indicum (Oriental sesame) (Gingelly)] |
| CV539661 | Phaseolus_vulgaris | 217885 | 218101 | No significant hit (e−20) |
| CA912681 | Phaseolus_coccineus_release_2 | 220374 | 220748 | Arabidopsis thaliana genomic DNA, chromosome 3, P1 clone: MGF10 [Arabidopsis thaliana (Mouse-ear cress)] |
| CA785107 | Glycine_soja_release_2 | 221393 | 221885 | NA |
| TC276537 | GMGI.071508 | 221407 | 222104 | weakly similar to UniRef100_Q4RYK7 Cluster: Chromosome 3 SCAF14975 = whole genome shotgun sequence; n = 1; Tetraodon nigroviridis\|Rep: |

TABLE 2-continued of the Specification

| Locus/Display Name (1) | Source (2) | Start Base (3) | End Base (4) | ADDITIONAL LOCUS INFORMATION (5) |
|---|---|---|---|---|
| | | | | Chromosome 3 SCAF14975 = whole genome shotgun sequence - *Tetraodon nigroviridis* (Green puffer) = partial (21%) |
| TA71044_3847 | *Glycine_max*_release_2 | 221407 | 222133 | NA |
| CD406643 | *Glycine_max*_release_2 | 222113 | 222297 | NA |
| AV416316 | LJGI.070108 | 223773 | 223869 | similar to UniRef100_A7PM35 Cluster: Chromosome chr14 scaffold_21, whole genome shotgun sequence, n = 1, *Vitis vinifera*|Rep: Chromosome chr14 scaffold_21, whole genome shotgun sequence - *Vitis vinifera* (Grape), partial (9%) |
| EC911350 | *Phaseolus_vulgaris* | 224587 | 225958 | UniRef100_A5C233 Putative uncharacterized protein n = 1 Tax = *Vitis vinifera* RepID = A5C233_VITVI 3.00E-77 |
| BU760697 | GMGI.071508 | 224857 | 225965 | similar to UniRef100_A7PM35 Cluster: Chromosome chr14 scaffold_21 = whole genome shotgun sequence; n = 1; *Vitis vinifera*|Rep: Chromosome chr14 scaffold_21 = whole genome shotgun sequence - *Vitis vinifera* (Grape) = partial (22%) |
| BU760697 | *Glycine_max*_release_2 | 224857 | 226145 | Protein At5g19130 [*Arabidopsis thaliana* (Mouse-ear cress)] |
| TC119982 | MTGI.071708 | 224248 | 226812 | Gaa1-like, GPI transamidase component |
| CV541515 | *Phaseolus_vulgaris* | 225934 | 226374 | UniRef100_A7PM35 Chromosome chr14 scaffold_21, whole genome shotgun sequence n = 1 Tax = *Vitis vinifera* RepID = A7PM35_VITVI 2.00E-34 |
| TA76349_3847 | *Glycine_max*_release_2 | 226118 | 226768 | Protein At5g19130 [*Arabidopsis thaliana* (Mouse-ear cress)] |
| TA12045_47247 | *Lotus_corniculatus*_release_1 | 226354 | 226789 | GPAA1-like protein related cluster |
| TA13675_34305 | *Lotus_japonicus*_release_1 | 226354 | 226789 | Protein At5g19130 [*Arabidopsis thaliana* (Mouse-ear cress)] |
| TC29330 | LJGI.070108 | 226354 | 226789 | similar to UniRef100_A7PM35 Cluster: Chromosome chr14 scaffold_21, whole genome shotgun sequence, n = 1, *Vitis vinifera*|Rep: Chromosome chr14 scaffold_21, whole genome shotgun sequence - *Vitis vinifera* (Grape), partial (13%) |
| NP7254537 | MTGI.071708 | 233411 | 237212 | GB|AC152349.11|ABP03404.1 Protein of unknown function DUF266, plant |
| EH256962 | GMGI.071508 | 235306 | 237649 | similar to UniRef100_A7PM54 Cluster: Chromosome chr14 scaffold_21 = whole genome shotgun sequence; |

TABLE 2-continued of the Specification

| Locus/Display Name (1) | Source (2) | Start Base (3) | End Base (4) | ADDITIONAL LOCUS INFORMATION (5) |
|---|---|---|---|---|
| | | | | n = 1; *Vitis vinifera*|Rep: Chromosome chr14 scaffold_21 = whole genome shotgun sequence - *Vitis vinifera* (Grape) = partial (33%) |
| CX708677 | *Glycine_max*_release_2 | 247269 | 248145 | NA |
| BW599077 | LJGI.070108 | 255475 | 261945 | similar to UniRef100_A7QD90 Cluster: Peptidyl-prolyl cis-trans isomerase, n = 1, *Vitis vinifera*|Rep: Peptidyl-prolyl cis-trans isomerase - *Vitis vinifera* (Grape), partial (18%) |
| BW625918 | LJGI.070108 | 257810 | 262980 | similar to UniRef100_Q93YQ8 Cluster: Peptidyl-prolyl cis-trans isomerase, n = 1, *Arabidopsis thaliana*|Rep: Peptidyl-prolyl cis-trans isomerase - *Arabidopsis thaliana* (Mouse-ear cress), partial (32%) |
| DT083826 | *Glycine_soja*_release_2 | 260886 | 261121 | NA |
| CB063628 | GMGI.071508 | 271592 | 271900 | similar to UniRef100_A7PM52 Cluster: Chromosome chr14 scaffold_21 whole genome shotgun sequence; n = 1; *Vitis vinifera*|Rep: = partial (2%) |
| CB063628 | *Glycine_max*_release_2 | 271592 | 271928 | NA |
| TA5835_34305 | *Lotus_japonicus*_release_1 | 273868 | 275906 | Vegetative cell wall protein gp1-like [*Oryza sativa* (*japonica* cultivar-group) |
| TC32024 | LJGI.070108 | 275152 | 275906 | similar to UniRef100_A7PM52 Cluster: Chromosome chr14 scaffold_21, whole genome shotgun sequence, n = 1, *Vitis vinifera*|Rep: Chromosome chr14 scaffold_21, whole genome shotgun sequence - *Vitis vinifera* (Grape), partial (9%) |
| TC252667 | GMGI.071508 | 275739 | 276506 | similar to UniRef100_A7PM52 Cluster: Chromosome chr14 scaffold_21 = whole genome shotgun sequence; n = 1; *Vitis vinifera*|Rep: Chromosome chr14 scaffold_21 = whole genome shotgun sequence - *Vitis vinifera* (Grape) = partial (12%) |
| AW311416 | *Glycine_max*_release_2 | 276269 | 276455 | NA |
| WmFPC_Contig850 | | 99810 | 475910 | NA |
| CV534998 | *Phaseolus_vulgaris* | 288050 | 288585 | UniRef100_A7PM50 Chromosome chr14 scaffold_21, whole genome shotgun sequence n = 1 Tax = *Vitis vinifera* RepID = A7PM50_VITVI 6.00E−39 |
| TA75806_3847 | *Glycine_max*_release_2 | 288290 | 290376 | *Arabidopsis thaliana* genomic DNA = chromosome 3 = P1 clone: MGF10 [*Arabidopsis thaliana* (Mouse-ear cress)] |

TABLE 2-continued of the Specification

| Locus/Display Name (1) | Source (2) | Start Base (3) | End Base (4) | ADDITIONAL LOCUS INFORMATION (5) |
|---|---|---|---|---|
| TC276120 | GMGI.071508 | 288290 | 290376 | similar to UniRef100_A7PM50 Cluster: Chromosome chr14 scaffold_21 = whole genome shotgun sequence; n = 1; *Vitis vinifera*|Rep: Chromosome chr14 scaffold_21 = whole genome shotgun sequence - *Vitis vinifera* (Grape) = partial (62%) |
| BI786388 | GMGI.071508 | 291666 | 292088 | similar to UniRef100_A7PM49 Cluster: Chromosome chr14 scaffold_21 = whole genome shotgun sequence; n = 1; *Vitis vinifera*|Rep: Chromosome chr14 scaffold_21 = whole genome shotgun sequence - *Vitis vinifera* (Grape) = partial (7%) |
| BI786388 | *Glycine_max*_release_2 | 291666 | 292099 | NA |
| TA63308_3847 | *Glycine_max*_release_2 | 291633 | 294397 | NA |
| TC243765 | GMGI.071508 | 293681 | 294426 | weakly similar to UniRef100_Q0JDM0 Cluster: Os04g0394300 protein; n = 1; *Oryza sativa* Japonica Group|Rep: Os04g0394300 protein - *Oryza sativa* subsp. *japonica* (Rice) = partial (3%) |
| TA6412_34305 | *Lotus_japonicus_* release_1 | 293803 | 294412 | NA |
| TC24112 | LJGI.070108 | 293803 | 294412 | NA |
| CA899930 | *Phaseolus_coccineus_* release_2 | 294054 | 294263 | NA |
| TA3887_3886 | *Phaseolus_coccineus_* release_2 | 302301 | 303033 | Hypothetical protein MJH23.3 [*Arabidopsis thaliana* (Mouse-ear cress)] |
| AW705271 | *Glycine_max*_release_2 | 302299 | 303855 | Hypothetical protein MJH23.3 [*Arabidopsis thaliana* (Mouse-ear cress)] |
| TC237313 | GMGI.071508 | 303227 | 306007 | similar to UniRef100_A7PM30 Cluster: Chromosome chr14 scaffold_21 = whole genome shotgun sequence; n = 1; *Vitis vinifera*|Rep: Chromosome chr14 scaffold_21 = whole genome shotgun sequence - *Vitis vinifera* (Grape) = partial (54%) |
| TA61594_3847 | *Glycine_max*_release_2 | 303227 | 306056 | Similarity to RNA binding protein [*Arabidopsis thaliana* (Mouse-ear cress)] |
| asmbl_11859 | *Vigna_unguiculata* | 303952 | 305921 | NA |
| toGm05 | DAGchainer | 30059 | 580791 | Ks0.2335 |
| BU544029 | *Glycine_max*_release_2 | 305220 | 305762 | NA |
| TC23280 | LJGI.070108 | 305373 | 305839 | similar to UniRef100_A7PM30 Cluster: Chromosome chr14 scaffold_21, whole genome shotgun sequence, n = 1, *Vitis vinifera*|Rep: Chromosome chr14 scaffold_21, whole genome shotgun sequence - *Vitis vinifera* (Grape), partial (17%) |

TABLE 2-continued of the Specification

| Locus/Display Name (1) | Source (2) | Start Base (3) | End Base (4) | ADDITIONAL LOCUS INFORMATION (5) |
|---|---|---|---|---|
| AI461058 | Glycine_max_release_2 | 305614 | 305834 | NA |
| BE555571 | Glycine_max_release_2 | 305656 | 306011 | NA |
| NGMAX008197032 | SEQ. LISTING | 314847 | 315148 | SEQ ID NO: 52 |
| asmbl_11860 | Vigna_unguiculata | 319622 | 320527 | NA |
| EV270366 | GMGI.071508 | 319893 | 320575 | similar to UniRef100_P15792 Cluster: Protein kinase PVPK-1; n = 1; *Phaseolus vulgaris*\|Rep: Protein kinase PVPK-1 - *Phaseolus vulgaris* (Kidney bean) (French bean) = partial (34%) |
| J04555 | Phaseolus_vulgaris_release_2 | 318937 | 322709 | Protein kinase PVPK-1 [*Phaseolus vulgaris* (Kidney bean) (French bean)] |
| TA11578_34305 | Lotus_japonicus_release_1 | 320355 | 322024 | Protein kinase PVPK-1 [*Phaseolus vulgaris* (Kidney bean) (French bean)] |
| TC35252 | LJGI.070108 | 320355 | 322381 | homologue to UniRef100_P15792 Cluster: Protein kinase PVPK-1, n = 1, *Phaseolus vulgaris*\|Rep: Protein kinase PVPK-1 - *Phaseolus vulgaris* (Kidney bean) (French bean), partial (48%) |
| Pvcon4227 | Phaseolus_vulgaris | 320098 | 322709 | UniRef100_P15792 Protein kinase PVPK-1 n = 1 Tax = *Phaseolus vulgaris* RepID = KPK1_PHAVU E-0 |
| CA900819 | Phaseolus_coccineus_release_2 | 325129 | 325547 | Sucrase-like protein [*Arabidopsis thaliana* (Mouse-ear cress)] |
| CA900820 | Phaseolus_coccineus_release_2 | 325119 | 328122 | AT3g27570/MMJ24_12 [*Arabidopsis thaliana* (Mouse-ear cress)] |
| TC269193 | GMGI.071508 | 325136 | 329359 | weakly similar to UniRef100_A7PM27 Cluster: Chromosome chr14 scaffold_21 = whole genome shotgun sequence; n = 1; *Vitis vinifera*\|Rep: Chromosome chr14 scaffold_21 = whole genome shotgun sequence - *Vitis vinifera* (Grape) = partial (47%) |
| TA4354_3885 | Phaseolus_vulgaris_release_2 | 325476 | 329154 | AT5g40510/MNF13_30 [*Arabidopsis thaliana* (Mouse-ear cress)] |
| asmbl_11861 | Vigna_unguiculata | 326881 | 329154 | NA |
| CF920945 | Glycine_max_release_2 | 326967 | 329359 | AT3g27570/MMJ24_12 [*Arabidopsis thaliana* (Mouse-ear cress)] |
| SATT723 | | 337605 | 337828 | |
| Satt723 | ePCR | 337605 | 337828 | Map3.0 SSR L/Gm19 cM: 1.5 |
| TC244213 | GMGI.071508 | 354373 | 354996 | similar to UniRef100_A7PL06 Cluster: Chromosome chr7 scaffold_20 = whole genome shotgun sequence; n = 1; *Vitis vinifera*\|Rep: Chromosome chr7 scaffold_20 = whole genome shotgun sequence - *Vitis vinifera* (Grape) = partial (17%) |
| BU090380 | Glycine_max_release_2 | 354683 | 354871 | NA |
| BP058294 | Lotus_japonicus_release_1 | 355950 | 356319 | Protein ycf2 [*Lotus japonicus*] |

TABLE 2-continued of the Specification

| Locus/Display Name (1) | Source (2) | Start Base (3) | End Base (4) | ADDITIONAL LOCUS INFORMATION (5) |
|---|---|---|---|---|
| Pvcon2444 | *Phaseolus_vulgaris* | 354593 | 360732 | UniRef100_A7PL07 Chromosome chr7 scaffold_20, whole genome shotgun sequence n = 1 Tax = *Vitis vinifera* RepID = A7PL07_VITVI 1.00E-144 |
| asmbl_11862 | *Vigna_unguiculata* | 359273 | 359896 | NA |
| CA800649 | *Glycine_max*_release_2 | 377994 | 379933 | AT3g01590/F4P13_13 [*Arabidopsis thaliana* (Mouse-ear cress)] |
| TC245493 | GMGI.071508 | 377994 | 381638 | similar to UniRef100_A7PM21 Cluster: Chromosome chr14 scaffold_21 = whole genome shotgun sequence; n = 1; *Vitis vinifera*\|Rep: Chromosome chr14 scaffold_21 = whole genome shotgun sequence - *Vitis vinifera* (Grape) = partial (96%) |
| CO984617 | *Glycine_max*_release_2 | 379899 | 381537 | At5g14500 [*Arabidopsis thaliana* (Mouse-ear cress)] |
| M0114388 | SEQ. LISTING | 381308 | 380486 | SEQ ID NO: 8 |
| AW704585 | *Glycine_max*_release_2 | 381210 | 381673 | At5g14500 [*Arabidopsis thaliana* (Mouse-ear cress)] |
| TC248588 | GMGI.071508 | 383419 | 383857 | NA |
| asmbl_11863 | *Vigna_unguiculata* | 383428 | 384088 | NA |
| TC126554 | MTGI.071708 | 383593 | 384668 | weakly similar to UniRef100_Q940C3 Cluster: AT3g27530/MMJ24_7, n = 2, *Arabidopsis thaliana*\|Rep: AT3g27530/MMJ24_7 - *Arabidopsis thaliana* (Mouse-ear cress), partial (38%) |
| AJ002216 | *Pisum_sativum*_release_2 | 384088 | 384751 | Emb\|CAA07228.1 [*Arabidopsis thaliana* (Mouse-ear cress)] |
| BI702257 | GMGI.071508 | 384067 | 384789 | similar to UniRef100_Q940C3 Cluster: AT3g27530/MMJ24_7; n = 2; *Arabidopsis thaliana*\|Rep: AT3g27530/MMJ24_7 - *Arabidopsis thaliana* (Mouse-ear cress) = partial (14%) |
| BG451913 | MTGI.071708 | 386353 | 388007 | similar to UniRef100_Q9LT59 Cluster: Emb\|CAA07228.1, n = 1, *Arabidopsis thaliana*\|Rep: Emb\|CAA07228.1 - *Arabidopsis thaliana* (Mouse-ear cress), partial (19%) |
| CV533025 | *Phaseolus_vulgaris* | 388647 | 389345 | UniRef100_UPI000016357E GC6 (GOLGIN CANDIDATE 6) binding/ protein transporter Tax = n = 1 RepID = UPI000016357E 6.00E-27 |
| AV777312 | LJGI.070108 | 389152 | 391279 | similar to UniRef100_Q9LT59 Cluster: Emb\|CAA07228.1, n = 1, *Arabidopsis thaliana*\|Rep: |

TABLE 2-continued of the Specification

| Locus/Display Name (1) | Source (2) | Start Base (3) | End Base (4) | ADDITIONAL LOCUS INFORMATION (5) |
|---|---|---|---|---|
| BM187543 | GMGI.071508 | 394984 | 395407 | Emb|CAA07228.1 - *Arabidopsis thaliana* (Mouse-ear cress), partial (19%) similar to UniRef100_A7PM13 Cluster: Chromosome chr14 scaffold_21 = whole genome shotgun sequence; n = 1; *Vitis vinifera*|Rep: Chromosome chr14 scaffold_21 = whole genome shotgun sequence - *Vitis vinifera* (Grape) = partial (36%) |
| BM187543 | Glycine_max_release_2 | 394984 | 395559 | Gb|AAF01546.1 [*Arabidopsis thaliana* [Mouse-ear cress]] |
| DN652256 | LJGI.070108 | 395487 | 395708 | similar to UniRef100_A7P4B1 Cluster: Chromosome chr1 scaffold_5, whole genome shotgun sequence, n = 1, *Vitis vinifera*|Rep: Chromosome chr1 scaffold_5, whole genome shotgun sequence - *Vitis vinifera* (Grape), partial (19%) |
| DT044393 | Arachis_hypogaea_release_5 | 395462 | 395746 | Cluster: Hypothetical protein T23K23.27, n = 1, *Arabidopsis thaliana*|Rep: Hypothetical protein T23K23.27 - *Arabidopsis thaliana* (Mouse-ear cress) |
| FD789910 | Phaseolus_vulgaris | 395555 | 395927 | UniRef100_A7P4B1 Chromosome chr1 scaffold_5, whole genome shotgun sequence n = 1 Tax = *Vitis vinifera* RepID = A7P4B1_VITVI 2.00E-59 |
| EH259382 | GMGI.071508 | 395577 | 396156 | similar to UniRef100_A7PM13 Cluster: Chromosome chr14 scaffold_21 = whole genome shotgun sequence; n = 1; *Vitis vinifera*|Rep: Chromosome chr14 scaffold_21 = whole genome shotgun sequence - *Vitis vinifera* (Grape) = partial (34%) |
| TA69305_3847 | Glycine_max_release_2 | 403237 | 404175 | NA |
| TC243910 | GMGI.071508 | 403237 | 404175 | similar to UniRef100_A7PM14 Cluster: Chromosome chr14 scaffold_21 = whole genome shotgun sequence; n = 1; *Vitis vinifera*|Rep: Chromosome chr14 scaffold_21 = whole genome shotgun sequence - *Vitis vinifera* (Grape) = partial (5%) |
| CA785084 | Glycine_soja_release_2 | 403526 | 404055 | NA |
| CV541170 | Phaseolus_vulgaris_ | 404688 | 406556 | UniRef100_Q9LT57 Emb|CAB45506.1 n = 1 Tax = *Arabidopsis thaliana* RepID = Q9LT57_ARATH 1.00E-113 |

TABLE 2-continued of the Specification

| Locus/Display Name (1) | Source (2) | Start Base (3) | End Base (4) | ADDITIONAL LOCUS INFORMATION (5) |
|---|---|---|---|---|
| BF071095 | GMGI.071508 | 406510 | 407127 | similar to UniRef100_Q9LT57 Cluster: Emb|CAB45506.1; n = 1; *Arabidopsis thaliana*|Rep: Emb|CAB45506.1 - *Arabidopsis thaliana* (Mouse-ear cress) = partial (8%) |
| BF071095 | *Glycine_max*_release_2 | 406527 | 407127 | NA |
| BM270669 | *Glycine_max*_release_2 | 409910 | 410532 | NA |
| BM270669 | GMGI.071508 | 410045 | 410532 | similar to UniRef100_A7PM16 Cluster: Chromosome chr14 scaffold_21 = whole genome shotgun sequence; n = 1; *Vitis vinifera*|Rep: Chromosome chr14 scaffold_21 = whole genome shotgun sequence - *Vitis vinifera* (Grape) = partial (9%) |
| BG550673 | GMGI.071508 | 421541 | 422250 | similar to UniRef100_A7PM12 Cluster: Chromosome chr14 scaffold_21 = whole genome shotgun sequence; n = 1; *Vitis vinifera*|Rep: Chromosome chr14 scaffold_21 = whole genome shotgun sequence - *Vitis vinifera* (Grape) = partial (26%) |
| BG550673 | *Glycine_max*_release_2 | 421541 | 422354 | Hypothetical protein F18O22_260 [*Arabidopsis thaliana* (Mouse-ear cress)] |
| BU551363 | *Glycine_max*_release_2 | 422150 | 422745 | SEQ ID NO: 9 |
| CD407423 | *Glycine_max*_release_2 | 423719 | 423842 | NA |
| M0205350 | SEQ Listing | 424095 | 423776 | SEQ ID NO: 10 |
| EV270239 | GMGI.071508 | 425649 | 426181 | similar to UniRef100_Q0WVR7 Cluster: TRNA synthase-like protein; n = 1; *Arabidopsis thaliana*|Rep: TRNA synthase-like protein - *Arabidopsis thaliana* (Mouse-ear cress) = partial (5%) |
| BI424448 | GMGI.071508 | 451332 | 451679 | similar to UniRef100_P82353 Cluster: Non-specific lipid-transfer protein 2; n = 1; *Prunus armeniaca*|Rep: Non-specific lipid-transfer protein 2 - *Prunus armeniaca* (Apricot) = partial (68%) |
| TA49179_3847 | *Glycine_max*_release_2 | 451332 | 451827 | Nonspecific lipid-transfer protein 2 [*Prunus armeniaca* (Apricot)] |
| TC252453 | GMGI.071508 | 451397 | 451828 | weakly similar to UniRef100_Q43681 Cluster: Probable non-specific lipid-transfer protein AKCS9 precursor; n = 1; *Vigna unguiculata*|Rep: Probable non-specific lipid-transfer protein AKCS9 precursor - *Vigna unguiculata* (Cowpea) = partial (86%) |
| BE609938 | *Glycine_max*_release_2 | 451607 | 451756 | Probable lipid transfer protein family protein [*Tamarix androssowii*] |

TABLE 2-continued of the Specification

| Locus/Display Name (1) | Source (2) | Start Base (3) | End Base (4) | ADDITIONAL LOCUS INFORMATION (5) |
|---|---|---|---|---|
| BQ612382 | Glycine_max_release_2 | 451777 | 452217 | NA |
| M0102027 | | 466228 | 466889 | SEQ ID NO: 11 |
| Pvcon7917 | Phaseolus_vulgaris | 466120 | 467338 | UniRef100_A5C9E2 Putative uncharacterized protein n = 1 Tax = Vitis vinifera RepID = A5C9E2_VITVI 6.00E−44 |
| asmbl_11864 | Vigna_unguiculata | 467520 | 468191 | NA |
| TA49596_3847 | Glycine_max_release_2 | 470086 | 472059 | Methionine aminopeptidase 2B [Arabidopsis thaliana (Mouse-ear cress)] |
| TC255857 | GMGI.071508 | 470086 | 476828 | homologue to UniRef100_A7PXX3 Cluster: Methionine aminopeptidase; n = 1; Vitis vinifera\|Rep: Methionine aminopeptidase - Vitis vinifera (Grape) = partial (91%) |
| FD792539 | Phaseolus_vulgaris | 472774 | 475674 | UniRef100_A7PXX3 Methionine aminopeptidase n = 1 Tax = Vitis vinifera RepID = A7PXX3_VITVI 5.00E−56 |
| TA3829_3848 | Glycine_soja_release_2 | 471918 | 476623 | Methionine aminopeptidase 2B [Arabidopsis thaliana (Mouse-ear cress)] |
| BU765955 | Glycine_max_release_2 | 472787 | 475846 | Methionine aminopeptidase 2B [Arabidopsis thaliana (Mouse-ear cress)]. SEQ ID NO: 12 |
| EG530516 | Arachis_hypogaea_release_5 | 472835 | 476690 | Cluster: Methionine aminopeptidase 2B, n = 1, Arabidopsis thaliana\|Rep: Methionine aminopeptidase 2B - Arabidopsis thaliana (Mouse-ear cress) |
| AV425234 | LJGI.070108 | 475562 | 475924 | homologue to UniRef100_A7PXX3 Cluster: Methionine aminopeptidase, n = 1, Vitis vinifera\|Rep: Methionine aminopeptidase - Vitis vinifera (Grape), partial (22%) |
| TA49598_3847 | Glycine_max_release_2 | 474794 | 476709 | Methionine aminopeptidase 2B [Arabidopsis thaliana (Mouse-ear cress)] |
| FD797260 | Phaseolus_vulgaris | 475768 | 476654 | UniRef100_A7PXX3 Methionine aminopeptidase n = 1 Tax = Vitis vinifera RepID = A7PXX3_VITVI 6.00E−55 |
| BE823844 | Glycine_max_release_2 | 475751 | 476828 | Methionine aminopeptidase 2B [Arabidopsis thaliana (Mouse-ear cress)] |
| BG726070 | Glycine_max_release_2 | 476668 | 476807 | NA |
| BQ080926 | GMGI.071508 | 480002 | 480636 | similar to UniRef100_A7PY54 Cluster: Chromosome chr15 scaffold_37 = whole genome shotgun sequence; n = 1; Vitis vinifera\|Rep: Chromosome chr15 scaffold_37 = whole genome shotgun sequence - Vitis vinifera (Grape) = partial (39%) |
| TA69442_3847 | Glycine_max_release_2 | 480002 | 481069 | Hypothetical protein F22I13.40 [Arabidopsis thaliana (Mouse-ear cress)] |

TABLE 2-continued of the Specification

| Locus/Display Name (1) | Source (2) | Start Base (3) | End Base (4) | ADDITIONAL LOCUS INFORMATION (5) |
|---|---|---|---|---|
| TC262427 | GMGI.071508 | 480002 | 481069 | similar to UniRef100_A7P8Q6 Cluster: Chromosome chr3 scaffold_8 = whole genome shotgun sequence; n = 1; *Vitis vinifera*|Rep: Chromosome chr3 scaffold_8 = whole genome shotgun sequence - *Vitis vinifera* (Grape) = partial (20%) |
| BU548976 | *Glycine_max_release_2* | 481474 | 481970 | Multi antimicrobial extrusion protein MatE [*Medicago truncatula* (Barrel medic)] |
| CX547082 | *Glycine_max_release_2* | 481345 | 482173 | Multi antimicrobial extrusion protein MatE [*Medicago truncatula* (Barrel medic)] |
| TC236122 | GMGI.071508 | 481300 | 482612 | NA |
| TA57759_3847 | *Glycine_max_release_2* | 481300 | 482627 | Multi antimicrobial extrusion protein MatE [*Medicago truncatula* (Barrel medic)] |
| AV420909 | LJGI.070108 | 481846 | 482201 | weakly similar to UniRef100_A7QTE8 Cluster: Chromosome undetermined scaffold_167, whole genome shotgun sequence, n = 1, *Vitis vinifera*|Rep: Chromosome undetermined scaffold_167, whole genome shotgun sequence - *Vitis vinifera* (Grape), partial (24%) |
| AW597322 | *Glycine_max_release_2* | 481965 | 482825 | Multi antimicrobial extrusion protein MatE [*Medicago truncatula* (Barrel medic)] |
| BM270610 | *Glycine_max_release_2* | 482034 | 483008 | Multi antimicrobial extrusion protein MatE [*Medicago truncatula* (Barrel medic)] |
| BI972603 | GMGI.071508 | 482632 | 483190 | weakly similar to UniRef100_A7P3G6 Cluster: Chromosome chr1 scaffold_5 = whole genome shotgun sequence; n = 1; *Vitis vinifera*|Rep: Chromosome chr1 scaffold_5 = whole genome shotgun sequence - *Vitis vinifera* (Grape) = partial (20%) |
| BI972603 | *Glycine_max_release_2* | 482632 | 484113 | Multi antimicrobial extrusion protein MatE [*Medicago truncatula* (Barrel medic)] |
| TA66198_3847 | *Glycine_max_release_2* | 482595 | 484230 | Multi antimicrobial extrusion protein MatE [*Medicago truncatula* (Barrel medic)] |
| TC253566 | GMGI.071508 | 482648 | 484405 | weakly similar to UniRef100_A7QTE8 Cluster: Chromosome undetermined scaffold_167 = whole genome shotgun sequence; n = 1; *Vitis vinifera*|Rep: Chromosome undetermined scaffold_167 = whole genome shotgun sequence - *Vitis vinifera* (Grape) = partial (44%) |

TABLE 2-continued of the Specification

| Locus/Display Name (1) | Source (2) | Start Base (3) | End Base (4) | ADDITIONAL LOCUS INFORMATION (5) |
|---|---|---|---|---|
| asmbl_11865 | *Vigna_unguiculata* | 482937 | 484289 | NA |
| BG881371 | *Glycine_max_release_2* | 483075 | 484230 | Multi antimicrobial extrusion protein MatE [*Medicago truncatula* (Barrel medic)] |
| WmFPC_Contig7443 | | 384071 | 598745 | NA |
| AW695419 | MTGI.071708 | 491367 | 494466 | similar to UniRef100_A7PU69 Cluster: Chromosome chr7 scaffold_31, whole genome shotgun sequence, n = 1, *Vitis vinifera*|Rep: Chromosome chr7 scaffold_31, whole genome shotgun sequence - *Vitis vinifera* (Grape), partial (11%) |
| BF645755 | MTGI.071708 | 494870 | 497474 | similar to UniRef100_A7PU69 Cluster: Chromosome chr7 scaffold_31, whole genome shotgun sequence, n = 1, *Vitis vinifera*|Rep: Chromosome chr7 scaffold_31, whole genome shotgun sequence - *Vitis vinifera* (Grape), partial (14%) |
| BE475242 | GMGI.071508 | 497000 | 497327 | similar to UniRef100_A7NWE7 Cluster: Chromosome chr5 scaffold_2 whole genome shotgun sequence; n = 1; *Vitis vinifera*|Rep: = partial (1%) |
| BE475242 | *Glycine_max_release_2* | 497000 | 497549 | Hypothetical protein At3g23590/MDB19_8 [*Arabidopsis thaliana* (Mouse-ear cress)] |
| BW611072 | LJGI.070108 | 497387 | 497795 | similar to UniRef100_A7PU69 Cluster: Chromosome chr7 scaffold_31, whole genome shotgun sequence, n = 1, *Vitis vinifera*|Rep: Chromosome chr7 scaffold_31, whole genome shotgun sequence - *Vitis vinifera* (Grape), partial (10%) |
| BQ613050 | *Glycine_max_release_2* | 497409 | 498014 | ORF protein [*Arabidopsis thaliana* (Mouse-ear cress)] |
| CV541244 | *Phaseolus_vulgaris* | 500143 | 500464 | UniRef100_A9PGX2 Putative uncharacterized protein n = 1 Tax = *Populus trichocarpa* RepID = A9PGX2_POPTR 3.00E-28 |
| CX856527 | *Glycine_max_release_2* | 501517 | 501735 | NA |
| BG839076 | *Glycine_max_release_2* | 503126 | 505209 | F2P3.12 protein [*Arabidopsis thaliana* (Mouse-ear cress)] |
| FD790090 | *Phaseolus_vulgaris* | 503370 | 505191 | No significant hit (e-20) |
| TC236383 | GMGI.071508 | 503107 | 505675 | similar to UniRef100_O82505 Cluster: Elongation factor Ts; n = 1; *Arabidopsis thaliana*|Rep: Elongation factor Ts - *Arabidopsis thaliana* (Mouse-ear cress) = partial (32%) |
| TA56246_3847 | *Glycine_max_release_2* | 503107 | 505848 | Ethylene-responsive elongation factor EF-Ts precursor [*Lycopersicon esculentum* (Tomato)] |

TABLE 2-continued of the Specification

| Locus/Display Name (1) | Source (2) | Start Base (3) | End Base (4) | ADDITIONAL LOCUS INFORMATION (5) |
|---|---|---|---|---|
| TC239475 | GMGI.071508 | 503126 | 506560 | similar to UniRef100_Q9SWW0 Cluster: Ethylene-responsive elongation factor EF-Ts precursor; n = 1; *Solanum lycopersicum*|Rep: Ethylene-responsive elongation factor EF-Ts precursor *Solanum lycopersicum* (Tomato) (*Lycopersicon esculentum*) = partial (74%) |
| TA56245_3847 | *Glycine_max_*release_2 | 505512 | 506546 | Ethylene-responsive elongation factor EF-Ts precursor [*Lycopersicon esculentum* (Tomato)] |
| BG839060 | *Glycine_max_*release_2 | 505661 | 506530 | At4g11120 [*Arabidopsis thaliana* (Mouse-ear cress)] |
| CV543527 | *Phaseolus_vulgaris_*release_2 | 508539 | 508771 | Eukaryotic translation initiation factor 5 [*Phaseolus vulgaris* (Kidney bean) (French bean)] |
| CD393454 | *Glycine_max_*release_2 | 510651 | 511000 | Ribosomal protein L22 [*Glycine max* (Soybean)] |
| TC245517 | GMGI.071508 | 510651 | 511270 | homologue to UniRef100_O48879 Cluster: Ribosomal protein L22; n = 1; *Glycine max*|Rep: Ribosomal protein L22 - *Glycine max* (Soybean) = partial (80%) |
| asmbl_11866 | *Vigna_unguiculata* | 510868 | 511269 | NA |
| TA51206_3847 | *Glycine_max_*release_2 | 510702 | 512712 | Ribosomal protein L22 [*Glycine max* (Soybean)] |
| TC249077 | GMGI.071508 | 510771 | 512771 | homologue to UniRef100_O48879 Cluster: Ribosomal protein L22; n = 1; *Glycine max*|Rep: Ribosomal protein L22 - *Glycine max* (Soybean) = partial (98%) |
| BG316244 | *Glycine_max_*release_2 | 511015 | 512722 | Ribosomal protein L22 [*Glycine max* (Soybean)] |
| BQ155270 | MTGI.071708 | 513084 | 514936 | similar to UniRef100_A7PR59 Cluster: Chromosome chr14 scaffold_26, whole genome shotgun sequence, n = 1, *Vitis vinifera*|Rep: Chromosome chr14 scaffold_26, whole genome shotgun sequence - *Vitis vinifera* (Grape), partial (52%) |
| TC30151 | LJGI.070108 | 514647 | 516395 | similar to UniRef100_A7PR59 Cluster: Chromosome chr14 scaffold_26, whole genome shotgun sequence, n = 1, *Vitis vinifera*|Rep: Chromosome chr14 scaffold_26, whole genome shotgun sequence - *Vitis vinifera* (Grape), partial (29%) |
| BP044357 | *Lotus_japonicus_*release_1 | 514647 | 516409 | S-locus protein 8 [*Brassica campestris* (Field mustard)] |
| CB540591 | *Phaseolus_vulgaris* | 514839 | 516355 | No significant hit (e−20) |
| TA65114_3847 | *Glycine_max_*release_2 | 523413 | 524053 | At1g22990/F19G10_22 [*Arabidopsis thaliana* (Mouse-ear cress)] |

TABLE 2-continued of the Specification

| Locus/Display Name (1) | Source (2) | Start Base (3) | End Base (4) | ADDITIONAL LOCUS INFORMATION (5) |
|---|---|---|---|---|
| TC259745 | GMGI.071508 | 523413 | 524067 | similar to UniRef100_A7P3I8 Cluster: Chromosome chr1 scaffold_5 = whole genome shotgun sequence; n = 2; *Vitis vinifera*|Rep: Chromosome chr1 scaffold_5 = whole genome shotgun sequence - *Vitis vinifera* (Grape) = partial (56%) |
| TA4332_47247 | *Lotus_corniculatus_*release_1 | 529321 | 530051 | Actin-11 related cluster |
| TA6031_34305 | *Lotus_japonicus_*release_1 | 529321 | 530051 | Actin [*Striga asiatica*] |
| TC32457 | LJGI.070108 | 529321 | 530051 | homologue to UniRef100_P30167 Cluster: Actin-58, n = 1, *Solanum tuberosum*|Rep: Actin-58 - *Solanum tuberosum* (Potato), partial (39%) |
| AW351005 | *Glycine_max_*release_2 | 529380 | 530095 | Actin [*Striga asiatica*] |
| TA43521_3847 | *Glycine_max_*release_2 | 529306 | 530175 | Actin-11 [*Arabidopsis thaliana* (Mouse-ear cress)] |
| asmbl_11867 | *Vigna_unguiculata* | 529342 | 530189 | NA |
| AU240079 | LJGI.070108 | 529747 | 530013 | homologue to UniRef100_P93372 Cluster: Actin-66, n = 1, *Nicotiana tabacum*|Rep: Actin-66 - *Nicotiana tabacum* (Common tobacco), partial (25%) |
| AU240079 | *Lotus_japonicus_*release_1 | 529747 | 530039 | Actin-11 [*Arabidopsis thaliana* (Mouse-ear cress)] |
| EE127018 | *Arachis_hypogaea_*release_5 | 529933 | 530285 | Cluster: Hypothetical protein, n = 1, *Oryza sativa* (indica cultivar-group)|Rep: Hypothetical protein - *Oryza sativa* subsp. *indica* (Rice) |
| TC240040 | GMGI.071508 | 529306 | 531078 | homologue to UniRef100_P02581 Cluster: Actin-1; n = 1; *Glycine max*|Rep: Actin-1 - *Glycine max* (Soybean) = complete |
| AW666288 | *Glycine_max_*release_2 | 529980 | 530789 | Actin [*Phaseolus acutifolius* (Tepary bean)] |
| TA43509_3847 | *Glycine_max_*release_2 | 529888 | 530911 | Actin [*Glycine max* (Soybean)] |
| TA6074_34305 | *Lotus_japonicus_*release_1 | 530031 | 531095 | Actin-1 [*Sorghum bicolor* (Sorghum) (*Sorghum vulgare*)] |
| TC26188 | LJGI.070108 | 530031 | 531095 | homologue to UniRef100_A1Y2A0 Cluster: Actin, n = 1, *Aegiceras corniculatum*|Rep: Actin - *Aegiceras corniculatum*, partial (81%) |
| BM142797 | *Glycine_max_*release_2 | 530212 | 531095 | Actin [*Trifolium pratense* (Red clover)] |
| BP036880 | *Lotus_japonicus_*release_1 | 530235 | 531095 | Actin/actin-like [*Medicago truncatula* (Barrel medic)] |
| AW349632 | *Glycine_max_*release_2 | 533113 | 533701 | NA |
| AI900119 | *Glycine_max_*release_2 | 533044 | 534995 | NA |
| TA51800_3847 | *Glycine_max_*release_2 | 533054 | 535063 | NA |
| TC241826 | GMGI.071508 | 533055 | 535063 | similar to UniRef100_Q2Z1Y5 Cluster: Pm52 protein; n = 1; *Prunus mume*|Rep: Pm52 protein - *Prunus mume* (Japanese flowering apricot) = partial (73%) |

TABLE 2-continued

| Locus/Display Name (1) | Source (2) | Start Base (3) | End Base (4) | ADDITIONAL LOCUS INFORMATION (5) |
|---|---|---|---|---|
| BU494245 | LJGI.070108 | 533191 | 534994 | weakly similar to UniRef100_Q2Z1Y5 Cluster: Pm52 protein, n = 1, *Prunus mume*|Rep: Pm52 protein - *Prunus mume* (Japanese flowering apricot), partial (59%) |
| AI440735 | *Glycine_max_*release_2 | 534517 | 535020 | NA |
| AI440735 | GMGI.071508 | 534522 | 535020 | similar to UniRef100_Q2Z1Y5 Cluster: Pm52 protein; n = 1; *Prunus mume*|Rep: Pm52 protein - *Prunus mume* (Japanese flowering apricot) = partial (41%) |
| TC250013 | GMGI.071508 | 536842 | 537680 | UniRef100_Q8L7J4 Cluster: Pyruvate kinase; n = 1; *Glycine max*|Rep: Pyruvate kinase - *Glycine max* (Soybean) = partial (29%) |
| TA10574_34305 | *Lotus_japonicus_*release_1 | 537149 | 537628 | Pyruvate kinase [*Glycine max* (Soybean)] |
| TC26632 | LJGI.070108 | 537149 | 537628 | homologue to UniRef100_Q42806 Cluster: Pyruvate kinase, cytosolic isozyme, n = 1, *Glycine max*|Rep: Pyruvate kinase, cytosolic isozyme - *Glycine max* (Soybean), partial (26%) |
| CV536725 | *Phaseolus_vulgaris_*release_2 | 537147 | 537846 | Pyruvate kinase = cytosolic isozyme [*Glycine max* (Soybean)] |
| asmbl_11868 | *Vigna_unguiculata* | 537127 | 538325 | NA |
| TC25282 | LJGI.070108 | 537149 | 538489 | homologue to UniRef100_Q8L7J4 Cluster: Pyruvate kinase, n = 1, *Glycine max*|Rep: Pyruvate kinase - *Glycine max* (Soybean), partial (29%) |
| TA47094_3847 | *Glycine_max_*release_2 | 536842 | 539314 | Pyruvate kinase [*Glycine max* (Soybean)] |
| Pvcon4373 | *Phaseolus_vulgaris* | 537147 | 539113 | UniRef100_Q42806 Pyruvate kinase, cytosolic isozyme n = 1 Tax = *Glycine max* RepID = KPYC_SOYBN E-0 |
| TC124922 | MTGI.071708 | 537491 | 538783 | homologue to UniRef100_Q42806 Cluster: Pyruvate kinase, cytosolic isozyme, n = 1, *Glycine max*|Rep: Pyruvate kinase, cytosolic isozyme - *Glycine max* (Soybean), partial (64%) |
| BF598352 | *Glycine_soja_*release_2 | 538308 | 538971 | Pyruvate kinase [*Citrus sinensis* (Sweet orange)] |
| BG044770 | *Glycine_soja_*release_2 | 538624 | 539149 | Pyruvate kinase [*Citrus sinensis* (Sweet orange)] |
| TC249941 | GMGI.071508 | 538549 | 539314 | UniRef100_Q8L7J4 Cluster: Pyruvate kinase; n = 1; *Glycine max*|Rep: Pyruvate kinase - *Glycine max* (Soybean) = partial (37%) |
| BE608312 | *Glycine_max_*release_2 | 542536 | 544875 | Hypothetical protein [*Arabidopsis thaliana* (Mouse-ear cress)] |
| TC253996 | GMGI.071508 | 542045 | 546856 | similar to UniRef100_A7QNQ5 Cluster: Chromosome undetermined scaffold_133 = whole |

TABLE 2-continued of the Specification

| Locus/Display Name (1) | Source (2) | Start Base (3) | End Base (4) | ADDITIONAL LOCUS INFORMATION (5) |
|---|---|---|---|---|
| | | | | genome shotgun sequence; n = 1; *Vitis vinifera*\|Rep: Chromosome undetermined scaffold_133 = whole genome shotgun sequence - *Vitis vinifera* (Grape) = partial (80%) |
| TC258772 | GMGI.071508 | 548268 | 548805 | NA |
| CV533614 | *Phaseolus_vulgaris* | 548540 | 548638 | No significant hit |
| TA57756_3847 | *Glycine_max*_release_2 | 548268 | 551375 | Putative microtubule-severing protein subunit [*Oryza sativa* (*japonica* cultivar-group)] |
| TC239891 | GMGI.071508 | 548323 | 551375 | similar to UniRef100_A7QNQ6 Cluster: Chromosome undetermined scaffold_133 = whole genome shotgun sequence; n = 1; *Vitis vinifera*\|Rep: Chromosome undetermined scaffold_133 = whole genome shotgun sequence - *Vitis vinifera* (Grape) = partial (12%) |
| EH221990 | GMGI.071508 | 550796 | 551633 | weakly similar to UniRef100_A7QNQ6 Cluster: Chromosome undetermined scaffold_133 = whole genome shotgun sequence; n = 1; *Vitis vinifera*\|Rep: Chromosome undetermined scaffold_133 = whole genome shotgun sequence - *Vitis vinifera* (Grape) = partial (7%) |
| EV263369 | GMGI.071508 | 552842 | 553615 | similar to UniRef100_A8D2Q2 Cluster: ATP synthase protein 8; n = 1; *Caranx ignobilis*\|Rep: ATP synthase protein 8 - *Caranx ignobilis* = partial (37%) |
| BU964969 | *Glycine_max*_release_2 | 556336 | 556943 | NA |
| BU964969 | GMGI.071508 | 556494 | 556943 | similar to UniRef100_Q9MYM4 Cluster: Lysosomal alpha-glucosidase precursor; n = 1; *Bos taurus*\|Rep: Lysosomal alpha-glucosidase = partial (1%) |
| EH221989 | GMGI.071508 | 562783 | 563692 | homologue to UniRef100_A7QNQ6 Cluster: Chromosome undetermined scaffold_133 = whole genome shotgun sequence; n = 1; *Vitis vinifera*\|Rep: Chromosome undetermined scaffold_133 = whole genome shotgun sequence - *Vitis vinifera* (Grape) = partial (3%) |
| AW831441 | GMGI.071508 | 573069 | 573567 | NA |
| AW831441 | *Glycine_max*_release_2 | 573069 | 573639 | NA |
| TA6761_34305 | *Lotus_japonicus_*release_1 | 573706 | 580487 | Sphingosine kinase [*Lotus japonicus*] |
| TC20288 | LJGI.070108 | 573706 | 580487 | UniRef100_Q5KR50 Cluster: Sphingosine kinase, n = 1, *Lotus japonicus*\|Rep: Sphingosine kinase - *Lotus japonicus*, complete |

TABLE 2-continued of the Specification

| Locus/Display Name (1) | Source (2) | Start Base (3) | End Base (4) | ADDITIONAL LOCUS INFORMATION (5) |
|---|---|---|---|---|
| TC122322 | MTGI.071708 | 574490 | 580620 | homologue to UniRef100_Q5KR50 Cluster: Sphingosine kinase, n = 1, *Lotus japonicus*|Rep: Sphingosine kinase - *Lotus japonicus*, partial (66%) |
| BI701010 | *Glycine_max_release_2* | 577145 | 579375 | Sphingosine kinase [*Lotus japonicus*] |
| Pvcon3123 | *Phaseolus_vulgaris* | 577107 | 580468 | UniRef100_Q5KR50 Sphingosine kinase n = 1 Tax = *Lotus japonicus* RepID = Q5KR50_LOTJA E-0 |
| TA49258_3847 | *Glycine_max_release_2* | 579511 | 580791 | Sphingosine kinase [*Lotus japonicus*] |
| TC235674 | GMGI.071508 | 579511 | 580791 | homologue to UniRef100_Q5KR50 Cluster: Sphingosine kinase; n = 1; *Lotus japonicus*|Rep: Sphingosine kinase - *Lotus japonicus* = partial (26%) |
| BI969866 | *Glycine_max_release_2* | 579600 | 580756 | Sphingosine kinase [*Lotus japonicus*] |
| EH043869 | *Arachis_stenosperma_ release_5* | 579729 | 580660 | Cluster: Sphingosine kinase, n = 1, *Lotus japonicus*|Rep: Sphingosine kinase - *Lotus japonicus* |
| BQ786742 | *Glycine_max_release_2* | 580594 | 580719 | NA |
| BM108235 | *Glycine_max_release_2* | 581688 | 582006 | NA |
| AW508189 | *Glycine_max_release_2* | 581725 | 582244 | Hypothetical protein [*Arabidopsis thaliana* (Mouse-ear cress)] |
| TC238711 | GMGI.071508 | 581688 | 582562 | similar to UniRef100_A7QNQ7 Cluster: Chromosome undetermined scaffold_133 = whole genome shotgun sequence; n = 1; *Vitis vinifera*|Rep: Chromosome undetermined scaffold_133 = whole genome shotgun sequence - *Vitis vinifera* (Grape) = partial (50%) |
| TA46155_3847 | *Glycine_max_release_2* | 581745 | 582556 | Hypothetical protein [*Arabidopsis thaliana* (Mouse-ear cress)] |
| AW278369 | GMGI.071508 | 581988 | 582389 | similar to UniRef100_A7QNQ7 Cluster: Chromosome undetermined scaffold_133 = whole genome shotgun sequence; n = 1; *Vitis vinifera*|Rep: Chromosome undetermined scaffold_133 = whole genome shotgun sequence - *Vitis vinifera* (Grape) = partial (44%) |
| AW278369 | *Glycine_max_release_2* | 581988 | 582418 | Hypothetical protein [*Arabidopsis thaliana* (Mouse-ear cress)] |
| CD394810 | *Glycine_max_release_2* | 582134 | 582328 | NA |
| BG047332 | *Glycine_max_release_2* | 591288 | 592013 | OSJNBb0065L13.3 protein [*Oryza sativa (japonica* cultivar-group)] |
| TC272805 | GMGI.071508 | 591358 | 592013 | similar to UniRef100_A7NXM8 Cluster: Chromosome chr5 scaffold_2 = whole genome shotgun sequence; n = 1; *Vitis vinifera*|Rep: |

TABLE 2-continued of the Specification

| Locus/Display Name (1) | Source (2) | Start Base (3) | End Base (4) | ADDITIONAL LOCUS INFORMATION (5) |
|---|---|---|---|---|
| BW599171 | LJGI.070108 | 593399 | 593875 | Chromosome chr5 scaffold_2 = whole genome shotgun sequence - *Vitis vinifera* (Grape) = partial (15%) weakly similar to UniRef100_A7PT63 Cluster: Chromosome chr8 scaffold_29, whole genome shotgun sequence, n = 1, *Vitis vinifera*|Rep: Chromosome chr8 scaffold_29, whole genome shotgun sequence - *Vitis vinifera* (Grape), partial (24%) |
| BE057829 | *Glycine_max*_release_2 | 606858 | 607008 | NA |
| TC275159 | GMGI.071508 | 606858 | 607456 | NA |
| BE612118 | GMGI.071508 | 615853 | 616253 | weakly similar to UniRef100_A7GPV4 Cluster: Citrate transporter; n = 1; *Bacillus cereus* subsp. cytotoxis NVH 391-98|Rep: Citrate transporter - *Bacillus cereus* subsp. cytotoxis (strain NVH 391-98) = partial (5%) |
| BE612118 | *Glycine_max*_release_2 | 615869 | 616269 | NA |
| CA910895 | *Phaseolus_coccineus*_release_2 | 622174 | 622531 | *Arabidopsis thaliana* genomic DNA, chromosome 5, P1 clone: MPO12 [*Arabidopsis thaliana* (Mouse-ear cress)] |
| BU763992 | *Glycine_max*_release_2 | 625192 | 625591 | NA |
| TA51978_3847 | *Glycine_max*_release_2 | 625330 | 626304 | Putative ethylene-responsive protein [*Oryza sativa* (*japonica* cultivar-group)] |
| TC236117 | GMGI.071508 | 625330 | 626304 | similar to UniRef100_A7PM86 Cluster: Chromosome chr14 scaffold_21 = whole genome shotgun sequence; n = 1; *Vitis vinifera*|Rep: Chromosome chr14 scaffold_21 = whole genome shotgun sequence - *Vitis vinifera* (Grape) = partial (43%) |
| TC263881 | GMGI.071508 | 625192 | 627651 | similar to UniRef100_A7PM86 Cluster: Chromosome chr14 scaffold_21 = whole genome shotgun sequence; n = 1; *Vitis vinifera*|Rep: Chromosome chr14 scaffold_21 = whole genome shotgun sequence - *Vitis vinifera* (Grape) = partial (76%) |
| TA51979_3847 | *Glycine_max*_release_2 | 625252 | 627642 | Putative ethylene response protein [*Capsicum chinense* (Scotch bonnet) (Bonnet pepper)] |
| TC236300 | GMGI.071508 | 625318 | 627642 | similar to UniRef100_A7PM86 Cluster: Chromosome chr14 scaffold_21 = whole genome shotgun sequence; n = 1; *Vitis vinifera*|Rep: Chromosome chr14 scaffold_21 = whole genome shotgun sequence - *Vitis vinifera* (Grape) = partial (98%) |

TABLE 2-continued of the Specification

| Locus/Display Name (1) | Source (2) | Start Base (3) | End Base (4) | ADDITIONAL LOCUS INFORMATION (5) |
|---|---|---|---|---|
| CA910548 | *Phaseolus_coccineus_release_2* | 625559 | 627607 | Putative ethylene response protein [*Capsicum chinense* (Scotch bonnet) (Bonnet pepper)] |
| Pvcon5808 | *Phaseolus_vulgaris* | 625567 | 627610 | UniRef100_A7PM86 Chromosome chr14 scaffold_21, whole genome shotgun sequence n = 1 Tax = *Vitis vinifera* RepID = A7PM86_VITVI 2.00E−77 |
| EV269595 | GMGI.071508 | 627204 | 627569 | similar to UniRef100_A7PM86 Cluster: Chromosome chr14 scaffold_21 = whole genome shotgun sequence; n = 1; *Vitis vinifera*|Rep: Chromosome chr14 scaffold_21 = whole genome shotgun sequence - *Vitis vinifera* (Grape) = partial (29%) |
| BI273677 | *Glycine_max_release_2* | 637550 | 637816 | NA |
| BP049107 | *Lotus_corniculatus_release_1* | 647584 | 649419 | Cinnamoyl CoA reductase-like protein related cluster |
| TC258382 | GMGI.071508 | 646415 | 652371 | weakly similar to UniRef100_A7PM88 Cluster: Chromosome chr14 scaffold_21 = whole genome shotgun sequence; n = 1; *Vitis vinifera*|Rep: Chromosome chr14 scaffold_21 = whole genome shotgun sequence - *Vitis vinifera* (Grape) = partial (72%) |
| TA50222_3847 | *Glycine_max_release_2* | 646722 | 652222 | Cinnamoyl CoA reductase-like protein [*Arabidopsis thaliana* (Mouse-ear cress)] |
| SATT495 | | 650288 | 650531 | |
| Satt495 | ePCR | 650288 | 650531 | Map3.0 SSR L/Gm19 cM: 2.7 |
| AW099618 | GMGI.071508 | 649276 | 652222 | weakly similar to UniRef100_A7PM88 Cluster: Chromosome chr14 scaffold_21 = whole genome shotgun sequence; n = 1; *Vitis vinifera*|Rep: Chromosome chr14 scaffold_21 = whole genome shotgun sequence - *Vitis vinifera* (Grape) = partial (23%) |
| TA50296_3847 | *Glycine_max_release_2* | 674409 | 676421 | NA |
| BQ629031 | *Glycine_max_release_2* | 674669 | 676494 | NA |
| BM520842 | *Glycine_soja_release_2* | 674685 | 676538 | NA |
| TC264557 | GMGI.071508 | 674741 | 676494 | NA |
| BU765059 | *Glycine_max_release_2* | 674828 | 676698 | NA |
| BU765059 | GMGI.071508 | 674925 | 676698 | weakly similar to UniRef100_A7L4B0 Cluster: Protein kinase; n = 1; *Carica papaya*|Rep: Protein kinase *Carica papaya* (Papaya) = partial (6%) |
| TC264815 | GMGI.071508 | 674409 | 678111 | weakly similar to UniRef100_A7L4B0 Cluster: Protein kinase; n = 1; *Carica papaya*|Rep: Protein kinase - *Carica papaya* (Papaya) = partial (14%) |
| asmbl_11869 | *Vigna_unguiculata* | 676473 | 676672 | NA |
| TA50295_3847 | *Glycine_max_release_2* | 674775 | 678957 | NA |

TABLE 2-continued of the Specification

| Locus/Display Name (1) | Source (2) | Start Base (3) | End Base (4) | ADDITIONAL LOCUS INFORMATION (5) |
|---|---|---|---|---|
| Pvcon1987 | *Phaseolus_vulgaris* | 674506 | 679702 | UniRef100_A7L4B0 Protein kinase n = 1 Tax = *Carica papaya* RepID = A7L4B0_CARPA 1.00E−127 |
| BM528477 | Glycine_max_release_2 | 676507 | 678111 | NA |
| TA11531_47247 | Lotus_corniculatus_ release_1 | 676692 | 678714 | Protein kinase-like protein related cluster |
| TA13031_34305 | Lotus_japonicus_ release_1 | 676692 | 678714 | Hypothetical protein At5g14720 [*Arabidopsis thaliana* (Mouse-ear cress)] |
| TC31122 | LJGI.070108 | 676701 | 678714 | similar to UniRef100_A7L4B0 Cluster: Protein kinase, n = 1, *Carica papaya*\|Rep: Protein kinase - *Carica papaya* (Papaya), partial (14%) |
| TC255388 | GMGI.071508 | 679127 | 681361 | homologue to UniRef100_A7PM90 Cluster: Chromosome chr14 scaffold_21 = whole genome shotgun sequence; n = 1; *Vitis vinifera*\|Rep: Chromosome chr14 scaffold_21 = whole genome shotgun sequence - *Vitis vinifera* (Grape) = partial (44%) |
| TC124284 | MTGI.071708 | 679117 | 681419 | homologue to UniRef100_A7PM90 Cluster: Chromosome chr14 scaffold_21, whole genome shotgun sequence, n = 1, *Vitis vinifera*\|Rep: Chromosome chr14 scaffold_21, whole genome shotgun sequence - *Vitis vinifera* (Grape), partial (48%) |
| DV565290 | *Phaseolus_vulgaris* | 681368 | 681460 | No significant hit (e−20) |
| toGm05 | DAGchainer | 603011 | 803108 | Ks0.2166 |
| NP7265365 | MTGI.071708 | 703588 | 713159 | GB\|AC124951.19\|ABE84834.1 ATPase, E1-E2 type, Peptidase M, neutral zinc metallopeptidases, zinc-binding site |
| BF325038 | Glycine_max_release_2 | 711165 | 712911 | ATPase = E1-E2 type; Peptidase M = neutral zinc metallopeptidases = zinc-binding site [*Medicago truncatula* (Barrel medic)] |
| FE897117 | *Phaseolus_vulgaris* | 715539 | 715874 | UniRef100_Q93VL6 NBS-LRR resistance-like protein J78 n = 1 Tax = *Phaseolus vulgaris* RepID = Q93VL6_PHAVU 2.00E−47 |
| TC264844 | GMGI.071508 | 731939 | 732440 | weakly similar to UniRef100_A7PD05 Cluster: Chromosome chr17 scaffold_12 = whole genome shotgun sequence; n = 1; *Vitis vinifera*\|Rep: Chromosome chr17 scaffold_12 = whole genome shotgun sequence - *Vitis vinifera* (Grape) = partial (13%) |
| TA67235_3847 | Glycine_max_release_2 | 731939 | 733078 | NA |
| CD404253 | GMGI.071508 | 732439 | 733078 | homologue to UniRef100_A7PM92 Cluster: Chromosome chr14 scaffold_21 = whole genome shotgun sequence; |

TABLE 2-continued of the Specification

| Locus/Display Name (1) | Source (2) | Start Base (3) | End Base (4) | ADDITIONAL LOCUS INFORMATION (5) |
|---|---|---|---|---|
| | | | | n = 1; *Vitis vinifera*|Rep: Chromosome chr14 scaffold_21 = whole genome shotgun sequence - *Vitis vinifera* (Grape) = partial (8%) |
| BU091162 | GMGI.071508 | 737876 | 738292 | NA |
| BU091162 | *Glycine_max*_release_2 | 737876 | 738363 | NA |
| asmbl_11870 | *Vigna_unguiculata* | 740144 | 741401 | NA |
| BI470779 | GMGI.071508 | 740189 | 741746 | similar to UniRef100_Q9XQB0 Cluster: Carbonic anhydrase; n = 1; *Vigna radiata* var. *radiata*|Rep: Carbonic anhydrase - *Phaseolus aureus* (Mung bean) (*Vigna radiata*) = partial (30%) |
| TA43150_3847 | *Glycine_max*_release_2 | 740126 | 742524 | Carbonic anhydrase [*Phaseolus aureus* (Mung bean) (*Vigna radiata*)] |
| BG509786 | GMGI.071508 | 740265 | 742434 | homologue to UniRef100_Q9XQB0 Cluster: Carbonic anhydrase; n = 1; *Vigna radiata* var. *radiata*|Rep: Carbonic anhydrase - *Phaseolus aureus* (Mung bean) (*Vigna radiata*) = partial (34%) |
| BG509786 | *Glycine_max*_release_2 | 740265 | 742656 | Carbonic anhydrase [*Zea mays* (Maize)] |
| DT083317 | *Glycine_soja*_release_2 | 740299 | 742670 | Carbonic anhydrase [*Zea mays* (Maize)] |
| AW781596 | *Glycine_max*_release_2 | 740182 | 742860 | Carbonic anhydrase [*Phaseolus aureus* (Mung bean) (*Vigna radiata*)] |
| BU089680 | *Glycine_max*_release_2 | 741070 | 742671 | Carbonic anhydrase [*Zea mays* (Maize)] |
| BM887226 | *Glycine_max*_release_2 | 741037 | 742852 | Carbonic anhydrase [*Zea mays* (Maize)] |
| BU089600 | *Glycine_max*_release_2 | 741070 | 742891 | Carbonic anhydrase [*Zea mays* (Maize)] |
| TC23104 | LJGI.070108 | 740127 | 744319 | similar to UniRef100_Q9XQB0 Cluster: Carbonic anhydrase, n = 1, *Vigna radiata* var. *radiata*|Rep: Carbonic anhydrase - *Phaseolus aureus* (Mung bean) (*Vigna radiata*), partial (98%) |
| TA2934_3885 | *Phaseolus_vulgaris*_release_2 | 739932 | 744687 | Carbonic anhydrase [*Zea mays* (Maize)] |
| TC238511 | GMGI.071508 | 740118 | 744639 | homologue to UniRef100_Q9XQB0 Cluster: Carbonic anhydrase; n = 1; *Vigna radiata* var. *radiata*|Rep: Carbonic anhydrase - *Phaseolus aureus* (Mung bean) (*Vigna radiata*) = complete |
| TA377_34305 | *Lotus_japonicus*_release_1 | 740127 | 744704 | Carbonic anhydrase [*Zea mays* (Maize)] |
| Pvcon229 | *Phaseolus_vulgaris* | 740125 | 744728 | UniRef100_Q9XQB0 Carbonic anhydrase n = 1 Tax = *Vigna radiata* var. *radiata* RepID = Q9XQB0_PHAAU 1.00E-176 |

TABLE 2-continued of the Specification

| Locus/Display Name (1) | Source (2) | Start Base (3) | End Base (4) | ADDITIONAL LOCUS INFORMATION (5) |
|---|---|---|---|---|
| TA2935_3885 | *Phaseolus_vulgaris_ release_2* | 740178 | 744687 | Carbonic anhydrase [*Zea mays* (Maize)] |
| TA2376_3848 | *Glycine_soja_ release_2* | 740118 | 744805 | Carbonic anhydrase [*Phaseolus aureus* (Mung bean) (*Vigna radiata*)] |
| TA43157_3847 | *Glycine_max_release_2* | 740117 | 744844 | Carbonic anhydrase [*Zea mays* (Maize)] |
| TA43160_3847 | *Glycine_max_release_2* | 741051 | 744186 | Carbonic anhydrase = chloroplast precursor (EC 4.2.1.1) (Carbonate dehydratase) [Contains: Carbonic anhydrase = 27 kDa isoform; Carbonic anhydrase = 25 kDa isoform] [*Pisum sativum* (Garden pea)] |
| TC135779 | MTGI.071708 | 741364 | 744530 | homologue to UniRef100_P17067 Cluster: Carbonic anhydrase, chloroplast precursor (Carbonate dehydratase) [Contains: Carbonic anhydrase, 27 kDa isoform, Carbonic anhydrase, 25 kDa isoform], n = 1, *Pisum sativum*\|Rep: Carbonic anhydrase, chloroplast precursor (Carbonate dehydratase) [Contains: Carbonic anhydrase, 27 kDa isoform, Carbonic anhydrase, 25 kDa isoform] - *Pisum sativum* (Garden pea), partial (79%) |
| TA4174_3848 | *Glycine_soja_ release_2* | 742624 | 743398 | Carbonic anhydrase [*Phaseolus aureus* (Mung bean) (*Vigna radiata*)] |
| Pvcon228 | *Phaseolus_vulgaris* | 741374 | 744687 | UniRef100_Q9XQB0 Carbonic anhydrase n = 1 Tax = *Vigna radiata* var. *radiata* RepID = Q9XQB0_PHAAU 1.00E−137 |
| TA43163_3847 | *Glycine_max_release_2* | 741381 | 744770 | Carbonic anhydrase [*Zea mays* (Maize)] |
| TC247359 | GMGI.071508 | 741381 | 744770 | homologue to UniRef100_Q9XQB0 Cluster: Carbonic anhydrase; n = 1; *Vigna radiata* var. *radiata*\|Rep: Carbonic anhydrase - *Phaseolus aureus* (Mung bean) (*Vigna radiata*) = partial (62%) |
| BG045644 | *Glycine_soja_ release_2* | 742643 | 743622 | Carbonic anhydrase = chloroplast precursor (EC 4.2.1.1) (Carbonate dehydratase) [Contains: Carbonic anhydrase = 27 kDa isoform; Carbonic anhydrase = 25 kDa isoform] [*Pisum sativum* (Garden pea)] |
| Pvcon227 | *Phaseolus_vulgaris* | 741681 | 744687 | UniRef100_Q9XQB0 Carbonic anhydrase n = 1 Tax = *Vigna radiata* var. *radiata* RepID = Q9XQB0_PHAAU 1.00E−133 |

TABLE 2-continued of the Specification

| Locus/Display Name (1) | Source (2) | Start Base (3) | End Base (4) | ADDITIONAL LOCUS INFORMATION (5) |
|---|---|---|---|---|
| TC124201 | MTGI.071708 | 741922 | 744665 | homologue to UniRef100_P17067 Cluster: Carbonic anhydrase, chloroplast precursor (Carbonate dehydratase) [Contains: Carbonic anhydrase, 27 kDa isoform, Carbonic anhydrase, 25 kDa isoform], n = 1, *Pisum sativum*|Rep: Carbonic anhydrase, chloroplast precursor (Carbonate dehydratase) [Contains: Carbonic anhydrase, 27 kDa isoform, Carbonic anhydrase, 25 kDa isoform] - *Pisum sativum* (Garden pea), partial (57%) |
| CB543710 | *Phaseolus_vulgaris_*release_2 | 742464 | 744532 | Carbonic anhydrase [*Phaseolus aureus* (Mung bean) (*Vigna radiata*)] |
| CB539509 | *Phaseolus_vulgaris_*release_2 | 742480 | 744557 | Carbonic anhydrase [*Zea mays* (Maize)] |
| TC126947 | MTGI.071708 | 742434 | 744665 | homologue to UniRef100_P17067 Cluster: Carbonic anhydrase, chloroplast precursor (Carbonate dehydratase) [Contains: Carbonic anhydrase, 27 kDa isoform, Carbonic anhydrase, 25 kDa isoform], n = 1, *Pisum sativum*|Rep: Carbonic anhydrase, chloroplast precursor (Carbonate dehydratase) [Contains: Carbonic anhydrase, 27 kDa isoform, Carbonic anhydrase, 25 kDa isoform] - *Pisum sativum* (Garden pea), partial (51%) |
| asmbl_11871 | *Vigna_unguiculata* | 742823 | 744369 | NA |
| asmbl_11872 | *Vigna_unguiculata* | 742628 | 744687 | NA |
| asmbl_11874 | *Vigna_unguiculata* | 742641 | 744687 | NA |
| TA43165_3847 | *Glycine_max_*release_2 | 742658 | 744772 | Carbonic anhydrase [*Phaseolus aureus* (Mung bean) (*Vigna radiata*)] |
| TC241035 | GMGI.071508 | 742658 | 744772 | homologue to UniRef100_Q9XQB0 Cluster: Carbonic anhydrase; n = 1; *Vigna radiata* var. *radiata*|Rep: Carbonic anhydrase - *Phaseolus aureus* (Mung bean) (*Vigna radiata*) = partial (38%) |
| TA480_3888 | *Pisum_sativum_*release_2 | 742823 | 744641 | Carbonic anhydrase, chloroplast precursor (EC 4.2.1.1) (Carbonate dehydratase) [Contains: Carbonic anhydrase, 27 kDa isoform, Carbonic anhydrase, 25 kDa isoform] [*Pisum sativum* (Garden pea)] |

TABLE 2-continued of the Specification

| Locus/Display Name (1) | Source (2) | Start Base (3) | End Base (4) | ADDITIONAL LOCUS INFORMATION (5) |
|---|---|---|---|---|
| TC240357 | GMGI.071508 | 742650 | 744828 | homologue to UniRef100_Q9XQB0 Cluster: Carbonic anhydrase; n = 1; *Vigna radiata* var. *radiata*\|Rep: Carbonic anhydrase - *Phaseolus aureus* (Mung bean) (*Vigna radiata*) = partial (38%) |
| BE346766 | *Glycine_max_*release_2 | 743636 | 744227 | Carbonic anhydrase = chloroplast precursor (EC 4.2.1.1) (Carbonate dehydratase) [Contains: Carbonic anhydrase = 27 kDa isoform; Carbonic anhydrase = 25 kDa isoform] [*Pisum sativum* (Garden pea)] |
| AW596246 | *Glycine_max_*release_2 | 743636 | 744243 | Carbonic anhydrase [*Phaseolus aureus* (Mung bean) (*Vigna radiata*)] |
| BE807206 | *Glycine_max_*release_2 | 743636 | 744244 | Carbonic anhydrase [*Phaseolus aureus* (Mung bean) (*Vigna radiata*)] |
| CB280659 | *Phaseolus_vulgaris_*release_2 | 743613 | 744419 | Carbonic anhydrase [*Phaseolus aureus* (Mung bean) (*Vigna radiata*)] |
| asmbl_11875 | *Vigna_unguiculata* | 743587 | 744642 | NA |
| DT083076 | *Glycine_soja_*release_2 | 743565 | 744678 | Carbonic anhydrase [*Phaseolus aureus* (Mung bean) (*Vigna radiata*)] |
| TC29040 | LJGI.070108 | 743565 | 744702 | similar to UniRef100_Q9XQB0 Cluster: Carbonic anhydrase, n = 1, *Vigna radiata* var. *radiata*\|Rep: Carbonic anhydrase - *Phaseolus aureus* (Mung bean) (*Vigna radiata*), partial (31%) |
| TA134_47247 | *Lotus_corniculatus_*release_1 | 743568 | 744704 | Carbonic anhydrase related cluster |
| TA378_34305 | *Lotus_japonicus_*release_1 | 743568 | 744704 | Carbonic anhydrase, prokaryotic and plant [*Medicago truncatula* (Barrel medic)] |
| TC24201 | LJGI.070108 | 743584 | 744704 | similar to UniRef100_Q9XQB0 Cluster: Carbonic anhydrase, n = 1, *Vigna radiata* var. *radiata*\|Rep: Carbonic anhydrase - *Phaseolus aureus* (Mung bean) (*Vigna radiata*), partial (25%) |
| CB539196 | *Phaseolus_vulgaris_*release_2 | 743626 | 744687 | Carbonic anhydrase [*Phaseolus aureus* (Mung bean) (*Vigna radiata*)] |
| AV413187 | LJGI.070108 | 744089 | 744647 | similar to UniRef100_P27140 Cluster: Carbonic anhydrase, chloroplast precursor, n = 4, *Arabidopsis thaliana*\|Rep: Carbonic anhydrase, chloroplast precursor - *Arabidopsis thaliana* (Mouse-ear cress), partial (17%) |
| AV413187 | *Lotus_japonicus_*release_1 | 744089 | 744672 | Carbonic anhydrase, chloroplast precursor [*Arabidopsis thaliana* (Mouse-ear cress)] |

TABLE 2-continued of the Specification

| Locus/Display Name (1) | Source (2) | Start Base (3) | End Base (4) | ADDITIONAL LOCUS INFORMATION (5) |
|---|---|---|---|---|
| CD860850 | *Pisum_sativum_release_2* | 744145 | 744641 | Carbonic anhydrase, chloroplast precursor [*Arabidopsis thaliana* (Mouse-ear cress)] |
| CD403834 | *Glycine_max_release_2* | 744076 | 744732 | Carbonic anhydrase = chloroplast precursor [*Arabidopsis thaliana* (Mouse-ear cress)] |
| CD415400 | *Glycine_max_release_2* | 744251 | 744691 | NA |
| asmbl_11873 | *Vigna_unguiculata* | 744448 | 744649 | NA |
| CB541850 | *Phaseolus_vulgaris* | 747218 | 747570 | No significant hit (e−20) |
| BM953717 | *Glycine_max_release_2* | 747199 | 748912 | Peptidase S1 and S6 = chymotrypsin/Hap [*Medicago truncatula* (Barrel medic)] |
| EH256926 | GMGI.071508 | 747192 | 749279 | homologue to UniRef100_A7Q7E6 Cluster: Chromosome chr18 scaffold_59 = whole genome shotgun sequence; n = 1; *Vitis vinifera*|Rep: Chromosome chr18 scaffold_59 = whole genome shotgun sequence - *Vitis vinifera* (Grape) = partial (21%) |
| TA51716_3847 | *Glycine_max_release_2* | 747191 | 749327 | Putative DegP protease [*Oryza sativa* (*japonica* cultivar-group)] |
| TC243148 | GMGI.071508 | 747199 | 749327 | homologue to UniRef100_A7Q7E6 Cluster: Chromosome chr18 scaffold_59 = whole genome shotgun sequence; n = 1; *Vitis vinifera*|Rep: Chromosome chr18 scaffold_59 = whole genome shotgun sequence - *Vitis vinifera* (Grape) = partial (25%) |
| AV768772 | LJGI.070108 | 747281 | 749288 | homologue to UniRef100_O22609 Cluster: Protease Do-like 1, chloroplast precursor, n = 1, *Arabidopsis thaliana*|Rep: Protease Do-like 1, chloroplast precursor - *Arabidopsis thaliana* (Mouse-ear cress), partial (23%) |
| BE807421 | *Glycine_max_release_2* | 748776 | 749688 | Peptidase S1 and S6 = chymotrypsin/Hap [*Medicago truncatula* (Barrel medic)] |
| TA51715_3847 | *Glycine_max_release_2* | 747251 | 752927 | Peptidase S1 and S6 = chymotrypsin/Hap [*Medicago truncatula* (Barrel medic)] |
| TC260884 | GMGI.071508 | 747251 | 752942 | homologue to UniRef100_A7Q7E6 Cluster: Chromosome chr18 scaffold_59 = whole genome shotgun sequence; n = 1; *Vitis vinifera*|Rep: Chromosome chr18 scaffold_59 = whole genome shotgun sequence - *Vitis vinifera* (Grape) = partial (80%) |
| BE474482 | *Glycine_max_release_2* | 751068 | 752387 | Peptidase S1 and S6 = chymotrypsin/Hap [*Medicago truncatula* (Barrel medic)] |

TABLE 2-continued of the Specification

| Locus/Display Name (1) | Source (2) | Start Base (3) | End Base (4) | ADDITIONAL LOCUS INFORMATION (5) |
|---|---|---|---|---|
| BE474482 | GMGI.071508 | 751070 | 752387 | homologue to UniRef100_A7Q7E6 Cluster: Chromosome chr18 scaffold_59 = whole genome shotgun sequence; n = 1; *Vitis vinifera*|Rep: Chromosome chr18 scaffold_59 = whole genome shotgun sequence - *Vitis vinifera* (Grape) = partial (19%) |
| TC261290 | GMGI.071508 | 755656 | 757218 | similar to UniRef100_A7PM96 Cluster: Chromosome chr14 scaffold_21 = whole genome shotgun sequence; n = 1; *Vitis vinifera*|Rep: Chromosome chr14 scaffold_21 = whole genome shotgun sequence - *Vitis vinifera* (Grape) = partial (33%) |
| BG646067 | MTGI.071708 | 756996 | 759297 | similar to UniRef100_A7PM96 Cluster: Chromosome chr14 scaffold_21, whole genome shotgun sequence, n = 1, *Vitis vinifera*|Rep: Chromosome chr14 scaffold_21, whole genome shotgun sequence - *Vitis vinifera* (Grape), partial (33%) |
| BE555567 | *Glycine_max*_release_2 | 757210 | 762134 | Hypothetical protein [*Medicago truncatula* (Barrel medic)] |
| BE555567 | GMGI.071508 | 757746 | 762134 | similar to UniRef100_A7PM96 Cluster: Chromosome chr14 scaffold_21 = whole genome shotgun sequence; n = 1; *Vitis vinifera*|Rep: Chromosome chr14 scaffold_21 = whole genome shotgun sequence - *Vitis vinifera* (Grape) = partial (31%) |
| BE058948 | *Glycine_max*_release_2 | 762117 | 763784 | Hypothetical protein [*Medicago truncatula* (Barrel medic)] |
| BE058948 | GMGI.071508 | 762818 | 763784 | similar to UniRef100_A7PM96 Cluster: Chromosome chr14 scaffold_21 = whole genome shotgun sequence; n = 1; *Vitis vinifera*|Rep: Chromosome chr14 scaffold_21 = whole genome shotgun sequence - *Vitis vinifera* (Grape) = partial (25%) |
| TC138874 | MTGI.071708 | 768876 | 770881 | similar to UniRef100_Q40318 Cluster: Coil protein, n = 1, *Medicago sativa*|Rep: Coil protein - *Medicago sativa* (Alfalfa), partial (60%) |

TABLE 2-continued of the Specification

| Locus/Display Name (1) | Source (2) | Start Base (3) | End Base (4) | ADDITIONAL LOCUS INFORMATION (5) |
|---|---|---|---|---|
| TC124470 | MTGI.071708 | 768770 | 771318 | similar to UniRef100_Q1RU40 Cluster: Lipolytic enzyme, G-D-S-L, n = 1, *Medicago truncatula*\|Rep: Lipolytic enzyme, G-D-S-L - *Medicago truncatula* (Barrel medic), partial (77%) |
| TC268582 | GMGI.071508 | 768733 | 771727 | weakly similar to UniRef100_A7PMA0 Cluster: Chromosome chr14 scaffold_21 = whole genome shotgun sequence; n = 1; *Vitis vinifera*\|Rep: Chromosome chr14 scaffold_21 = whole genome shotgun sequence - *Vitis vinifera* (Grape) = partial (89%) |
| BE059369 | *Glycine_max_release_2* | 770328 | 771326 | Lipolytic enzyme = G-D-S-L [*Medicago truncatula* (Barrel medic)] |
| BE329784 | GMGI.071508 | 770783 | 771236 | similar to UniRef100_Q1RU40 Cluster: Lipolytic enzyme = G-D-S-L; n = 1; *Medicago truncatula*\|Rep: Lipolytic enzyme = G-D-S-L - *Medicago truncatula* (Barrel medic) = partial (27%) |
| BE329784 | *Glycine_max_release_2* | 770783 | 771288 | Lipolytic enzyme = G-D-S-L [*Medicago truncatula* (Barrel medic)] |
| TA68573_3847 | *Glycine_max_release_2* | 773983 | 774836 | Putative kinesin light chain [*Oryza sativa* (japonica cultivar-group)] |
| TC259227 | GMGI.071508 | 773983 | 774836 | similar to UniRef100_A7PD12 Cluster: Chromosome chr17 scaffold_12 = whole genome shotgun sequence; n = 1; *Vitis vinifera*\|Rep: Chromosome chr17 scaffold_12 = whole genome shotgun sequence - *Vitis vinifera* (Grape) = partial (13%) |
| AI759741 | *Glycine_max_release_2* | 774118 | 774822 | Putative kinesin light chain [*Oryza sativa* (japonica cultivar-group)] |
| asmbl_11876 | *Vigna_unguiculata* | 774030 | 774978 | NA |
| TC139308 | MTGI.071708 | 774935 | 775598 | similar to UniRef100_A7PMA1 Cluster: Chromosome chr14 scaffold_21, whole genome shotgun sequence, n = 1, *Vitis vinifera*\|Rep: Chromosome chr14 scaffold_21, whole genome shotgun sequence - *Vitis vinifera* (Grape), partial (34%) |
| AW186182 | *Glycine_max_release_2* | 775276 | 775796 | Similarity to kinesin light chain [*Arabidopsis thaliana* (Mouse-ear cress)] |
| AW186182 | GMGI.071508 | 775464 | 775796 | similar to UniRef100_A7PD12 Cluster: Chromosome chr17 scaffold_12 = whole genome shotgun sequence; n = 1; *Vitis vinifera*\|Rep: Chromosome chr17 scaffold_12 = whole |

TABLE 2-continued of the Specification

| Locus/Display Name (1) | Source (2) | Start Base (3) | End Base (4) | ADDITIONAL LOCUS INFORMATION (5) |
|---|---|---|---|---|
| BF010272 | GMGI.071508 | 783671 | 784035 | genome shotgun sequence - *Vitis vinifera* (Grape) = partial (16%) UniRef100_Q00K67 Cluster: Major surface antigen; n = 1; Hepatitis B virus\|Rep: Major surface antigen - Hepatitis B virus (HBV) = partial (5%) |
| TA54422_3847 | *Glycine_max*_release_2 | 783644 | 784982 | Alcohol dehydrogenase superfamily = zinc-containing [*Medicago truncatula* (Barrel medic)] |
| BI971258 | *Glycine_max*_release_2 | 783921 | 784926 | Auxin-induced protein [*Vigna radiata*] |
| CV542673 | *Phaseolus_vulgaris*_release_2 | `` | 785346 | Quinone oxidoreductase-like protein [*Helianthus annuus* (Common sunflower)] |
| TC239445 | GMGI.071508 | 783904 | 786356 | similar to UniRef100_O23939 Cluster: Ripening-induced protein; n = 1; *Fragaria vesca*\|Rep: Ripening-induced protein - *Fragaria vesca* (Woodland strawberry) = partial (84%) |
| TA3037_3848 | *Glycine_soja*_release_2 | 784204 | 786191 | Quinone oxidoreductase-like protein [*Helianthus annuus* (Common sunflower)] |
| BG045149 | *Glycine_soja*_release_2 | 784943 | 785469 | Quinone oxidoreductase [*Fragaria ananassa* (Strawberry)] |
| TA54423_3847 | *Glycine_max*_release_2 | 784420 | 786354 | Quinone oxidoreductase-like protein [*Helianthus annuus* (Common sunflower)] |
| BG046280 | *Glycine_soja*_release_2 | 786163 | 786344 | NA |
| CA901808 | *Phaseolus_coccineus*_release_2 | 800890 | 801759 | Alcohol dehydrogenase superfamily, zinc-containing [*Medicago truncatula* (Barrel medic)] |
| TA14086_34305 | *Lotus_japonicus*_release_1 | 800932 | 801745 | Alcohol dehydrogenase superfamily, zinc-containing [*Medicago truncatula* (Barrel medic)] |
| TC23841 | LJGI.070108 | 800932 | 801745 | similar to UniRef100_Q43677 Cluster: Auxin-induced protein, n = 1, *Vigna radiata*\|Rep: Auxin-induced protein - *Vigna radiata*, partial (40%) |
| M0093116 | SEQ. Listing | 805373 | 805788 | SEQ ID NO: 13 |
| TC252650 | GMGI.071508 | 805357 | 806601 | similar to UniRef100_Q43677 Cluster: Auxin-induced protein; n = 1; *Vigna radiata*\|Rep: Auxin-induced protein - *Vigna radiata* = partial (54%) |
| BARC-039375-07304 | ePCR&blat | 805660 | 806532 | Map3.0 SNP L/Gm19 cM: 3.4 |
| TA65006_3847 | *Glycine_max*_release_2 | 805357 | 807089 | Quinone oxidoreductase-like protein [*Helianthus annuus* (Common sunflower)] |
| TA65005_3847 | *Glycine_max*_release_2 | 806611 | 807310 | Alcohol dehydrogenase superfamily = zinc-containing [*Medicago truncatula* (Barrel medic)] |

TABLE 2-continued of the Specification

| Locus/Display Name (1) | Source (2) | Start Base (3) | End Base (4) | ADDITIONAL LOCUS INFORMATION (5) |
|---|---|---|---|---|
| TC274718 | GMGI.071508 | 806611 | 807310 | similar to UniRef100_Q43677 Cluster: Auxin-induced protein; n = 1; *Vigna radiata*|Rep: Auxin-induced protein - *Vigna radiata* = partial (30%) |
| AW397551 | *Glycine_max*_release_2 | 811245 | 811796 | Auxin-induced protein [*Vigna radiata*] |
| Pvcon4580 | *Phaseolus_vulgaris* | 811330 | 813524 | UniRef100_Q43677 Auxin-induced protein n = 1 Tax = *Vigna radiata* RepID = Q43677_9FABA 1.00E-133 |
| asmbl_11877 | *Vigna_unguiculata* | 812523 | 812779 | NA |
| BE608172 | *Glycine_max*_release_2 | 821487 | 822389 | Protein farnesyltransferase subunit beta [*Pisum sativum* (Garden pea)] |
| BQ273477 | *Glycine_max*_release_2 | 821559 | 822383 | NA |
| TC246895 | GMGI.071508 | 821516 | 822443 | similar to UniRef100_Q04903 Cluster: Protein farnesyltransferase subunit beta; n = 1; *Pisum sativum*|Rep: Protein farnesyltransferase subunit beta - *Pisum sativum* (Garden pea) = partial (15%) |
| TC241767 | GMGI.071508 | 824186 | 828116 | similar to UniRef100_Q7XHJ0 Cluster: Formate dehydrogenase; n = 1; *Quercus robur*|Rep: Formate dehydrogenase - *Quercus robur* (English oak) = partial (97%) |
| TA40711_3847 | *Glycine_max*_release_2 | 824209 | 828372 | Formate dehydrogenase [*Quercus robur* (English oak)] |
| AI522957 | *Glycine_max*_release_2 | 826883 | 827087 | Formate dehydrogenase [*Quercus robur* (English oak)] |
| BG044450 | *Glycine_soja*_release_2 | 826544 | 827461 | Formate dehydrogenase = mitochondrial precursor [*Solanum tuberosum* (Potato)] |
| asmbl_11878 | *Vigna_unguiculata* | 826586 | 827463 | NA |
| CA800817 | *Glycine_soja*_release_2 | 826705 | 827869 | Formate dehydrogenase [*Quercus robur* (English oak)] |
| TC240429 | GMGI.071508 | 826957 | 828379 | similar to UniRef100_Q9ZRI8 Cluster: Formate dehydrogenase = mitochondrial precursor; n = 1; *Hordeum vulgare*|Rep: Formate dehydrogenase = mitochondrial precursor - *Hordeum vulgare* (Barley) = partial (40%) |
| AW350528 | *Glycine_max*_release_2 | 826986 | 828379 | Formate dehydrogenase 1 = mitochondrial precursor [*Oryza sativa* (Rice)] |
| BG882062 | *Glycine_max*_release_2 | 827372 | 828284 | Formate dehydrogenase 1 = mitochondrial precursor [*Oryza sativa* (Rice)] |
| BE347639 | *Glycine_max*_release_2 | 827443 | 828262 | Formate dehydrogenase 1 = mitochondrial precursor [*Oryza sativa* (Rice)] |
| CA782711 | *Glycine_soja*_release_2 | 827371 | 828357 | Formate dehydrogenase 1 = mitochondrial precursor [*Oryza sativa* (Rice)] |

TABLE 2-continued of the Specification

| Locus/Display Name (1) | Source (2) | Start Base (3) | End Base (4) | ADDITIONAL LOCUS INFORMATION (5) |
|---|---|---|---|---|
| TA40821_3847 | Glycine_max_release_2 | 829640 | 832253 | Formate dehydrogenase [Quercus robur (English oak)] |
| BE330555 | Glycine_max_release_2 | 829875 | 832057 | Formate dehydrogenase = mitochondrial precursor [Solanum tuberosum (Potato)] |
| BU090495 | Glycine_max_release_2 | 829863 | 832082 | Formate dehydrogenase [Quercus robur (English oak)] |
| BG044406 | Glycine_soja_release_2 | 829915 | 832082 | Formate dehydrogenase [Quercus robur (English oak)] |
| AW508186 | GMGI.071508 | 830914 | 831336 | similar to UniRef100_A7PMA5 Cluster: Chromosome chr14 scaffold_21 = whole genome shotgun sequence; n = 1; Vitis vinifera\|Rep: Chromosome chr14 scaffold_21 = whole genome shotgun sequence - Vitis vinifera (Grape) = partial (15%) |
| M0129925 | SEQ LISTING | 830552 | 831704 | SEQ ID NO: 14 |
| AW508186 | Glycine_max_release_2 | 830914 | 831970 | Formate dehydrogenase = mitochondrial precursor [Solatium tuberosum (Potato)] |
| AW508145 | Glycine_max_release_2 | 830909 | 832061 | Formate dehydrogenase [Quercus robur (English oak)] |
| TA40373_3847 | Glycine_max_release_2 | 830863 | 832118 | Formate dehydrogenase [Quercus robur (English oak)] |
| AW397259 | Glycine_max_release_2 | 831219 | 832141 | Formate dehydrogenase [Quercus robur (English oak)] |
| TC261330 | GMGI.071508 | 829795 | 833576 | similar to UniRef100_Q7XHJ0 Cluster: Formate dehydrogenase; n = 1; Quercus robur\|Rep: Formate dehydrogenase - Quercus robur (English oak) = partial (96%) |
| TC249502 | GMGI.071508 | 830866 | 832529 | similar to UniRef100_Q7XHJ0 Cluster: Formate dehydrogenase; n = 1; Quercus robur\|Rep: Formate dehydrogenase - Quercus robur (English oak) = partial (72%) |
| TA40376_3847 | Glycine_max_release_2 | 830879 | 833356 | Formate dehydrogenase [Quercus robur (English oak)] |
| asmbl_11879 | Vigna_unguiculata | 831735 | 833050 | NA |
| AW569072 | GMGI.071508 | 832471 | 832890 | similar to UniRef100_Q7XHJ0 Cluster: Formate dehydrogenase; n = 1; Quercus robur\|Rep: Formate dehydrogenase - Quercus robur (English oak) = partial (9%) |
| AW569072 | Glycine_max_release_2 | 832471 | 832929 | Formate dehydrogenase [Quercus robur (English oak)] |
| TA40339_3847 | Glycine_max_release_2 | 832130 | 833531 | Formate dehydrogenase 1 = mitochondrial precursor [Oryza sativa (Rice)] |
| TA5191_3885 | Phaseolus_vulgaris_release_2 | 832192 | 833517 | Formate dehydrogenase [Quercus robur (English oak)] |

TABLE 2-continued of the Specification

| Locus/Display Name (1) | Source (2) | Start Base (3) | End Base (4) | ADDITIONAL LOCUS INFORMATION (5) |
|---|---|---|---|---|
| FD790937 | Phaseolus_vulgaris | 833039 | 833412 | UniRef100_A6N0B2 Mitochondrial formate dehydrogenase 1 (Fragment) n = 1 Tax = Oryza sativa Indica Group RepID = A6N0B2_ORYSI 3.00E−30 |
| CA913454 | Phaseolus_coccineus_ release_2 | 841331 | 841722 | NA |
| TA70199_3847 | Glycine_max_release_2 | 841305 | 841824 | NA |
| asmbl_11880 | Vigna_unguiculata | 841326 | 841889 | NA |
| TA3611_3848 | Glycine_soja_ release_2 | 841347 | 842640 | Hypothetical protein OJ1593_C11.11 [Oryza sativa (japonica cultivar-group)] |
| TA5381_34305 | Lotus_japonicus_ release_1 | 841455 | 842700 | Calcium homeostasis regulator CHoR1 [Solanum tuberosum (Potato)] |
| TC20706 | LJGI.070108 | 841455 | 842700 | weakly similar to UniRef100_Q5QTN8 Cluster: Calcium homeostasis regulator CHoR1, n = 1, Solanum tuberosum\|Rep: Calcium homeostasis regulator CHoR1 - Solanum tuberosum (Potato), partial (52%) |
| Pvcon2378 | Phaseolus_vulgaris | 841347 | 843522 | UniRef100_A7PMA9 Chromosome chr14 scaffold_21, whole genome shotgun sequence n = 1 Tax = Vitis vinifera RepID = A7PMA9_VITVI 4.00E−94 |
| TC252755 | GMGI.071508 | 841305 | 843655 | similar to UniRef100_A7PMA9 Cluster: Chromosome chr14 scaffold_21 = whole genome shotgun sequence; n = 1; Vitis vinifera\|Rep: Chromosome chr14 scaffold_21 = whole genome shotgun sequence - Vitis vinifera (Grape) = partial (74%) |
| EX305183 | Phaseolus_vulgaris | 841682 | 843613 | UniRef100_A7PMA9 Chromosome chr14 scaffold_21, whole genome shotgun sequence n = 1 Tax = Vitis vinifera RepID = A7PMA9_VITVI 1.00E−67 |
| BI498351 | GMGI.071508 | 844582 | 845168 | NA |
| TA66563_3847 | Glycine_max_release_2 | 844582 | 847078 | Hypothetical protein [Ipomoea trifida (Morning glory)] |
| TC247953 | GMGI.071508 | 844582 | 847220 | similar to UniRef100_A7Q5T8 Cluster: Chromosome chr14 scaffold_54 = whole genome shotgun sequence; n = 1; Vitis vinifera\|Rep: Chromosome chr14 scaffold_54 = whole genome shotgun sequence - Vitis vinifera (Grape) = partial (58%) |
| TA3593_3848 | Glycine_soja_ release_2 | 844668 | 847194 | Hypothetical protein [Ipomoea trifida (Morning glory)] |
| TA56324_3847 | Glycine_max_release_2 | 854425 | 856413 | Similarity to intracellular protein [Arabidopsis thaliana (Mouse-ear cress)] |

TABLE 2-continued of the Specification

| Locus/Display Name (1) | Source (2) | Start Base (3) | End Base (4) | ADDITIONAL LOCUS INFORMATION (5) |
|---|---|---|---|---|
| TC235843 | GMGI.071508 | 854425 | 856413 | similar to UniRef100_A7PMB1 Cluster: Chromosome chr14 scaffold_21 = whole genome shotgun sequence; n = 1; *Vitis vinifera*|Rep: Chromosome chr14 scaffold_21 = whole genome shotgun sequence - *Vitis vinifera* (Grape) = partial (40%) |
| CD406351 | *Glycine_max_release_2* | 855627 | 856402 | Similarity to intracellular protein [*Arabidopsis thaliana* (Mouse-ear cress)] |
| TC276442 | GMGI.071508 | 855627 | 856402 | similar to UniRef100_A7PMB1 Cluster: Chromosome chr14 scaffold_21 = whole genome shotgun sequence; n = 1; *Vitis vinifera*|Rep: Chromosome chr14 scaffold_21 = whole genome shotgun sequence - *Vitis vinifera* (Grape) = partial (14%) |
| TC273993 | GMGI.071508 | 863632 | 864262 | homologue to UniRef100_A7PMB2 Cluster: Chromosome chr14 scaffold_21 = whole genome shotgun sequence; n = 1; *Vitis vinifera*|Rep: Chromosome chr14 scaffold_21 = whole genome shotgun sequence - *Vitis vinifera* (Grape) = partial (26%) |
| BU082700 | *Glycine_max_release_2* | 863841 | 864449 | Hypothetical protein OJ1126_B10.9 [*Oryza sativa* (*japonica* cultivar-group)] |
| AW459960 | *Glycine_max_release_2* | 863632 | 865288 | Hypothetical protein F4P13.4 [*Arabidopsis thaliana* (Mouse-ear cress)] |
| AL385435 | MTGI.071708 | 863952 | 865397 | homologue to UniRef100_A7PD25 Cluster: Chromosome chr17 scaffold_12, whole genome shotgun sequence, n = 1, *Vitis vinifera*|Rep: Chromosome chr17 scaffold_12, whole genome shotgun sequence - *Vitis vinifera* (Grape), partial (37%) |
| AI856244 | GMGI.071508 | 864500 | 864958 | UniRef100_A7PMB2 Cluster: Chromosome chr14 scaffold_21 = whole genome shotgun sequence; n = 1; *Vitis vinifera*|Rep: Chromosome chr14 scaffold_21 = whole genome shotgun sequence - *Vitis vinifera* (Grape) = partial (6%) |
| asmbl_11881 | *Vigna_unguiculata* | 863829 | 865710 | NA |
| TC238318 | GMGI.071508 | 863970 | 865869 | homologue to UniRef100_A7PMB2 Cluster: Chromosome chr14 scaffold_21 = whole genome shotgun sequence; n = 1; *Vitis vinifera*|Rep: Chromosome chr14 |

TABLE 2-continued of the Specification

| Locus/Display Name (1) | Source (2) | Start Base (3) | End Base (4) | ADDITIONAL LOCUS INFORMATION (5) |
|---|---|---|---|---|
| | | | | scaffold_21 = whole genome shotgun sequence - *Vitis vinifera* (Grape) = partial (34%) |
| TA63907_3847 | *Glycine_max*_release_2 | 864500 | 865869 | Hypothetical protein F4P13.4 [*Arabidopsis thaliana* (Mouse-ear cress)] |
| BW598574 | LJGI.070108 | 865265 | 865656 | similar to UniRef100_Q8LES3 Cluster: Protein kinase, n = 1, *Arabidopsis thaliana*\|Rep: Protein kinase - *Arabidopsis thaliana* (Mouse-ear cress), partial (9%) |
| BW598574 | *Lotus_japonicus*_release_1 | 865265 | 865674 | Protein kinase [*Arabidopsis thaliana* (Mouse-ear cress)] |
| CD400016 | *Glycine_max*_release_2 | 870972 | 871184 | NA |
| CD399245 | *Glycine_max*_release_2 | 870876 | 871427 | Putative Peptidyl-prolyl cis-trans isomerase = chloroplast [*Oryza sativa* (*japonica* cultivar-group)] |
| TC242592 | GMGI.071508 | 870943 | 872827 | similar to UniRef100_A6MZC4 Cluster: Peptidyl-prolyl cis-trans isomerase; n = 2; *Oryza sativa*\|Rep: Peptidyl-prolyl cis-trans isomerase - *Oryza sativa* subsp. *indica* (Rice) = partial (60%) |
| CB543642 | *Phaseolus_vulgaris*_release_2 | 871229 | 872777 | Peptidyl-prolyl cis-trans isomerase = chloroplast precursor [*Spinacia oleracea* (Spinach)] |
| TA52959_3847 | *Glycine_max*_release_2 | 870943 | 873450 | Poly(A) polymerase [*Pisum sativum* (Garden pea)] |
| CB539263 | *Phaseolus_vulgaris*_release_2 | 871195 | 873325 | Poly(A) polymerase [*Pisum sativum* (Garden pea)] |
| Pvcon1578 | *Phaseolus_vulgaris* | 870946 | 876143 | UniRef100_O22636 Poly(A) polymerase n = 1 Tax = *Pisum sativum* RepID = O22636_PEA E-0 |
| TA10487_34305 | *Lotus_japonicus*_release_1 | 873266 | 875963 | Poly(A) polymerase [*Pisum sativum* (Garden pea)] |
| TA6667_47247 | *Lotus_corniculatus*_release_1 | 873266 | 875963 | Poly(A) polymerase related cluster |
| TC34747 | LJGI.070108 | 873266 | 875963 | similar to UniRef100_O22636 Cluster: Poly(A) polymerase, n = 1, *Pisum sativum*\|Rep: Poly(A) polymerase - *Pisum sativum* (Garden pea), partial (57%) |
| BG363373 | *Glycine_max*_release_2 | 874357 | 874944 | Poly(A) polymerase [*Pisum sativum* (Garden pea)] |
| TC251420 | GMGI.071508 | 874369 | 876078 | similar to UniRef100_O22636 Cluster: Poly(A) polymerase; n = 1; *Pisum sativum*\|Rep: Poly(A) polymerase - *Pisum sativum* (Garden pea) = partial (37%) |
| CA901088 | *Phaseolus_coccineus*_release_2 | 874490 | 876191 | Poly(A) polymerase [*Pisum sativum* (Garden pea)] |
| asmbl_11882 | *Vigna_unguiculata* | 886629 | 890018 | NA |
| TA68870_3847 | *Glycine_max*_release_2 | 886534 | 893419 | Senescence-associated protein-like [*Oryza sativa* (*japonica* cultivar-group)] |
| TC270337 | GMGI.071508 | 886672 | 893419 | weakly similar to UniRef100_A7PD28 Cluster: Chromosome chr17 scaffold_12 = whole genome shotgun sequence; |

TABLE 2-continued of the Specification

| Locus/Display Name (1) | Source (2) | Start Base (3) | End Base (4) | ADDITIONAL LOCUS INFORMATION (5) |
|---|---|---|---|---|
| | | | | n = 1; *Vitis vinifera*|Rep: Chromosome chr17 scaffold_12 = whole genome shotgun sequence - *Vitis vinifera* (Grape) = partial (86%) |
| M0205537 | SEQ. Listing | 890458 | 890051 | SEQ ID NO: 15 |
| BM732054 | *Glycine_max*_release_2 | 899859 | 901015 | NA |
| BM732054 | GMGI.071508 | 900006 | 901015 | similar to UniRef100_Q04TD2 Cluster: MviN-related protein; n = 1; *Leptospira borgpetersenii* serovar Hardjo-bovis JB197|Rep: = partial (2%) |
| toGm13 | DAGchainer | 816170 | 1014875 | Ks0.1202 |
| M0202715 | SEQ. Listing | 921233 | 921630 | SEQ ID NO: 16 |
| TA46168_3847 | *Glycine_max*_release_2 | 921047 | 924660 | Homeodomain leucine zipper protein HDZ3 [*Phaseolus vulgaris* (Kidney bean) (French bean)] |
| TC260016 | GMGI.071508 | 921056 | 924739 | homologue to UniRef100_Q93XA3 Cluster: Homeodomain leucine zipper protein HDZ3; n = 1; *Phaseolus vulgaris*|Rep: Homeodomain leucine zipper protein HDZ3 - *Phaseolus vulgaris* (Kidney bean) (French bean) = complete |
| Pvcon1101 | *Phaseolus_vulgaris* | 921086 | 924758 | UniRef100_Q93XA3 Homeodomain leucine zipper protein HDZ3 (Fragment) n = 1 Tax = *Phaseolus vulgaris* RepID = Q93XA3_PHAVU 1.00E−124 |
| TA3604_3885 | *Phaseolus_vulgaris_* release_2 | 921111 | 924754 | Homeodomain leucine zipper protein HDZ3 [*Phaseolus vulgaris* (Kidney bean) (French bean)] |
| asmbl_11883 | *Vigna_unguiculata* | 921538 | 924758 | NA |
| BG041631 | *Glycine_soja_* release_2 | 923015 | 923340 | Homeobox-leucine zipper protein HAT5 [*Arabidopsis thaliana* (Mouse-ear cress)] |
| AV421688 | LJGI.070108 | 923118 | 924180 | similar to UniRef100_Q93XA3 Cluster: Homeodomain leucine zipper protein HDZ3, n = 1, *Phaseolus vulgaris*|Rep: Homeodomain leucine zipper protein HDZ3 - *Phaseolus vulgaris* (Kidney bean) (French bean), partial (25%) |
| TC235979 | GMGI.071508 | 923000 | 924768 | similar to UniRef100_Q93XA3 Cluster: Homeodomain leucine zipper protein HDZ3; n = 1; *Phaseolus vulgaris*|Rep: Homeodomain leucine zipper protein HDZ3 - *Phaseolus vulgaris* (Kidney bean) (French bean) = partial (86%) |

TABLE 2-continued of the Specification

| Locus/Display Name (1) | Source (2) | Start Base (3) | End Base (4) | ADDITIONAL LOCUS INFORMATION (5) |
|---|---|---|---|---|
| TA46165_3847 | Glycine_max_release_2 | 923000 | 924779 | Homeodomain leucine zipper protein HDZ3 [Phaseolus vulgaris (Kidney bean) (French bean)] |
| AW351287 | Glycine_max_release_2 | 923128 | 924720 | Homeodomain leucine zipper protein HDZ3 [Phaseolus vulgaris (Kidney bean) (French bean)] |
| CA785782 | Glycine_soja_release_2 | 925713 | 925880 | NA |
| Pvcon8364 | Phaseolus_vulgaris | 925735 | 926609 | UniRef100_A7PMB7 Chromosome chr14 scaffold_21, whole genome shotgun sequence n = 1 Tax = Vitis vinifera RepID = A7PMB7_VITVI 1.00E−27 |
| BE248998 | MTGI.071708 | 926978 | 927524 | similar to UniRef100_Q7F8S7 Cluster: PHD finger-like protein, n = 1, Oryza sativa Japonica Group|Rep: PHD finger-like protein - Oryza sativa subsp. japonica (Rice), partial (4%) |
| TC35470 | LJGI.070108 | 928423 | 929804 | similar to UniRef100_A7PMB8 Cluster: Chromosome chr14 scaffold_21, whole genome shotgun sequence, n = 1, Vitis vinifera|Rep: Chromosome chr14 scaffold_21, whole genome shotgun sequence - Vitis vinifera (Grape), partial (9%) |
| TA11035_34305 | Lotus_japonicus_release_1 | 928423 | 929825 | PHD finger-like protein [Oryza sativa (japonica cultivar-group)] |
| CA911004 | Phaseolus_coccineus_release_2 | 934882 | 939256 | T13O15.10 protein [Arabidopsis thaliana (Mouse-ear cress)] |
| AI856399 | GMGI.071508 | 937577 | 938041 | NA |
| AI856399 | Glycine_max_release_2 | 937577 | 938106 | NA |
| AW348703 | Glycine_max_release_2 | 963043 | 963750 | NA |
| TC276191 | GMGI.071508 | 963049 | 964044 | weakly similar to UniRef100_A7PZY3 Cluster: Chromosome chr8 scaffold_41 = whole genome shotgun sequence; n = 1; Vitis vinifera|Rep: Chromosome chr8 scaffold_41 = whole genome shotgun sequence - Vitis vinifera (Grape) = partial (21%) |
| BQ628183 | Glycine_max_release_2 | 963625 | 964044 | NA |
| BQ080193 | Glycine_max_release_2 | 963695 | 967475 | NA |
| TA52645_3847 | Glycine_max_release_2 | 963720 | 967461 | NA |
| TC256882 | GMGI.071508 | 963774 | 967475 | weakly similar to UniRef100_A7PZY3 Cluster: Chromosome chr8 scaffold_41 = whole genome shotgun sequence; n = 1; Vitis vinifera|Rep: Chromosome chr8 scaffold_41 = whole genome shotgun sequence - Vitis vinifera (Grape) = partial (45%) |
| BG156825 | Glycine_max_release_2 | 971121 | 971284 | NA |
| BG156825 | GMGI.071508 | 971125 | 971284 | NA |
| BU545761 | Glycine_max_release_2 | 971300 | 971901 | NA |

TABLE 2-continued of the Specification

| Locus/Display Name (1) | Source (2) | Start Base (3) | End Base (4) | ADDITIONAL LOCUS INFORMATION (5) |
|---|---|---|---|---|
| BU550718 | Glycine_max_release_2 | 971255 | 973578 | NA |
| TA72701_3847 | Glycine_max_release_2 | 972120 | 972806 | NA |
| TC271942 | GMGI.071508 | 972201 | 972806 | NA |
| TC269989 | GMGI.071508 | 971255 | 973827 | similar to UniRef100_A7P2M9 Cluster: Chromosome chr1 scaffold_5 = whole genome shotgun sequence; n = 1; Vitis vinifera\|Rep: Chromosome chr1 scaffold_5 = whole genome shotgun sequence - Vitis vinifera (Grape) = partial (63%) |
| BI317782 | Glycine_max_release_2 | 971510 | 973827 | NA |
| BI893512 | Glycine_max_release_2 | 971537 | 973848 | NA |
| BI893512 | GMGI.071508 | 971671 | 973848 | similar to UniRef100_A7P2M9 Cluster: Chromosome chr1 scaffold_5 = whole genome shotgun sequence; n = 1; Vitis vinifera\|Rep: Chromosome chr1 scaffold_5 = whole genome shotgun sequence - Vitis vinifera (Grape) = partial (54%) |
| CO985587 | Glycine_max_release_2 | 974859 | 976255 | Putative GTP-binding membrane protein LepA [Oryza sativa (japonica cultivar-group)] |
| AW596868 | Glycine_max_release_2 | 976346 | 976856 | NA |
| AW596868 | GMGI.071508 | 976412 | 976856 | similar to UniRef100_A2Q5T1 Cluster: Tetratricopeptide-like helical; n = 1; Medicago truncatula\|Rep: Tetratricopeptide-like helical - Medicago truncatula (Barrel medic) = partial (5%) |
| CA901672 | Phaseolus_coccineus_release_2 | 983905 | 984264 | Aldehyde dehydrogenase 1 precursor [Lotus corniculatus (Bird's-foot trefoil) |
| WmFPC_Contig4169 | | 899736 | 1068750 | NA |
| FE898889 | Phaseolus_vulgaris | 983908 | 984989 | UniRef100_A7PD33 Chromosome chr17 scaffold_12, whole genome shotgun sequence n = 1 Tax = Vitis vinifera RepID = A7PD33_VITVI 2.00E-79 |
| TC273361 | GMGI.071508 | 984396 | 986122 | similar to UniRef100_P93344 Cluster: Aldehyde dehydrogenase; n = 1; Nicotiana tabacum\|Rep: Aldehyde dehydrogenase - Nicotiana tabacum (Common tobacco) = partial (37%) |
| BE473475 | Glycine_max_release_2 | 984960 | 986122 | Aldehyde dehydrogenase [Nicotiana tabacum (Common tobacco)] |
| CV539672 | Phaseolus_vulgaris | 985959 | 987101 | UniRef100_P93344 Aldehyde dehydrogenase (NAD+) n = 1 Tax = Nicotiana tabacum RepID = P93344_TOBAC 7.00E-50 |
| AV410805 | LJGI.070108 | 987592 | 987888 | similar to UniRef100_A7PMC7 Cluster: Chromosome chr14 scaffold_21, whole |

TABLE 2-continued of the Specification

| Locus/Display Name (1) | Source (2) | Start Base (3) | End Base (4) | ADDITIONAL LOCUS INFORMATION (5) |
|---|---|---|---|---|
| | | | | genome shotgun sequence, n = 1, *Vitis vinifera*\|Rep: Chromosome chr14 scaffold_21, whole genome shotgun sequence - *Vitis vinifera* (Grape), partial (6%) |
| TC265505 | GMGI.071508 | 1011306 | 1012664 | similar to UniRef100_A7PMD1 Cluster: Chromosome chr14 scaffold_21 = whole genome shotgun sequence; n = 1; *Vitis vinifera*\|Rep: Chromosome chr14 scaffold_21 = whole genome shotgun sequence - *Vitis vinifera* (Grape) = partial (28%) |
| TA51641_3847 | *Glycine_max_*release_2 | 1011306 | 1013783 | Putative high-affinity potassium transporter protein 1 [*Nicotiana tabacum* (Common tobacco)] |
| CB540416 | *Phaseolus_vulgaris* | 1012333 | 1013531 | UniRef100_A7PMD1 Chromosome chr14 scaffold_21, whole genome shotgun sequence n = 1 Tax = *Vitis vinifera* RepID = A7PMD1_VITVI 5.00E-97 |
| BM891067 | GMGI.071508 | 1012675 | 1013617 | similar to UniRef100_A7PMD1 Cluster: Chromosome chr14 scaffold_21 = whole genome shotgun sequence; n = 1; *Vitis vinifera*\|Rep: Chromosome chr14 scaffold_21 = whole genome shotgun sequence - *Vitis vinifera* (Grape) = partial (22%) |
| TC131883 | MTGI.071708 | 1012665 | 1014070 | similar to UniRef100_A7PMD1 Cluster: Chromosome chr14 scaffold_21, whole genome shotgun sequence, n = 1, *Vitis vinifera*\|Rep: Chromosome chr14 scaffold_21, whole genome shotgun sequence - *Vitis vinifera* (Grape), partial (34%) |
| asmbl_11884 | *Vigna_unguiculata* | 1012674 | 1014123 | NA |
| BE330787 | *Glycine_max_*release_2 | 1013888 | 1014305 | Putative high-affinity potassium transporter protein [*Phytolacca esculenta* (Food pokeberry)] |
| FD792954 | *Phaseolus_vulgaris* | 1013779 | 1014573 | UniRef100_A7PMD1 Chromosome chr14 scaffold_21, whole genome shotgun sequence n = 1 Tax = *Vitis vinifera* RepID = A7PMD1_VITVI 3.00E-57 |
| TC244134 | GMGI.071508 | 1014004 | 1014793 | similar to UniRef100_A7PMD1 Cluster: Chromosome chr14 scaffold_21 = whole genome shotgun sequence; |

TABLE 2-continued of the Specification

| Locus/Display Name (1) | Source (2) | Start Base (3) | End Base (4) | ADDITIONAL LOCUS INFORMATION (5) |
|---|---|---|---|---|
| | | | | n = 1; *Vitis vinifera*|Rep: Chromosome chr14 scaffold_21 = whole genome shotgun sequence - *Vitis vinifera* (Grape) = partial (15%) |
| TA51642_3847 | *Glycine_max_release_2* | 1013926 | 1014875 | Putative high-affinity potassium transporter 1 [*Nicotiana rustica* (Aztec tobacco)] |
| TC242106 | GMGI.071508 | 1013926 | 1014875 | similar to UniRef100_A7PMD1 Cluster: Chromosome chr14 scaffold_21 = whole genome shotgun sequence; n = 1; *Vitis vinifera*|Rep: Chromosome chr14 scaffold_21 = whole genome shotgun sequence - *Vitis vinifera* (Grape) = partial (15%) |
| BI970123 | *Glycine_max_release_2* | 1014128 | 1014721 | Putative potassium transporter HAK1p [*Mesembryanthemum crystallinum* (Common ice plant)] |
| BQ080303 | *Glycine_max_release_2* | 1018604 | 1019142 | NA |
| TC270109 | GMGI.071508 | 1018604 | 1019142 | weakly similar to UniRef100_UPI0000196D39 Cluster: NHL repeat-containing protein; n = 1; *Arabidopsis thaliana*|Rep: NHL repeat-containing protein - *Arabidopsis thaliana* = partial (4%) |
| BQ080219 | *Glycine_max_release_2* | 1018604 | 1019579 | NA |
| TA62145_3847 | *Glycine_max_release_2* | 1021347 | 1023221 | NA |
| TC245123 | GMGI.071508 | 1021347 | 1023221 | similar to UniRef100_A7PMD2 Cluster: Chromosome chr14 scaffold_21 = whole genome shotgun sequence; n = 1; *Vitis vinifera*|Rep: Chromosome chr14 scaffold_21 = whole genome shotgun sequence - *Vitis vinifera* (Grape) = partial (31%) |
| asmbl_11885 | *Vigna_unguiculata* | 1022417 | 1022510 | NA |
| CA784724 | *Glycine_max_release_2* | 1046117 | 1047384 | NA |
| CA784724 | GMGI.071508 | 1046400 | 1047384 | similar to UniRef100_A7Q2E7 Cluster: Chromosome chr1 scaffold_46 = whole genome shotgun sequence; n = 1; *Vitis vinifera*|Rep: Chromosome chr1 scaffold_46 = whole genome shotgun sequence - *Vitis vinifera* (Grape) = partial (17%) |
| Pvcon4015 | *Phaseolus_vulgaris* | 1047011 | 1048610 | UniRef100_A5ATC1 Putative uncharacterized protein n = 1 Tax = *Vitis vinifera* RepID = A5ATC1_VITVI 1.00E-146 |
| BQ742289 | *Glycine_max_release_2* | 1048650 | 1048767 | NA |
| BF068315 | GMGI.071508 | 1057203 | 1057316 | similar to UniRef100_Q8MIG1 Cluster: Skinkine; n = 1; *Sus scrofa*|Rep: Skinkine - *Sus scrofa* (Pig) = partial (12%) |

TABLE 2-continued of the Specification

| Locus/Display Name (1) | Source (2) | Start Base (3) | End Base (4) | ADDITIONAL LOCUS INFORMATION (5) |
|---|---|---|---|---|
| BF068315 | Glycine_max_release_2 | 1057203 | 1057506 | NA |
| BU083500 | GMGI.071508 | 1058026 | 1058431 | UniRef100_Q2R023 Cluster: Expressed protein; n = 1; *Oryza sativa Japonica* Group\|Rep: Expressed protein - *Oryza sativa* = partial (2%) |
| TA74227_3847 | Glycine_max_release_2 | 1058026 | 1059408 | NA |
| BI423963 | GMGI.071508 | 1058432 | 1059275 | similar to UniRef100_Q2QDD6 Cluster: Nodulin-like protein; n = 1; *Gossypium hirsutum*\|Rep: Nodulin-like protein - *Gossypium hirsutum* (Upland cotton) (*Gossypium mexicanum*) = partial (22%) |
| TC237120 | GMGI.071508 | 1063015 | 1063972 | UniRef100_Q39819 Cluster: Hsp22.3; n = 1; *Glycine max*\|Rep: Hsp22.3 - *Glycine max* (Soybean) = complete |
| CA802234 | Glycine_soja_release_2 | 1061477 | 1067499 | Similarity to nodulin [*Arabidopsis thaliana* (Mouse-ear cress)] |
| BI425574 | GMGI.071508 | 1065519 | 1066854 | weakly similar to UniRef100_A7PMD8 Cluster: Chromosome chr14 scaffold_21 = whole genome shotgun sequence; n = 1; *Vitis vinifera*\|Rep: Chromosome chr14 scaffold_21 = whole genome shotgun sequence - *Vitis vinifera* (Grape) = partial (21%) |
| BI425574 | Glycine_max_release_2 | 1065519 | 1066940 | Hypothetical protein [*Medicago truncatula* (Barrel medic)] |
| AU251786 | LJGI.070108 | 1066790 | 1067424 | weakly similar to UniRef100_A7Q2G7 Cluster: Chromosome chr1 scaffold_46, whole genome shotgun sequence, n = 1, *Vitis vinifera*\|Rep: Chromosome chr1 scaffold_46, whole genome shotgun sequence - *Vitis vinifera* (Grape), partial (7%) |
| Pvcon8451 | *Phaseolus_vulgaris* | 1065511 | 1068752 | UniRef100_A7PMD8 Chromosome chr14 scaffold_21, whole genome shotgun sequence n = 1 Tax = *Vitis vinifera* RepID = A7PMD8_VITVI 7.00E−91 |
| TC260900 | GMGI.071508 | 1065796 | 1069134 | weakly similar to UniRef100_A7PMD8 Cluster: Chromosome chr14 scaffold_21 = whole genome shotgun sequence; n = 1; *Vitis vinifera*\|Rep: Chromosome chr14 scaffold_21 = whole genome shotgun sequence - *Vitis vinifera* (Grape) = partial (41%) |
| TA63020_3847 | Glycine_max_release_2 | 1067436 | 1069134 | NA |
| CA783703 | Glycine_soja_release_2 | 1068257 | 1068879 | NA |
| TA58065_3847 | Glycine_max_release_2 | 1074998 | 1076541 | AT3g28050/MMG15_6 [*Arabidopsis thaliana* (Mouse-ear cress)] |

TABLE 2-continued of the Specification

| Locus/Display Name (1) | Source (2) | Start Base (3) | End Base (4) | ADDITIONAL LOCUS INFORMATION (5) |
|---|---|---|---|---|
| TC251785 | GMGI.071508 | 1074998 | 1076541 | similar to UniRef100_Q8L9I2 Cluster: Nodulin MtN21-like protein; n = 1; *Arabidopsis thaliana*|Rep: Nodulin MtN21-like protein - *Arabidopsis thaliana* (Mouse-ear cress) = partial (16%) |
| CB280623 | *Phaseolus_vulgaris_release_2* | 1075036 | 1076540 | AT3g28050/MMG15_6 [*Arabidopsis thaliana* (Mouse-ear cress)] |
| EH043320 | *Arachis_stenosperma_release_5* | 1075056 | 1077422 | Cluster: Hypothetical protein, n = 1, *Medicago truncatula*|Rep: Hypothetical protein - *Medicago truncatula* (Barrel medic) |
| asmbl_11886 | *Vigna_unguiculata* | 1075036 | 1077585 | NA |
| BQ094260 | *Glycine_max_release_2* | 1075548 | 1077551 | Nodulin-like protein [*Arabidopsis thaliana* (Mouse-ear cress)] |
| BF598290 | *Glycine_soja_release_2* | 1075557 | 1077593 | Nodulin-like protein [*Arabidopsis thaliana* (Mouse-ear cress)] |
| Pvcon6314 | *Phaseolus_vulgaris* | 1075036 | 1078733 | UniRef100_A7PMD8 Chromosome chr14 scaffold_21, whole genome shotgun sequence n = 1 Tax = *Vitis vinifera* RepID = A7PMD8_VITVI 1.00E−105 |
| TA58064_3847 | *Glycine_max_release_2* | 1075337 | 1079189 | AT3g28050/MMG15_6 [*Arabidopsis thaliana* (Mouse-ear cress)] |
| TC255833 | GMGI.071508 | 1075337 | 1079189 | weakly similar to UniRef100_A7PMD8 Cluster: Chromosome chr14 scaffold_21 = whole genome shotgun sequence; n = 1; *Vitis vinifera*|Rep: Chromosome chr14 scaffold_21 = whole genome shotgun sequence - *Vitis vinifera* (Grape) = partial (64%) |
| BG042956 | *Glycine_soja_release_2* | 1078885 | 1079014 | NA |
| TC263589 | GMGI.071508 | 1086875 | 1091139 | similar to UniRef100_A7PME0 Cluster: Chromosome chr14 scaffold_21 = whole genome shotgun sequence; n = 1; *Vitis vinifera*|Rep: Chromosome chr14 scaffold_21 = whole genome shotgun sequence - *Vitis vinifera* (Grape) = partial (35%) |
| TA50577_3847 | *Glycine_max_release_2* | 1086875 | 1094082 | Alpha-dioxygenase [*Pisum sativum* (Garden pea)] |
| asmbl_11887 | *Vigna_unguiculata* | 1089135 | 1092345 | NA |
| CA410123 | *Lupinus_albus_release_2* | 1092182 | 1092694 | Alpha-dioxygenase [*Pisum sativum* (Garden pea) |
| Pvcon4974 | *Phaseolus_vulgaris* | 1091225 | 1093836 | UniRef100_Q5GQ66 Alpha-dioxygenase n = 1 Tax = *Pisum sativum* RepID = Q5GQ66_PEA E−0 |

TABLE 2-continued of the Specification

| Locus/Display Name (1) | Source (2) | Start Base (3) | End Base (4) | ADDITIONAL LOCUS INFORMATION (5) |
|---|---|---|---|---|
| TC243973 | GMGI.071508 | 1091177 | 1094141 | similar to UniRef100_Q5GQ66 Cluster: Alpha-dioxygenase; n = 1; *Pisum sativum*\|Rep: Alpha-dioxygenase - *Pisum sativum* (Garden pea) = partial (61%) |
| asmbl_11888 | *Vigna_unguiculata* | 1092518 | 1093829 | NA |
| M0206286 | SEQ. Listing | 1209562 | 1210392 | SEQ ID NO: 17 |
| M0206054 | SEQ. Listing | 1465522 | 1465187 | SEQ ID NO: 18 |
| M0205375 | SEQ. Listing | 2010060 | 2009541 | SEQ ID NO: 19 |
| toGm13 | DAGchainer | 1046081 | 4647877 | Ks0.2059 |
| NA | Glyma1 | 1 | 50600000 | NA |

Sequences for the genes provided above can be obtained from the World Wide Web (or Internet) using the identifiers provided in Column 1 (Locus/Display Name) or Column 5 (ADDITIONAL LOCUS INFORMATION) from the following internet locations: "soybase.org" (described in Grant et al., Nucleic Acids Research, 2010, Vol. 38, Database issue D843-D846) or soybase.org/gbrowse/cgi-bin/gbrowse/gmax1.01/(see Hyten D L, Choi I-Y, Song Q, Specht J E, Carter T E et al. (2010) A high density integrated genetic linkage map of soybean and the development of a 1,536 Universal Soy Linkage Panel for QTL mapping. Crop Science 50:960-968. (Crop Science); and Hyten D L, Cannon S B, Song Q, Weeks N, Fickus E W et al. (2010) High-throughput SNP discovery through deep resequencing of a reduced representation library to anchor and orient scaffolds in the soybean whole genome sequence. BMC Genomics 11(1): 38);

"phytozome.net" or "phytozome.net/cgi-bin/gbrowse/soybean/?name=Gm09";

"www.plantgdb.org" or "plantgdb.org/GmGDB/ (Assembly version Glyma1.170 (April 2009)"; and, "ncbi.nlm.nih.gov/sites/entrez" and subsites "ncbi.nlm.nih.gov/nucest", "ncbi.nlm.nih.gov/dbEST", "ncbi.nlm.nih.gov/genbank/", ".ncbi.nlm.nih.gov/sites/genome", "ncbi.nlm.nih.gov/unigene", and "ncbi.nlm.nih.gov/UniGene/UGOrg.cgi?TAXID=3847".

We claim:

1. A method of identifying a soybean plant that comprises a genotype associated with dicamba tolerance, the method comprising:
   (a) detecting in a soybean plant an allele in each of at least two linkage group L genomic regions associated with dicamba tolerance, wherein the at least two genomic regions are selected from:
      (i) a first linkage group L genomic region flanked by loci M0205928 (SEQ ID NO: 4) and M0129138 (SEQ ID NO: 6), wherein the region comprises the locus of M0101742 (SEQ ID NO: 5);
      (ii) a second linkage group L genomic region that is flanked by loci BU551363 (SEQ ID NO: 9) and BU765955 (SEQ ID NO: 12), wherein the region comprises the loci M0205350 (SEQ ID NO:10) and M0102027 (SEQ ID NO: 11); and
      (iii) a third linkage group L genomic region that is flanked by loci BU551345 (SEQ ID NO:7) and M0114388 (SEQ ID NO:8), wherein the region comprises the locus NGMAX008197032 (SEQ ID NO: 52);
   (b) denoting that said plant comprises a genotype associated with dicamba tolerance; and
   (c) crossing the soybean plant denoted in step (b) to another soybean plant.

2. The method of claim 1, wherein said method further comprises the step of selecting said denoted plant from a population of plants.

3. The method of claim 1, wherein said plant comprises a transgene that confers resistance to dicamba and/or a transgene that confers resistance to glyphosate.

4. The method of claim 3, wherein said soybean plant or progeny thereof is exposed to a dosage of dicamba sufficient to cause a deleterious effect in a susceptible variety comprising the transgene and/or is exposed to a dosage of glyphosate sufficient to cause sterility in a susceptible variety comprising the transgene(s).

5. The method of claim 2, wherein a plant that exhibits dicamba tolerance and/or reproductive tolerance to glyphosate is selected.

6. The method of claim 1, wherein said genotype associated with dicamba tolerance comprises at least one allele associated with dicamba tolerance in each of said at least two linkage group L regions, said alleles selected from the group consisting of a TT allele M0205350 (SEQ ID NO: 10), a TT allele of M0101742 (SEQ ID NO: 5), a CC allele of M0102027 (SEQ ID NO: 11), and an AA allele of NGMAX008197032 (SEQ ID NO:52).

7. A method for obtaining a soybean plant comprising in its genome at least one dicamba tolerance locus, the method comprising the steps of:
   (a) genotyping a plurality of soybean plants with respect to at least one polymorphic genetic locus in each of at least two linkage group L genomic regions selected from:
      (i) a first linkage group L genomic region flanked by loci M0205928 (SEQ ID NO: 4) and M0129138 (SEQ ID NO: 6), wherein the region comprises the locus of M0101742 (SEQ ID NO: 5);
      (ii) a second linkage group L genomic region that is flanked by loci BU551363 (SEQ ID NO: 9) and BU765955 (SEQ ID NO: 12), wherein the region comprises the loci M0205350 (SEQ ID NO:10) and M0102027 (SEQ ID NO: 11); and
      (iii) a third linkage group L genomic region that is flanked by loci BU551345 (SEQ ID NO:7) and M0114388

(SEQ ID NO:8), wherein the region comprises the locus NGMAX008197032 (SEQ ID NO: 52); and
(b) selecting a soybean plant comprising in its genome at least one genetic locus comprising a genotype associated with dicamba tolerance; and
(c) crossing the soybean plant selected in step (b) to another soybean plant.

8. The method of claim 7, wherein said genotype associated with dicamba tolerance comprises at least one allele associated with dicamba tolerance in each of said at least two linkage group L regions, said alleles selected from the group consisting of a TT allele M0205350 (SEQ ID NO: 10), a TT allele of M0101742 (SEQ ID NO: 5), a CC allele of M0102027 (SEQ ID NO: 11), and an AA allele of NGMAX008197032 (SEQ ID NO:52).

9. The method of claim 7, wherein said plurality of soybean plants comprises a population that is obtained by: i) crossing a parent plant comprising at least one dicamba tolerance locus with a parent plant comprising at least one dicamba sensitivity locus; or, ii) obtaining seed or progeny from a parental plant segregating for at least one dicamba tolerance locus.

10. The method of claim 7, wherein said population contains plants that comprise a transgene that confers resistance to dicamba.

11. The method of claim 7, further comprising the step of assaying for the presence of at least one additional marker, wherein said additional marker is either linked or unlinked to said linkage group L genomic region.

12. The method of claim 7, wherein said plurality of soybean plants, said soybean plant, and/or progeny thereof are exposed to a dosage of dicamba sufficient to cause a deleterious effect in a susceptible variety comprising a dicamba resistance transgene and/or is exposed to a dosage of glyphosate sufficient to cause sterility in a susceptible variety comprising a glyphosate tolerant transgene.

13. The method of claim 7, wherein a plant that exhibits dicamba tolerance is selected.

* * * * *

```
                         SEQUENCE LISTING

<160> NUMBER OF SEQ ID NOS: 56

<210> SEQ ID NO 1
<211> LENGTH: 563
<212> TYPE: DNA
<213> ORGANISM: Glycine max

<400> SEQUENCE: 1
cctcgtgccg aatttcggca cgaggagtgg ttgaggcaag ggatgagctg cacagaatgt      60
tgaatgagga tgaacttaga gatgctgttt tgcttgtttt tgccaacaag caagatcttc     120
ctaatgcaat gaatgctgca gaaataactg acaagcttgg acttcattca ctccgtcaac     180
gccactggta tatccagagc acttgtgcaa cttctggaga gggtctctat gagggtttgg     240
actggctttc taacaacatt gccagcaaag catgagacat ttgaaaaatt ttggtcttgt     300
ctggtgattt catgcgagtc tggcggttct tggagaaaga tgcttatctt ttctagcgaa     360
tgttgcaata gcagaatgct tgctagaagt attctctttt gtgtaacttg ggtttgtatg     420
attgcttaaa ttagctaata cttttagcta taattggaac tcttgcaccc tcttgtgcgt     480
gcgtgctgtg ttgcttacat cttgtttgtt tgattttttga ttgaatatat ttccatgcgt     540
tttgttcttg aaaaaaaaaa aaa                                            563

<210> SEQ ID NO 2
<211> LENGTH: 1098
<212> TYPE: DNA
<213> ORGANISM: Glycine max

<400> SEQUENCE: 2
```

```
atggcaagca tttctagcat tccatcacac ataaaaactt gggtttattc tgaatatggg    60
aacacagaag agattctaaa atttgatccc aacgtaccta taccagacat caaggaagac   120
caggtgctca tcaaggttgt ggctacagct cttaatcctg tggattataa gagggctctt   180
ggctatttca agaacactga ctctccctta cctgtaagat catgatttta aatttatatt   240
tgcgtggatt attaattagt atagtttcca ttttgtatac caccttatat aattcttttt   300
tgtttaaata tatttttagt ttttataatt tatatttttt tgtttttgt tattgtaaaa    360 ttatttttt gttttgtttt ttataaatta tgtttgtttt attttctttt cctaaattat    420
tttagataat gttttgaata gtaaaaaaat attataacaa taaaaaataa aataaacata   480
atttgtaaga atcaaaaata aaaataatt tgtaagtaaa aaaataaaaa ataaataaat    540
tataaggatt aaaattgtat ttaagccatt tttttttatc attgcattgt ttaatttgtg   600
tttggttttt gaaattaaga gtgttccggg gtacgatgtt gctggtgtgg tggtaagagt   660
gggaagtaaa gtgaggaaat tcaaggttgg ggatgaggtt tatggtgata tcaatgagta   720
tgctgtgaat aatccaaaga ccattgggac tttggcagag tacactgcta ctgaagagaa   780
attgttggct cacaaaccct ccaatttgag ctttattgaa gctgctagcc ttcctttagc   840
tatcatcact gcttatcaag gacttgaaag agttgatttt tctgctggaa aatctatact   900
tgttctagga ggtgctggtg gagttggatc ccttgttatt caggtttgat atcttccatc   960
tccattggtt aatttgacaa taagtttcaa ttaaacagtg tcttactgaa atattgagcc  1020
attaatttca cttttcagt attttagtta tttatttat tcttcttctc taatcatatg    1080
atttaggagc aatgatat                                                1098
```

```
<210> SEQ ID NO 3
<211> LENGTH: 635
<212> TYPE: DNA
<213> ORGANISM: Glycine max
<220> FEATURE:
<221> NAME/KEY: unsure
<222> LOCATION: (1)..(635)
<223> OTHER INFORMATION: unsure at all n locations

<400> SEQUENCE: 3
```

```
ttggcacnaa aaatggggtg agaagtatct gtctctaatg tttcaggttt ntnnncgagg    60
atcctaatta tttggacgaa agacaaaacc gcagaaaggg gtttctttgg acaaaaattt   120
atcgatattt agctgacata tttttacta agtctagaat cctaaagtaa tcaaagaaga    180
gagaagattc ttttccctcc agtccatccc gggtgaccct gttgctacca gccagattat   240
tacatggact gccaccaaca attagatcaa aaccaccaaa tgtgctcatc agctgctcca   300
agcgatcacc gtctagctcc cttacatcgt caatnnnata tagattaccct ttctgatttg    360 tttgctccca ccaacttcta acaatattcc tattcacttc tgattttca acagacacaa    420 cattcttgag agggatgccg agccgatgaa gagctacctc tgccccacca attccagaaa   480
agagagaaag aagattgata ccattaggat acatctnntt cagaactgac aagtggtatg   540
ccacannntc aacctggaat gaattaccaa gtgacttnnn tctgtcagtn ntacttattc   600
cacctcctct gnnntggttc cttgggaagc ccagc                             635
```

```
<210> SEQ ID NO 4
<211> LENGTH: 385
<212> TYPE: DNA
<213> ORGANISM: Glycine max
```

```
<400> SEQUENCE: 4
attcctattt cctacacaac actacactgt ctggtggaag aatctcttca ctctccatgc    60
aacaacgttg gctatgtctc cttattctct ctctttgtta gcctctgtct cccccaaaat   120 gcacacccctt ctttctttct cctcatcaca ctctccacat cttccaaacc acaacataac   180
caaatccaat aataaactct ctcattccat caatggactt tcatcmtgcc cttcttctcc   240
tttgctcccc agtgccacaa aatcttctcc ctttctcatt tccacttcaa aaattgcatc   300
tttcagggtc cttgctgctt cctctatacc tgatgctaga agtgatgaac cagccaaaac   360
tagtgatttc ttaaaaactc ttcag                                         385

<210> SEQ ID NO 5
<211> LENGTH: 1304
<212> TYPE: DNA
<213> ORGANISM: Glycine max

<400> SEQUENCE: 5
acacagaaat cacaaacaag tggtgactac ttacccatat tcaccaaaga aatggaaaaa    60
cttctagaac ttgtgacaaa acaaaactgg gggactcact ctgagggcat gtcatcaaca   120
acaaccactc ctatctatgg cttggcacaa tgcttccaag acctttccag cattgattgc   180
cttcaatgct ttgcagccag ccgcaccaag ctccctcgct gcctcccttc ggtttcggct   240
cgaatttacc ttgatggctg cttccttcgc tatgacaatt acagtttcta cactgaaaac   300 tatgacccctt tgagggacac agtgaattgc acctcagagt atggttctgt ggttggtgat   360
ggtgagaagt tggtgtttgc tgagagtgtt ggcaaagtgg ttgagagtgt ggtgagggtg   420
gctgtgaata taatgagggg aagaggcttt tttgcagttg agaaggtgg gggagtttat    480 gcattggcac agtgctggaa aactgttggg gtaaaagggt gtagtgattg cttgaggaaa   540
gctgaaaatg aggtcaaagg atgtttgcct aagagggaag ggagggcctt gaatactggg   600
tgctatttga gatactcaac tgttaagttc tacaatcaag gaggtcaaga tggtcaagga   660
gatggtaaga gctgttgctc tagtttgaag ttttatatt cttcattagt ttccttggttc   720 cttttggata aacttctcaa ccactagtta taggagaaaa aaatgaatta acatctctt    780 gtaagttaaa atcaatttgt gcacttcgat aagttttata aaaactctct cgtttaactt   840
ttccaaaagc tgagatgtat aagttaattt taacttacag aagaagtttg attcattttt   900 gcttttatg ttcttctcct ttaagtattt attgagaagc ttatcggttg gaatttggaa    960
actgaagctc aactgggaat ttcaattgca tattgttacc atgcagtttc aaattccttg   1020
tgttgcttat aggttaaatg acaaatggag aaggaaagaa gtaaagatga atgttactgt   1080
atcattgtga atgaaatgct gcttttcaac tttaactttg ctataactct aggttagtt    1140 ttggtgtcta aagtttgtcc tgaatagaat cctaggtttc agttcataga tggcatagat   1200
acatgytagt catttatttt gtatacatgt tgatgcaatt gtccatgttt taattttttca   1260 gattcttcca gaaaacgagt cattatagca gcagggtcag tctt                   1304

<210> SEQ ID NO 6
<211> LENGTH: 1057
<212> TYPE: DNA
<213> ORGANISM: Glycine max

<400> SEQUENCE: 6
cgccagcttg catgcctgca gttccaagaa ttatttcaaa ccgctgcttc cattttagaa    60
tccttgttat gtccttttct gcacagtaga ttagtatgtc acaagttgca tgttgggccg   120
```

```
gttgatttta tgaaattaat aagagttaaa tatgttttta gtccttgcaa ataggaaaaa      180
gttctccttt tggtcctcaa ttatgaaaat gtgtcctrta tgatcttatt tacataaatg      240
aggaaatgaa agcagatgat acttttatga aggacaaaga ttacatttga cacattttca      300
taaatgagtg actaaaaaga agcattttat tttttagtga ttaaattaat tggaaacatt      360
acaagattac ttttggtcat gggttcaaga atccggaaac agtttctttg catatgcaag      420
ggtaatgctg cttacaatat ccctccccca taccttggca tagtgaggag cctccgggca      480
atggaataca ctagttttta tagtacaata ttttcattt agagttactg tgggacaaaa       540
ggaacttacc aaaaatgaat tgatctaagc tcttgttagg taggtactca tacacaatga      600
ggctctcagg gccttcaatg ctgcaaccca atagtttgac aaggttcttg tgttgcattc      660
cactaatcaa attcacttca ttgaagaaat catccaccca ttgcctatta ttgaagacca      720
atctcttaac agcaacatca ttcccatttg gcagagtccc tttgtataca gaaccagatc      780
ctccttgacc tatcttctt gaagagctga ataatccgt cgccttctct agagtttcat        840
atttgtaatt caagctagaa ttcttcaagg aaggaggaac ctcaataaaa ttgttttctg      900
agtgattcag gagaaaatga aatacagcat cagcaaaatt aacaaacaat cattccaaat     960
atatattatt ggtatgaaca agagtgttct ccagaacatt acttcttctc tttttggtga     1020
aggccacata agagactgca agagtgagaa ctacaac                              1057

<210> SEQ ID NO 7
<211> LENGTH: 384
<212> TYPE: DNA
<213> ORGANISM: Glycine max
<220> FEATURE:
<221> NAME/KEY: unsure
<222> LOCATION: (1)..(384)
<223> OTHER INFORMATION: unsure at all n locations

<400> SEQUENCE: 7
tttagtcatt agaattttac ttgtttactc ggttcgaaag ttccatctcg ctggtctcaa       60
ttactattaa aaaatctcat attgcttacc tcaattagtg ggatgaggtt taagtacgtg      120
atgaacaact tcacttnntg ctaattagtt tgaagttata atgtaacatg ctctatcctt      180 cttttttggtt ggttgcttgg ggggagctcc cnnnnacatg gaattattgg gaatcaagct    240
tccataattg tttcttcact tcttgatggc ctaattaagc tgcatgtgct agagaactca      300
gaggggctgt aggacacacc aatcttctta aatgtgtttg atgaggagct gtctatgcta      360
aaacctaatg gagatgttg atct                                              384

<210> SEQ ID NO 8
<211> LENGTH: 823
<212> TYPE: DNA
<213> ORGANISM: Glycine max

<400> SEQUENCE: 8
aattacacac atcatgatct tgtaatcatc atctcccaaa tcagggatag ccttggcctt       60
cttaccccag ggattccata ccactgcact ctcattatca ccaaaccaat aagtgacatc      120
aattgtagat taaattaaca aacttatgta atctgaatg ctggatctgg cccttataaa       180
gtgaaaaaca cgttgtagag actaaagtaa gtaatcccct tgttttttgat gaggaaatga    240 acagttgata ttatgtgcac ttgtataaca aaacatggaa attttaaaat atcagtcgtt      300 gatttttctca tcaataaatt aggattgttt tactctctaa agtgacttgt tcagattaga    360
```

```
agagccaaat agatacaatg ccatgcaaaa ttttttattct ctgactaata actaataaca    420
acctgcatct ggcattcctt tcttctggag tacaaaagtt ctttttttct catggtctat    480
gatggcaatt ttagttgggc trtgcaagta cactctgtcc atctacaagg taaccacaaa    540
tgtccttaga gaacacttga aaaaaaagtt gatttggtat ctattatata tattcataca    600
ctcgaaaatc aatcagaata tatataggtt atgtgcactt atgtgcttat gatgtcaatt    660
ttcttagcct gtgagacacc tccaaccaat tgaatgaaag gaccagaaaa tcaaattata    720
cctctccatc aaaagtgagt gcatctgcct gctctgtgaa ccttgatctg ttcaacagat    780
tgtcaaagta atccagtgtc tccaatccct caatacgcac ttc                      823

<210> SEQ ID NO 9
<211> LENGTH: 596
<212> TYPE: DNA
<213> ORGANISM: Glycine max
<220> FEATURE:
<221> NAME/KEY: unsure
<222> LOCATION: (1)..(596)
<223> OTHER INFORMATION: unsure at all n locations

<400> SEQUENCE: 9
taaccaactt acgcacaaga tgtatgaaat tggccagaca agcgatgcaa attacaaagg     60
tatcctgtag gtctcatata tgctgctaaa agcaccccca aagcttagac ataaactata    120
taacaccgcc catatgatcc aaatcccaac cataaacata cgaaaccaaa atataccaca    180
aaccaaactc tcagatccac cctcatcaaa agccaacaaa acaacttcc aagttcgatc    240 ccctctcaac aaaaggaac aaacttacat taaaaaacta aattccttct ataattaaaa    300
tcttggctgt ttattctgtc tgtaaccaaa acaaaactgt cattgcgctt tgagtatgcc    360
aactcccacc agctttaaac ccgtgtgcta gctcaccata tgaaaatggt gggcagattg    420
aataatctat aactcgtctt aagtgaatga aaattttatt ttgttgagaa ctattttca    480 aaccctcaaa cagattactt tatttgcaag gttttcaagt caatttcatt tagannnnna    540
ggaaaaggtt caataggtag tatcacaaat ccttcttttt gagtaaattt tgatgc        596

<210> SEQ ID NO 10
<211> LENGTH: 321
<212> TYPE: DNA
<213> ORGANISM: Glycine max

<400> SEQUENCE: 10
gggcttctcc gctcgaactt atgcaagggc tatgtgatgg tgatgatgat tgaatttgaa     60
gctgctactg cattactctc tttggtaatg aatttgaaga agcagaaaga aaggaaatga    120
tggtctttac accgtcaatt ttaatatwtg taagtgtaaa ctctgtagta gcacagtgat    180
gtagtgtaga ttaggcattt ggcagcgtgg taaatattct tagattgaat tgtgttatca    240
acagtattaa acgttttagg ctgaatgaat gatattgatg aatttataag gtggggaggc    300
taagatggaa tcatgtagtt a                                              321

<210> SEQ ID NO 11
<211> LENGTH: 688
<212> TYPE: DNA
<213> ORGANISM: Glycine max
<220> FEATURE:
<221> NAME/KEY: unsure
<222> LOCATION: (1)..(688)
<223> OTHER INFORMATION: unsure at all n locations

<400> SEQUENCE: 11
```

```
gcgattccac tcgtacccgg gggtcctcta aatcgacctg cagttgatgc catttattct    60
actaaattgg tttgtgcaat ttttctcaac aagaattttt acaagtttga cactgttaag   120
taataaatct aaattgaaaa gattttctga aaacccctta ccaacacaca acaataacaa   180
taaaagtcag ttacatnaat tacaccttgt taattaaatt ttaggagata tattatttac   240
tataagattc atctcccttt tcatgaaata acacaccat gtattctact ctcgtcactc    300
atgtcttgag tggtcttctt tctgtatgtc gaaatcattt taaccccht ttttttttcca   360
tatctttcaa ttagtattgc accaaatatc tcttcgtgta caattcttgc ccacacaaca   420
tgaacacacc attattaaga tttttgagtta aaaaaattct atttatagat tctttaggtg   480
tcctttttaat tagagcactt gataacaaca ttgttttgtt aaatattcct cagaagcact   540
cttcaaaagc aaaagaactc cacagagcaa gcaatgatat tgttcggtac gaagagacca   600
aatgggcagc agaatctgca aaagctcaag cagaagctga gctttccaat gctaaacaga   660
cagtgaaaga ttttttttct atgattgg                                      688
```

<210> SEQ ID NO 12
<211> LENGTH: 408
<212> TYPE: DNA
<213> ORGANISM: Glycine max
<220> FEATURE:
<221> NAME/KEY: unsure
<222> LOCATION: (1)..(408)
<223> OTHER INFORMATION: unsure at all n locations
<400> SEQUENCE: 12

```
ttaccgtggc attcaacccc atgtttgatc cactgcttga agcctctcgt gaagcaacca    60
atacgggtat taaggaagct ggaatcgatg tgcgcctttg tgacattggt gccgcaattc   120
aagaggtcat ggaatcttat gaagttgaga ttaatggnaa ggtgtatcaa gttaagagta   180
tacggaattt gaatggacat agcattggtc gctaccaaat ccatgctgna aaatctgttc   240
ccattgtgaa ggntggngag cagacaaaga tgnaagaggn tgaattttt gctattgaaa    300
cctttgcatc aacgnnnaaa ggatatgtac gagaagacct gnaatgcagc cactacatga   360
aaaattttga tgttgntcat atcccactga gattgcctag agcgaagc                408
```

<210> SEQ ID NO 13
<211> LENGTH: 416
<212> TYPE: DNA
<213> ORGANISM: Glycine max
<400> SEQUENCE: 13

```
attatatgag ggctcttggg tttttcaagg acactgatgc acccttacct gtaagaatat    60
gattttgtta ttattattat tatatttatt gtgagtctat atatataaga agaattttcc   120
attttgtttc atctaattaa tatagtttta ataattttta aattttgctt tgtttaatgc   180
ttwgtttggt gttggaaatt aagattgttc cagggtttga tgctgctggt gtggtggtga   240
gagtgggaag taaagtgagc aaattcaagg ttggagatga agtttatggt gatatcattg   300
agtatgcttg gaataatcca aagaccattg ggactttggc agaatatact gctactgagg   360
agaaagtgtt ggctcacaaa ccctccaatt taagctttat tgaagcagct agcctt       416
```

<210> SEQ ID NO 14
<211> LENGTH: 1160
<212> TYPE: DNA
<213> ORGANISM: Glycine max

```
<400> SEQUENCE: 14
aggcaccaaa ccaagggatt taaaatttat taaattataa acatgaaatg attaaataaa      60
gagttgaatt cccataattt tatacgtttt attaaatttc actcagcaaa aaatgtatta     120
aaaaatatat tattcccatt tgtctgtctt tatttatgtc atctatttta attttttctga    180 tgtatttaac tggggccaaa ctgaaacatg ttgatcatgc aaaggcctac tcaccatttc    240
acatgtacgt gtcatcaccc agcaacccca tttttctaca taacacacac tccctctcta    300
acactcacac tccaataaca aatatttsac tagctactac tcttcttagt ttctctgttg    360
tatcattttt attgctatat cctaatcaaa cttcactctc aaaatgagtg atcccacact    420
agcacaacag catctagtca agtccacac aacaacacac gaaacagttg ttaccacaca     480
caatcataac caaacaccct caataaatgt gtgttactga attatttaat tatttgtaca    540
cctaactatg attaatattt aattcttcaa aactttgttt atgcatgata accgtgatta    600 attttttattt ttttcccta tgattgagaa caggcctcag gtgaaaagaa gaagattgtg   660
ggggtgttct acaaagggaa tgaatatgct aaattgaatc caaattttgt tggatgtgtt    720
gaaggtgcat tgggaatacg tgagtggctg gaatcacagg gtcatcagta cattgtcact    780
gatgacaaag aaggacctga ttctggttag tacttagtat cttgccaact taattcaagt    840
ttgagtaaac tattattttg atgatttgat ctataaagt gtacaacatt gtgaaattag    900
tctctaacat tgtcacatta gtctctgaaa ttaagataat ttcatatgac aaatgacatg    960
ttattaactc tttttcgtac tgtaaattga aaaatgtggc tacgtgttat atgaaaattg   1020
gttgggacct ggtctcggat catgtaataa tttctatcaa acaaggtatc agagtaatca   1080
acactataat atcatggaat gcaaatgtgt ttgtcccttc aagattttaa ttgcttgaac   1140
tcaatggaat ttgatgttct                                                1160

<210> SEQ ID NO 15
<211> LENGTH: 406
<212> TYPE: DNA
<213> ORGANISM: Glycine max

<400> SEQUENCE: 15
aggaaatact agattttgat atactattat ttaataattt tcctactcga ctaaaatgaa      60
aaaaaaaaca ctaaataat gatatcacta atattattag ctgaattttt tttgtttgtt     120
gaatctttag ttgactgaat ttagtatttg actaaaamaa gaatcatatc acaaactaat    180
ttgcctgtaa ctcattgctt taatttgctt ttaataattg tcagcaagtc tagatttta    240 atgattagat agatagctaa caaaaatacc acactggata catatgaaat caatattaag    300
tttaaagaga tgcaatacgc aatcgatttg attaatgaat ttcaaatgtt ctgcgttaat    360
ttattcaatt accttttaaa ttgaatgttt tcattcctgg gctctg                   406

<210> SEQ ID NO 16
<211> LENGTH: 398
<212> TYPE: DNA
<213> ORGANISM: Glycine max

<400> SEQUENCE: 16
atgatgggat cttgcatatg cccgttggag actccggcga ggttgctttg gaccacaagc      60
ttcttccgtc ataagcttat gatcttctaa taattaataa ttcacgcaca caaacaaaca    120
aacaaacaaa caaaaacac ttcataacaa caacaacaac ccttctgaaa ttctcaacac    180
aagtttcaaa aaacagagta aaagaaacag agcaaaaaca cacacacaaa aacacaaaca    240
```

```
cagacacctt ttaagtatta aggtgtctct ttctctcscc ggaaagtttc tccgtcggcg      300
gtggtgattg accggagtgc catggagtct ggacggattt tctttggtgc ctctgcttca      360
agcggcaaca acatgctctt tctcggcaca actgaact                              398

<210> SEQ ID NO 17
<211> LENGTH: 831
<212> TYPE: DNA
<213> ORGANISM: Glycine max
<220> FEATURE:
<221> NAME/KEY: unsure
<222> LOCATION: (1)..(831)
<223> OTHER INFORMATION: unsure at all n locations

<400> SEQUENCE: 17
tagtaaagcc accaactcca acaccaactt ccccagtggt gtaccctcct cctnnntttc       60
catctccacc agctcctgta gtgaaatcaa acaagggtaa gtgtgtacca catctatstc      120
tttagtaact cctttccgat ctctaatgta attaaatgaa atgattctgt cacatttttc      180
tgctaattta acttttacgt tatttagaaa aaaaatataa aagaaatttg tatcactttt      240
tctttaaaaa taggaaaaat atgtgtgata aaatagataa tgttttacaa tttcattaca      300
gaaatacttt atattttata atgttaatat ttttatttt tcacaatttt tttcttcttt       360
cttattagtt tttggactta aattaaataa tattttaat cctgtcatgt gggtttagt        420 attcttaata ttattttctt gatttgatta ctgtaaaatg ttttagtaag cttaactaa       480 aacagacaaa gaaaatatt tcaagaagat taaaatggaa aaaagaatc ttataataca       540 tggattaaaa aattagtgaa gccttacttt tgttttctt ttctctttgt tacacgtctt      600
caccttgttg tctttgttat cctttttcac atctaatgat ggatgtgaga gaagaaccat     660
gcatggtctt aattgtttat gtgattaatg gctttaaagt atagaacttt taagtaagat     720
cagttgagtt aattaatgaa acatggtctt ttgttttcca aatttttttg tgggcagatt     780
gcattccact aagggattat aggtgctcat tacactcaag gaagaaattg t               831

<210> SEQ ID NO 18
<211> LENGTH: 520
<212> TYPE: DNA
<213> ORGANISM: Glycine max

<400> SEQUENCE: 18
atcttggttt tccaatcgcg cagcccgagc ggccatcwga acaacagtat ctacgtcaac       60
tcctttagca aaatctaca gaaaacattg aaaacacttg tgtgagcata cgacaaggca      120
aataagaaaa caacacagta caaaactgac tacttctaac ctcaataaga ttcttgtcaa     180
ctgtcagttt attcaaagtc aaagttccag ttttgtcgct acataataca tccattcctg     240
ccatctcttc tattgctgtc attcttttag taatagcacc ctgcaatgat tatataaagc     300
ataaactata aagactaaca tctaattgat taaaacttga dacaactgct tttcaagaag     360
cactaatgtc tacctgctga gctaagcgat gggatccaat tgccattgtc actgacaaaa     420
cagtaggcat ggcaatagga attcctccga taagaagcac gagcagattg tcaatcccag     480
gacgatattc ccggtgttga attgggtaca tgacaatgat                            520

<210> SEQ ID NO 19
<211> LENGTH: 337
<212> TYPE: DNA
<213> ORGANISM: Glycine max
```

<400> SEQUENCE: 19

```
ctttgattct tgccagtctt tttcattctt tttcattctt aaatccatca aatgaaccta      60
ttgatatgac tgaaaccttt ggattagcca agactaaagc tactccactt gagattttaa     120
ttaagccacg attatcttct agttgttaty tataaaagca tgtgaatctt gtcttagcgg     180
tttgtggaaa gtctgttgtt aaactatgtg atcttctttt agataaatca ggtttgcctg     240
ataaattata ttttcgtcaa aagggcattt ttggaattca caaaattgtc atcatgtggt     300
gttgaaataa ggtgtgttgt aataaggttt aaggctt                              337
```

<210> SEQ ID NO 20
<211> LENGTH: 1020
<212> TYPE: DNA
<213> ORGANISM: Pseudomonas maltophilia

<400> SEQUENCE: 20

```
atgaccttcg tccgcaatgc ctggtatgtg gcggcgctgc ccgaggaact gtccgaaaag      60
ccgctcggcc ggacgattct cgacacaccg ctcgcgctct accgcagcc cgacggtgtg     120
gtcgcggcgc tgctcgacat ctgtccgcac cgcttcgcgc cgctgagcga cggcatcctc     180
gtcaacggcc atctccaatg cccctatcac gggctggaat cgatggcgg cgggcagtgc     240
gtccataacc cgcacggcaa tggcgcccgc ccggcttcgc tcaacgtccg ctccttcccg     300
gtggtggagc gcgacgcgct gatctggatc tggcccggcg atccggcgct ggccgatcct     360
ggggcgatcc ccgacttcgg ctgccgcgtc gatcccgcct atcggaccgt cggcggctat     420
gggcatgtcg actgcaacta caagctgctg gtcgacaacc tgatggacct cggccacgcc     480
caatatgtcc atcgcgccaa cgcccagacc gacgccttcg accggctgga gcgcgaggtg     540
atcgtcggcg acggtgagat acaggcgctg atgaagattc ccggcggcac gccgagcgtg     600
ctgatggcca gttcctgcg cggcgccaat accccgtcg acgcttggaa cgacatccgc     660
tggaacaagg tgagcgcgat gctcaacttc atcgcggtgg cgccggaagg cacccccgaag   720
gagcagagca tccactcgcg cggtacccat atcctgaccc ccgagacgga ggcgagctgc    780
cattatttct tcggctcctc gcgcaatttc ggcatcgacg atccggagat ggacggcgtg    840
ctgcgcagct ggcaggctca ggcgctggtc aaggaggaca aggtcgtcgt cgaggcgatc    900
gagcgccgcc gcgcctatgt cgaggcgaat ggcatccgcc cggcgatgct gtcgtgcgac    960
gaagccgcag tccgtgtcag ccgcgagatc gagaagcttg agcagctcga agccgcctga   1020
```

<210> SEQ ID NO 21
<211> LENGTH: 339
<212> TYPE: PRT
<213> ORGANISM: Pseudomonas maltophilia

<400> SEQUENCE: 21

```
Met Thr Phe Val Arg Asn Ala Trp Tyr Val Ala Ala Leu Pro Glu Glu
1               5                   10                  15

Leu Ser Glu Lys Pro Leu Gly Arg Thr Ile Leu Asp Thr Pro Leu Ala
                20                  25                  30

Leu Tyr Arg Gln Pro Asp Gly Val Val Ala Ala Leu Leu Asp Ile Cys
            35                  40                  45

Pro His Arg Phe Ala Pro Leu Ser Asp Gly Ile Leu Val Asn Gly His
        50                  55                  60

Leu Gln Cys Pro Tyr His Gly Leu Glu Phe Asp Gly Gly Gly Gln Cys
65                  70                  75                  80
```

```
Val His Asn Pro His Gly Asn Gly Ala Arg Pro Ala Ser Leu Asn Val
            85                  90                  95
Arg Ser Phe Pro Val Val Glu Arg Asp Ala Leu Ile Trp Ile Trp Pro
           100                 105                 110
Gly Asp Pro Ala Leu Ala Asp Pro Gly Ala Ile Pro Asp Phe Gly Cys
           115                 120                 125
Arg Val Asp Pro Ala Tyr Arg Thr Val Gly Gly Tyr Gly His Val Asp
           130                 135                 140
Cys Asn Tyr Lys Leu Leu Val Asp Asn Leu Met Asp Leu Gly His Ala
145                 150                 155                 160
Gln Tyr Val His Arg Ala Asn Ala Gln Thr Asp Ala Phe Asp Arg Leu
               165                 170                 175
Glu Arg Glu Val Ile Val Gly Asp Gly Glu Ile Gln Ala Leu Met Lys
           180                 185                 190
Ile Pro Gly Gly Thr Pro Ser Val Leu Met Ala Lys Phe Leu Arg Gly
           195                 200                 205
Ala Asn Thr Pro Val Asp Ala Trp Asn Asp Ile Arg Trp Asn Lys Val
           210                 215                 220
Ser Ala Met Leu Asn Phe Ile Ala Val Ala Pro Glu Gly Thr Pro Lys
225                 230                 235                 240
Glu Gln Ser Ile His Ser Arg Gly Thr His Ile Leu Thr Pro Glu Thr
               245                 250                 255
Glu Ala Ser Cys His Tyr Phe Phe Gly Ser Ser Arg Asn Phe Gly Ile
           260                 265                 270
Asp Asp Pro Glu Met Asp Gly Val Leu Arg Ser Trp Gln Ala Gln Ala
           275                 280                 285
Leu Val Lys Glu Asp Lys Val Val Glu Ala Ile Glu Arg Arg Arg
           290                 295                 300
Ala Tyr Val Glu Ala Asn Gly Ile Arg Pro Ala Met Leu Ser Cys Asp
305                 310                 315                 320
Glu Ala Ala Val Arg Val Ser Arg Glu Ile Lys Leu Glu Gln Leu
               325                 330                 335
Glu Ala Ala

<210> SEQ ID NO 22
<211> LENGTH: 1023
<212> TYPE: DNA
<213> ORGANISM: Pseudomonas maltophilia

<400> SEQUENCE: 22
atggccacct tcgtccgcaa tgcctggtat gtggcggcgc tgcccgagga actgtccgaa      60
aagccgctcg gccggacgat tctcgacaca ccgctcgcgc tctaccgcca gcccgacggt     120
gtggtcgcgg cgctgctcga catctgtccg caccgcttcg cgccgctgag cgacggcatc     180
ctcgtcaacg ccatctccat gccccctat cacgggctgg aattcgatgg cggcgggcag     240
tgcgtccata acccgcacgg caatggcgcc cgccgggctt cgctcaacgt ccgctccttc     300
ccggtggtgg agcgcgacgc gctgatctgg atctgtcccg gcgatccggc gctggccgat     360
cctggggcga tccccgactt cggctgccgc gtcgatcccg cctatcggac cgtcggcggc     420
tatgggcatg tcgactgcaa ctacaagctg ctggtcgaca acctgatgga cctcggccac     480
gcccaatatg tccatcgcgc caacgcccag accgacgcct cgaccggct ggagcgcgag     540 gtgatcgtcg cgacggtga gatacaggcg ctgatgaaga ttcccggcgg cacgccgagc     600
gtgctgatgg ccaagttcct gcgcggcgcc aatacccccg tcgacgcttg gaacgacatc     660
```

-continued

```
cgctggaaca aggtgagcgc gatgctcaac ttcatcgcgg tggcgccgga aggcaccccg      720
aaggagcaga gcatccactc gcgcggtacc catatcctga cccccgagac ggaggcgagc      780
tgccattatt tcttcggctc ctcgcgcaat tcggcatcg acgatccgga gatggacggc       840
gtgctgcgca gctggcaggc tcaggcgctg gtcaaggagg acaaggtcgt cgtcgaggcg      900
atcgagcgcc gccgcgccta tgtcgaggcg aatggcatcc gcccggcgat gctgtcgtgc     960
gacgaagccg cagtccgtgt cagccgcgag atcgagaagc ttgagcagct cgaagccgcc     1020
tga                                                                    1023
```

<210> SEQ ID NO 23
<211> LENGTH: 340
<212> TYPE: PRT
<213> ORGANISM: Pseudomonas maltophilia

<400> SEQUENCE: 23

```
Met Ala Thr Phe Val Arg Asn Ala Trp Tyr Val Ala Ala Leu Pro Glu
1               5                   10                  15

Glu Leu Ser Glu Lys Pro Leu Gly Arg Thr Ile Leu Asp Thr Pro Leu
            20                  25                  30

Ala Leu Tyr Arg Gln Pro Asp Gly Val Val Ala Ala Leu Leu Asp Ile
        35                  40                  45

Cys Pro His Arg Phe Ala Pro Leu Ser Asp Gly Ile Leu Val Asn Gly
    50                  55                  60

His Leu Gln Cys Pro Tyr His Gly Leu Glu Phe Asp Gly Gly Gly Gln
65                  70                  75                  80

Cys Val His Asn Pro His Gly Asn Gly Ala Arg Pro Ala Ser Leu Asn
                85                  90                  95

Val Arg Ser Phe Pro Val Val Glu Arg Asp Ala Leu Ile Trp Ile Cys
            100                 105                 110

Pro Gly Asp Pro Ala Leu Ala Asp Pro Gly Ala Ile Pro Asp Phe Gly
        115                 120                 125

Cys Arg Val Asp Pro Ala Tyr Arg Thr Val Gly Gly Tyr Gly His Val
    130                 135                 140

Asp Cys Asn Tyr Lys Leu Leu Val Asp Asn Leu Met Asp Leu Gly His
145                 150                 155                 160

Ala Gln Tyr Val His Arg Ala Asn Ala Gln Thr Asp Ala Phe Asp Arg
                165                 170                 175

Leu Glu Arg Glu Val Ile Val Gly Asp Gly Glu Ile Gln Ala Leu Met
            180                 185                 190

Lys Ile Pro Gly Gly Thr Pro Ser Val Leu Met Ala Lys Phe Leu Arg
        195                 200                 205

Gly Ala Asn Thr Pro Val Asp Ala Trp Asn Asp Ile Arg Trp Asn Lys
    210                 215                 220

Val Ser Ala Met Leu Asn Phe Ile Ala Val Ala Pro Glu Gly Thr Pro
225                 230                 235                 240

Lys Glu Gln Ser Ile His Ser Arg Gly Thr His Ile Leu Thr Pro Glu
                245                 250                 255

Thr Glu Ala Ser Cys His Tyr Phe Phe Gly Ser Ser Arg Asn Phe Gly
            260                 265                 270

Ile Asp Asp Pro Glu Met Asp Gly Val Leu Arg Ser Trp Gln Ala Gln
        275                 280                 285

Ala Leu Val Lys Glu Asp Lys Val Val Glu Ala Ile Glu Arg Arg
    290                 295                 300
```

```
Arg Ala Tyr Val Glu Ala Asn Gly Ile Arg Pro Ala Met Leu Ser Cys
305                 310                 315                 320

Asp Glu Ala Ala Val Arg Val Ser Arg Glu Ile Glu Lys Leu Glu Gln
                325                 330                 335

Leu Glu Ala Ala
            340

<210> SEQ ID NO 24
<211> LENGTH: 26
<212> TYPE: DNA
<213> ORGANISM: Glycine max

<400> SEQUENCE: 24
atcctaggtt tcagttcata gatggc                                          26

<210> SEQ ID NO 25
<211> LENGTH: 26
<212> TYPE: DNA
<213> ORGANISM: Glycine max

<400> SEQUENCE: 25
ggacaattgc atcaacatgt atacaa                                          26

<210> SEQ ID NO 26
<211> LENGTH: 18
<212> TYPE: DNA
<213> ORGANISM: Glycine max

<400> SEQUENCE: 26
tgactagcat gtatctat                                                   18

<210> SEQ ID NO 27
<211> LENGTH: 19
<212> TYPE: DNA
<213> ORGANISM: Glycine max

<400> SEQUENCE: 27
atgactaaca tgtatctat                                                  19

<210> SEQ ID NO 28
<211> LENGTH: 25
<212> TYPE: DNA
<213> ORGANISM: Glycine max

<400> SEQUENCE: 28
ttctcctttt ggtcctcaat tatga                                           25

<210> SEQ ID NO 29
<211> LENGTH: 26
<212> TYPE: DNA
<213> ORGANISM: Glycine max

<400> SEQUENCE: 29
catctgcttt catttcctca tttatg                                          26

<210> SEQ ID NO 30
<211> LENGTH: 18
<212> TYPE: DNA
<213> ORGANISM: Glycine max

<400> SEQUENCE: 30
tgtgtcctat atgatctt                                                   18
```

```
<210> SEQ ID NO 31
<211> LENGTH: 17
<212> TYPE: DNA
<213> ORGANISM: Glycine max

<400> SEQUENCE: 31
tgtcctgtat gatctta                                                   17

<210> SEQ ID NO 32
<211> LENGTH: 25
<212> TYPE: DNA
<213> ORGANISM: Glycine max

<400> SEQUENCE: 32
tctcatggtc tatgatggca atttt                                          25

<210> SEQ ID NO 33
<211> LENGTH: 26
<212> TYPE: DNA
<213> ORGANISM: Glycine max

<400> SEQUENCE: 33
acatttgtgg ttaccttgta gatgga                                         26

<210> SEQ ID NO 34
<211> LENGTH: 15
<212> TYPE: DNA
<213> ORGANISM: Glycine max

<400> SEQUENCE: 34
agttgggcta tgcaa                                                     15

<210> SEQ ID NO 35
<211> LENGTH: 15
<212> TYPE: DNA
<213> ORGANISM: Glycine max

<400> SEQUENCE: 35
tgggctgtgc aagta                                                     15

<210> SEQ ID NO 36
<211> LENGTH: 27
<212> TYPE: DNA
<213> ORGANISM: Glycine max

<400> SEQUENCE: 36
agaagcagaa agaaaggaaa tgatggt                                        27

<210> SEQ ID NO 37
<211> LENGTH: 25
<212> TYPE: DNA
<213> ORGANISM: Glycine max

<400> SEQUENCE: 37
gctgccaaat gcctaatcta cacta                                          25

<210> SEQ ID NO 38
<211> LENGTH: 20
<212> TYPE: DNA
<213> ORGANISM: Glycine max

<400> SEQUENCE: 38
```

```
agtttacact tacaaatatt                                          20

<210> SEQ ID NO 39
<211> LENGTH: 22
<212> TYPE: DNA
<213> ORGANISM: Glycine max

<400> SEQUENCE: 39
agagtttaca cttacatata tt                                       22

<210> SEQ ID NO 40
<211> LENGTH: 26
<212> TYPE: DNA
<213> ORGANISM: Glycine max

<400> SEQUENCE: 40
gagtggtctt ctttctgtat gtcgaa                                   26

<210> SEQ ID NO 41
<211> LENGTH: 27
<212> TYPE: DNA
<213> ORGANISM: Glycine max

<400> SEQUENCE: 41
tggtgcaata ctaattgaaa gatatgg                                  27

<210> SEQ ID NO 42
<211> LENGTH: 13
<212> TYPE: DNA
<213> ORGANISM: Glycine max

<400> SEQUENCE: 42 acccccctttt ttt                                                13

<210> SEQ ID NO 43
<211> LENGTH: 17
<212> TYPE: DNA
<213> ORGANISM: Glycine max

<400> SEQUENCE: 43
attttaaccc ccttttt                                             17

<210> SEQ ID NO 44
<211> LENGTH: 28
<212> TYPE: DNA
<213> ORGANISM: Glycine max

<400> SEQUENCE: 44
aagaagaatt ttccattttg tttcatct                                 28

<210> SEQ ID NO 45
<211> LENGTH: 22
<212> TYPE: DNA
<213> ORGANISM: Glycine max

<400> SEQUENCE: 45
gcatcaaacc ctggaacaat ct                                       22

<210> SEQ ID NO 46
<211> LENGTH: 14
<212> TYPE: DNA
<213> ORGANISM: Glycine max

<400> SEQUENCE: 46
```

-continued

```
ccaacaccaa acta                                                     14

<210> SEQ ID NO 47
<211> LENGTH: 14
<212> TYPE: DNA
<213> ORGANISM: Glycine max

<400> SEQUENCE: 47
caacaccaaa caaa                                                     14

<210> SEQ ID NO 48
<211> LENGTH: 26
<212> TYPE: DNA
<213> ORGANISM: Glycine max

<400> SEQUENCE: 48
aaccccattt ttctacataa cacaca                                        26

<210> SEQ ID NO 49
<211> LENGTH: 32
<212> TYPE: DNA
<213> ORGANISM: Glycine max

<400> SEQUENCE: 49
caataaaaat gatacaacag agaaactaag aa                                 32

<210> SEQ ID NO 50
<211> LENGTH: 19
<212> TYPE: DNA
<213> ORGANISM: Glycine max

<400> SEQUENCE: 50
agtagtagct agtgaaata                                                19

<210> SEQ ID NO 51
<211> LENGTH: 16
<212> TYPE: DNA
<213> ORGANISM: Glycine max

<400> SEQUENCE: 51
agctagtcaa atattt                                                   16

<210> SEQ ID NO 52
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 52
tactggtatt gtatgnntca atcagagtga ttgatagaca aagantatga ttgcttacac    60
tattcactga aaatgattgt ttcaaacatg tttgagtgat tagtggtccc acaaaatgca   120
cactgtctat tgtctactgt ctgagacccc accctaaatc attacacgtg tcaaccttat   180
aggaacccag tacaatatcc rgaggctgtc aatctcattc tttttntttt ggtactttct   240
gcttctccac taaactaatt aattactact tcttctatat atacattttta atataaaatt   300 t                                                                  301

<210> SEQ ID NO 53
```

```
<211> LENGTH: 26
<212> TYPE: DNA
<213> ORGANISM: Glycine max

<400> SEQUENCE: 53
tgtcaacctt ataggaaccc agtaca                                         26

<210> SEQ ID NO 54
<211> LENGTH: 26
<212> TYPE: DNA
<213> ORGANISM: Glycine max

<400> SEQUENCE: 54
gtttagtgga gaagcagaaa gtacca                                         26

<210> SEQ ID NO 55
<211> LENGTH: 18
<212> TYPE: DNA
<213> ORGANISM: Glycine max

<400> SEQUENCE: 55
ttgacagcct ctggatat                                                  18

<210> SEQ ID NO 56
<211> LENGTH: 15
<212> TYPE: DNA
<213> ORGANISM: Glycine max

<400> SEQUENCE: 56
acagcctccg gatat                                                     15
```